United States Patent
Luo et al.

(10) Patent No.: US 9,469,674 B2
(45) Date of Patent: Oct. 18, 2016

(54) α-CONOTOXIN PEPTIDE, PHARMACEUTICAL COMPOSITION AND USE THEREOF

(71) Applicant: HAINAN UNIVERSITY, Haikou Hainan (CN)

(72) Inventors: Sulan Luo, Haikou Hainan (CN); Dongting Zhangsun, Haikou Hainan (CN); Yong Wu, Haikou Hainan (CN); Xiaopeng Zhu, Haikou Hainan (CN); Yuanyan Hu, Haikou Hainan (CN); Hui Bing, Haikou Hainan (CN); J. Michael McIntosh, Haikou Hainan (CN)

(73) Assignee: HAINAN UNIVERSITY, Haikou Hainan (CN)

( * ) Notice: Subject to any disclaimer, the term of this patent is extended or adjusted under 35 U.S.C. 154(b) by 0 days.

(21) Appl. No.: 14/419,584

(22) PCT Filed: Jun. 18, 2013

(86) PCT No.: PCT/CN2013/077363
§ 371 (c)(1),
(2) Date: Feb. 4, 2015

(87) PCT Pub. No.: WO2014/023129
PCT Pub. Date: Feb. 13, 2014

(65) Prior Publication Data
US 2015/0299276 A1    Oct. 22, 2015

(30) Foreign Application Priority Data

Aug. 7, 2012  (CN) .......................... 2012 1 0277619
Sep. 6, 2012  (CN) .......................... 2012 1 0325531
Sep. 19, 2012  (CN) .......................... 2012 1 0347966

(51) Int. Cl.
| | |
|---|---|
| A61K 38/10 | (2006.01) |
| C07K 7/00 | (2006.01) |
| C07K 1/00 | (2006.01) |
| C07K 14/435 | (2006.01) |
| G01N 33/94 | (2006.01) |
| C07K 1/06 | (2006.01) |
| C07K 1/16 | (2006.01) |
| C07K 1/30 | (2006.01) |
| G01N 33/50 | (2006.01) |
| A61K 38/00 | (2006.01) |

(52) U.S. Cl.
CPC ......... *C07K 14/43504* (2013.01); *C07K 1/061* (2013.01); *C07K 1/16* (2013.01); *C07K 1/30* (2013.01); *G01N 33/5032* (2013.01); *G01N 33/944* (2013.01); *A61K 38/00* (2013.01); *C07K 2319/00* (2013.01); *G01N 2333/70571* (2013.01); *G01N 2500/04* (2013.01)

(58) Field of Classification Search
CPC ........... A61K 38/00; C07K 14/43504; C07K 2319/00; C07K 1/061; C07K 1/16; C07K 1/30; G01N 33/944; G01N 2500/04; G01N 33/5032; G01N 2333/70571
See application file for complete search history.

(56) References Cited

U.S. PATENT DOCUMENTS 6,797,808 B1    9/2004  Watkins et al.

FOREIGN PATENT DOCUMENTS

| CN | 101041691 A | 9/2007 | |
|---|---|---|---|
| CN | 101381403 A | 3/2009 | |
| CN | 101448516 A | 6/2009 | |
| CN | 101745097 A | 6/2010 | |
| CN | 101979572 A | 2/2011 | |
| CN | 102154300 A  * | 8/2011 | ............. C12N 15/12 |
| CN | 102875653 A | 1/2013 | |
| WO | WO 2007/118270 A1 | 10/2007 | |

OTHER PUBLICATIONS

Machine translation of CN 102154300 A , pp. 1-14, accessed Jan. 8, 2016.*
Machine translation of CN 101381403 A, pp. 1-12, accessed Jan. 8, 2016.*
Machine translation of CN 101448516 A, pp. 1-65, accessed Jul. 28, 2015.*
Luo et al, Characterization of a Novel a-Conotoxin from Conus textile That Selectively Targets a6/a3b2b3 Nicotinic Acetylcholine Receptors, The Journal of Biological Chemistry, 2013, 288, pp. 894-902, published on Nov. 26, 2012.*

(Continued)

*Primary Examiner* — Julie Ha
*Assistant Examiner* — Li Ni Komatsu
(74) *Attorney, Agent, or Firm* — Scully Scott Murphy & Presser

(57) ABSTRACT

The present invention provides a novel α-conotoxin peptide, pharmaceutical composition and use thereof. The present invention further provides a propeptide of the conotoxin peptide, a nucleic acid construct, expression vector and transformed cell of the conotoxin peptide as well as a fused protein of the conotoxin peptide. The present invention discloses a method for blocking acetylcholine receptors as well as a use of the conotoxin peptide in the manufacture of a medicament. The α-conotoxin peptide of the present invention can specifically block acetylcholine receptor (nAChRs, such as α3β2 nAChRs, α6/α3β2β3 nAChR or α3β4 nAChR or α6/α3β4 nAChR), has activity for treatment of neuralgia, addiction, Parkinson's disease, dementia, schizophrenia, cancers, and can be used in the manufacture of a medicament for analgesia and smoking cessation and drug-withdrawal, a medicament for treatment of mental diseases and cancers, as well as a tool drug for neurosciences.

8 Claims, 19 Drawing Sheets

(56) References Cited

OTHER PUBLICATIONS

Chang, D. et al., "alpha-conotoxin, partial [Conus sanguinolentus]" Genebank AFD18554.1 (Jul. 30, 2012) 2 pages.

International Search Report dated Oct. 3, 2013, issued in International Application No. PCT/CN2013/077363.
Supplementary European Search Report dated Mar. 16, 2016 issued in corresponding European Patent Application No. EP 13 82 8357.7.

* cited by examiner

SEQ ID NO: 67  GTGGTTCTGGGTCCAGC*ATTTCGTGGCAGGGACGCCGCAGCCAAAGCGTCT*  51
SEQ ID NO: 3    V  V  L  G  P  A  *F  R  G  R  D  A  A  A  K  A  S*

*GGCCTGGTTGGTCTGACTGACAGGAGA*GGATGCTGTTCTCATCCTGCCTGT  102
 *G  L  V  G  L  T  D  R  R*  G  C  C  S  H  P  A  C
              processing 1      Mature Toxin AACGTAGATCATCCAGAAATTTGTGGCTGAAGACGCTGATGCTCCAGG  150
 N  V  D  H  P  E  I  C #G  *  R  R  *  C  S  R
                    processing 2 (#, C-terminal carboxamide)

ACCCTCTGAACCACGACA  168
 T  L  *  T  T  T

Fig.1

SEQ ID NO: 4

SEQ ID NO: 4

SEQ ID NO: 21   GTGGTTCTGGGTCCAGCATTTGATGGCAGGAATACCTCAGCCAACAACAA 50
SEQ ID NO: 15   V  V  L  G  P  A  F  D  G  R  N  T  S  A  N  N  K

AGCGACTGACCTGATGGCTCTGCCTGTCAGGGGATGCTGTTCCGATCCTC 100
A  T  D  L  M  A  L  P  V  R  G  C  C  S  D  P  P
              processing 1              Mature Toxin CCTGTAGAAACAAGCACCCAGATCTTTGTGGCGGAAGACGCTGA       144
C  R  N  K  H  P  D  L  C  G  G  R  R  *
         TxIB = processing 2    processing 3 = TxIB(G)

TGCTCCAGGACCCTCTGAACCACGAC                         170
C  S  R  T  L  *  T  T

SEQ ID NO: 12  G C CSDPP CRNKHPDL C G#

SEQ ID NO: 13  G C CSDPP CRNKHPDL CGG#

SEQ ID NO: 22/23  GTGGTTCTGGGTCCAGCATTTGATGGCAGGAATGCTGCAGGCAACGACAAA 51
SEQ ID NO: 26/27  V  V  L  G  P  A  F  D  G  R  N  A  A  G  N  D  K

ATGTCCGCCCTGATGGCTCTGACCA (C/T) CAGGGGATGCTGTTCCATCCTGTC 102
M  S  A  L  M  A  L  T  (T/L)  R  G  C  C  S  H  P  V
                              processing 1    Mature Toxin TGTAGCGCGATGAGTCCAATCTGTGGCTGAAGACGCTGATGCTCCAGGACC 153
C  S  A  M  S  P  I  C  #  *  R  R  *  C  S  R  T
                        processing 2 (#, C-terminal carboxamide)

CTCTGAACCACGACA    168
L  *  T  T  T

Fig.14

SEQ ID NO: 28

```
       ┌────── 3         4
       │
    GC CSHPVCSAMSPIC #
    1  2└──────────────┘
```

α-CONOTOXIN PEPTIDE, PHARMACEUTICAL COMPOSITION AND USE THEREOF

TECHNICAL FIELD

The present invention pertains to fields of biochemistry and molecular biology, relates to a novel α-conotoxin peptide, pharmaceutical composition, preparation method and use thereof. The present invention further relates to a propeptide of the conotoxin peptide, a nucleic acid construct, expression vector and transformed cell of the conotoxin peptide as well as fused protein of the conotoxin peptide. The present invention further relates to a method for blocking acetylcholine receptors as well as a use of the conotoxin peptide in the manufacture of a medicament.

INCORPORATION BY REFERENCE OF SEQUENCE LISTING

The Sequence Listing in an ASCII text file, named as 31726_SEQ3_2-10-06-2015.txt of 21 KB, created on Oct. 6, 2015, and submitted to the United States Patent and Trademark Office via EFS-Web, is incorporated herein by reference.

BACKGROUND ART

Conotoxin (CTx, Conopeptide) is secreted by *Conus*, a kind of carnivore mollusc living in tropical seas, which has special function of regulating various ion channels, and shows important value in clinic. Conotoxin usually contains 10-46 amino acids enriching with disulfide bonds, has strong biological activity, can specifically act to receptors and ion channels on animal cell membrane, specially has relatively high selectivity to voltage-gated or ligand-gated ion channels (including few G-protein associated receptors, etc.). Conotoxin can be classified into different gene families according to similarity of precursor protein endoplasmic reticulum targeting sequence and cysteine pattern. So far, all known conotoxins can be classified into 19 superfamilies, i.e., A, B, C, D, S, M, I1, I2, I3, J, L, O1, O2, O3, P, T, V, Y, K (Sulan Luo, Sean Christensen, Dongting Zhangsun, Yong Wu, Yuanyan Hu, Xiaopeng Zhu, Sandeep Chhabra, Raymond S. Norton, and J. Michael McIntosh. A Novel Inhibitor of α9α10 Nicotinic Acetylcholine Receptors from *Conus vexillum* Delineates a New Conotoxin Superfamily. PLoS ONE, (2013) 8(1): e54648 (1-10); Kaas Q, Yu R, Jin A H, Dutertre S and Craik D J. ConoServer: updated content, knowledge, and discovery tools in the conopeptide database. *Nucleic Acids Research* (2012) [Ahead of print]; Ye M, Khoo K K, Xu S, Zhou M, Boonyalai N, Perugini M A, Shao X, Chi C, Galea C A, Wang C & Norton R S. A helical conotoxin from *Conus imperialis* has a novel cysteine framework and defines a new superfamily. *Journal of Biological Chemistry* (2012) 287, 14973-14983). Conotoxin can be classified into pharmacological families α, ω, μ, δ and so on according to receptor target thereof. According to receptor target type, each superfamily of conotoxin can further be classified into α, αA, κA (A-superfamily), ω, δ, κ, μO (O-superfamily), μ, ψ, κM (M-superfamily), etc. (subtypes).

Wherein, α-conotoxin is a nicotine acetylcholine receptor (nAChRs) subtype specific blocking agent that is the one with the best selectivity known in the art. Hence, α-conotoxin and its action target nAChRs are of very important value in studying mechanisms of many diseases as well as research and development of drugs. α-Conotoxin is one of the earliest known conotoxins, has a relatively small molecular weight, usually consists of 12-19 amino acid residues, and is rich in disulfide bonds. There are many kinds of α-conotoxins with diverse activities and complicated structure changes. The α-conotoxins can be classified according to their highly conservative signal peptide sequences, pharmacological activities and cysteine patterns. The cysteine pattern of α-conotoxin is CC-C-C, in which the linkage mode of disulfides of natural peptides is C1-C3 and C2-C4, which is called as globular isomer, and 2 loops are formed between disulfide bonds. The α-conotoxin linear peptides containing 4 cysteines usually generate 3 isomers after oxidation and folding, besides natural peptide disulfide bond linkage mode of C1-C3 and C2-C4 (globular isomer), other two isomers are separately ribbon isomer and bead isomer. The ribbon isomer has linkage mode of disulfides as C1-04 and C2-C3; while the bead isomer has linkage mode of disulfides as C1-02 and C3-C4. The globular isomer has complete biological activity, the ribbon isomer exhibits biological activity sometimes via different action mechanism, while the bead isomer usually has a reduced activity. There are 2 loops formed between disulfide bonds, α-conotoxins can be classified into many subfamilies such as α3/5, α4/7, α4/6, α4/4 and α4/3 according to number of amino acids between the $2^{nd}$ and $3^{rd}$ cysteines and between the $3^{rd}$ and the $4^{th}$ cysteines, and the differences in features and residue composition of each loop form the basis that different conotoxins act on different receptor subtypes (Ulens C, Hogg R C, Celie P H, et al. Structural determinants of selective alpha-conotoxin binding to a nicotinic acetylcholine receptor homolog AChBP[J]. *Proc Natl Acad Sci* USA 2006; 103: 3615-20; McIntosh, J. M.; Santos, A. D.; Olivera, B. M., *Conus* peptides targeted to specific nicotinic acetylcholine receptor subtypes. *Annual review of biochemistry* 1999, 68, 59-88; Terlau, H.; Olivera, B. M., *Conus* venoms: a rich source of novel ion channel-targeted peptides. *Physiological reviews* 2004, 84 (1), 41-68. Gehrmann J, Alewood P F, Craik D J. Structure determination of the three disulfide bond isomers of alpha-conotoxin GI: a model for the role of disulfide bonds in structural stability. *J Mol Biol.* 1998, 278(2):401-15; Grishin A A, Wang C I, Muttenthaler M, Alewood P F, Lewis R J, Adams D J. Alpha-conotoxin AuIB isomers exhibit distinct inhibitory mechanisms and differential sensitivity to stoichiometry of alpha3beta4 nicotinic acetylcholine receptors. *J Biol Chem.* 2010, 285 (29): 22254-63).

Nicotine acetylcholine receptors (nAChRs) are membrane proteins that are prevalent in animal kingdom and have important physiological actions and clinical research significance, and they are the earliest receptors found by human and can be classified into two groups: muscular type acetylcholine receptors and neurologic type acetylcholine receptors. The nAChRs are allosteric membrane proteins on cell membrane, mediate many physiological functions of central and peripheral nervous systems, including learning, memory, addiction, response, and analgesia and motion control. The nAChRs activate release of many neurotransmitters such as dopamine, noradrenaline, serotonin, γ-aminobutyric acid. It is confirmed that nAChRs are critical targets for screening medicines in diagnosis and treatment of a large group of important diseases, and these diseases include pains, addiction of tobacco, alcohol and drugs, amentia, dementia, schizophrenia, disorder of central nerves, epilepsy, Parkinson's disease, mental diseases, neuromuscular blockade, myasthenia gravis, depression, hypertension, arrhythmia, asthma, muscular flaccidity, apoplexy, breast cancer and lung cancer. So far, there is no medicine for symptomatic treatment of these diseases. Common non-selective nAChRs agonists such as nicotine could relieve symptoms of the above nerve diseases, but they have strong side-effects on heart and gastrointestinal tract and addiction. Hence, the key for treatment of the above diseases is to develop ligand medicines having high selectivity on various subtypes of nAChRs. (Livett B G, Sandal) DW, Keays D, Down J, Gayler K R, Satkunanathan N, Khalil Z. Therapeutic applications of conotoxins that target the neuronal nicotinic acetylcholine receptor. *Toxicon,* 2006, 48(7):810-829; Taly A, Corringer P J, Guedin D, Lestage P, Changeux J P. Nicotinic receptors: allosteric transitions and therapeutic targets in the nervous system. *Nat Rev Drug Discov.* 2009, 8(9): 733-50; Layla A, McIntosh J M. Alpha-conotoxins as pharmacological probes of nicotinic acetylcholine receptors [J]. *Acta Pharmacol Sin* 2009 June; 30 (6): 771-783.).

However, the precondition for developing such medicines is to obtain selective compounds capable of specifically binding to various subtypes of nAChRs, which can be used as tool drugs to study and identify fine composition and physiological functions of various subtypes, or can be directly used as therapeutic drugs for treatment of associated diseases. In addition, the activation of nicotine acetylcholine receptor on tumor cell membrane of breast cancer and small cell lung cancer can promote tumor cell proliferation, so blocking the activation of these receptors with drugs can effectively be used to perform early diagnosis or treatment of these catastrophic cancers.

The nAChRs are assembled with different α and β subunits to form many subtypes, and each subtype has distinctive pharmacological features, among which muscular acetylcholine receptors consist of 5 subunits, including two α1 subunits, one β subunit, one δ subunit and one γ or ε subunit, and whether it is γ or ε subunit depends on whether it is fetal or adult acetylcholine receptor. The subtypes of neurologic nAChRs of mammals are far more complex than muscular nAChRs, have at least 8 α subunits, 3 β subunits, which separately are: α2-α7, α9, α10 (α8 in chicken), and β2-β4. Wherein, α2, α3 and α4 can separately bind to β2 or β4 to form functional receptors, such as α2β2, α3β2, α2β4; α9 and α10 are bound to form functional receptor α9α10 nAChRs. In addition, α7 and α9 can form homologous multimers. Due to lack of ligand compounds with high selectivity to various subtypes, there are a lot of challenges to study and illustrate the fine structure and function of various nAChRs subtypes.

Drug addiction is both medical challenge and social problem. Smoking addiction is caused with nicotine in tobacco, of which receptors in vivo are nicotine acetylcholine receptors (nAChRs) (Azam L, McIntosh J M. Alpha-conotoxins as pharmacological probes of nicotinic acetylcholine receptors. *Acta Pharmacol Sin.* 2009; 30(6): 771-783). Some researches show that the expression of nAChRs of dopaminergic (DA) neuron are drug action targets for treatment of neuropsychological diseases, such as addiction of nicotine, morphine, cocaine, Parkinson's disease, dementia, schizophrenia, depression (Larsson, A.; Jerlhag, E.; Svensson, L.; Soderpalm, B.; Engel, J. A., Is an alpha-conotoxin MII-sensitive mechanism involved in the neurochemical, stimulatory, and rewarding effects of ethanol? *Alcohol* 2004, 34 (2-3), 239-50. Jerlhag, E.; Egecioglu, E.; Dickson, S. L.; Svensson, L.; Engel, J. A., Alpha-conotoxin MII-sensitive nicotinic acetylcholine receptors are involved in mediating the ghrelin-induced locomotor stimulation and dopamine overflow in nucleus accumbens. *European neuropsychopharmacology,* 2008, 18 (7), 508-18). The α-conotoxin-MII capable of blocking α3β2 and α6β2* nAChRs can partially and differentially block dopamine release from striatal synaptosomes, and presynaptic nAChRs contains at least 2 subtypes, i.e., MII-sensitive type and MII-nonsensitive type, that are capable of regulating DA release of dopamine neurons. (Kaiser S A, Soliakov L, Harvey S C, Luetje C W, Wonnacott S. Differential inhibition by α-conotoxin-MII of the nicotinic stimulation of [3H]-dopamine release from rat striatal synaptosomes and slices. J Neurochem 1998; 70: 1069-76). Some new reports show that blocking nAChRs containing α3β4 or α6β2 can effectively prevent onset of smoking addiction and morphine addiction, significantly inhibiting desire for smoking and drug (Brunzell D H, Boschen K E, Hendrick E S, Beardsley P M, McIntosh J M. Alpha-conotoxin MII-sensitive nicotinic acetylcholine receptors in the nucleus accumbens shell regulate progressive ratio responding maintained by nicotine. *Neuropsychopharmacology,* 2010; 35(3):665-673.).

In addition, DA neuron has a very high expression amount of nAChRs containing α6 subunit, and due to the lack of pharmacologic molecular probe specific to α6* nAChRs, the important action mechanism of α6 nAChR in addiction is still not clear. The α6β2*-nAChRs subtype on striate body of mammal brain is considered as drug action target for treatment of smoking addiction and drug addiction (Exley, R.; Clements, M. A.; Hartung, H.; McIntosh, J. M.; Cragg, S. J., Alpha6-containing nicotinic acetylcholine receptors dominate the nicotine control of dopamine neurotransmission in nucleus accumbens. Neuropsychopharmacology 2008, 33 (9), 2158-66). The α6 subtype is not broadly distributed in brain, but enriched in midbrain dopaminergic neuron region, while this region is closely related to happiness, reward and mood control, and this means α6* nAChRs play a vital role in drug addiction and mood control (Yang, K. C., G. Z. Jin, et al. (2009). Mysterious alpha6-containing nAChRs: function, pharmacology, and pathophysiology. Acta Pharmacol Sin 30(6): 740-751. Klink, R.; de Kerchove d'Exaerde, A.; Zoli, M.; Changeux, J. P., Molecular and physiological diversity of nicotinic acetylcholine receptors in the midbrain dopaminergic nuclei. The Journal of neuroscience, 2001, 21 (5), 1452-63. Azam, L.; Winzer-Serhan, U. H.; Chen, Y.; Leslie, F. M., Expression of neuronal nicotinic acetylcholine receptor subunit mRNAs within midbrain dopamine neurons. The Journal of comparative neurology 2002, 444 (3), 260-74. Champtiaux, N.; Gotti, C.; Cordero-Erausquin, M.; David, D. J.; Przybylski, C.; Lena, C.; Clementi, F.; Moretti, M.; Rossi, F. M.; Le Novere, N.; McIntosh, J. M.; Gardier, A. M.; Changeux, J. P., Subunit composition of functional nicotinic receptors in dopaminergic neurons investigated with knock-out mice. The Journal of neuroscience, 2003, 23 (21), 7820-9. Pons, S.; Fattore, L.; Cossu, G.; Tofu, S.; Porcu, E.; McIntosh, J. M.; Changeux, J. P.; Maskos, U.; Fratta, W., Crucial role of alpha4 and alpha6 nicotinic acetylcholine receptor subunits from ventral tegmental area in systemic nicotine self-administration. The Journal of neuroscience, 2008, 28 (47), 12318-27). The α6* nAChRs are also expressed in catecholaminergic nuclei and retina (Le Novere, N.; Zoli, M.; Changeux, J. P., Neuronal nicotinic receptor alpha 6 subunit mRNA is selectively concentrated in catecholaminergic nuclei of the rat brain. The European journal of neuroscience 1996, 8 (11), 2428-39. Vailati, S.; Hanke, W.; Bejan, A.; Barabino, B.; Longhi, R.; Balestra, B.; Moretti, M.; Clementi, F.; Gotti, C., Functional alpha6-containing nicotinic receptors are present in chick retina. Molecular pharmacology 1999, 56 (1), 11-9.). The α6β2* nAChRs show function of regulating dopamine release, and the amount of α6β2* nAChRs significantly decreases in primate animal model of 1-methyl-4-phenyl-1,2,3,6-tetrahydropyridine and human Parkinson's disease model (Champtiaux, N.; Han, Z. Y.; Bessis, A.; Rossi, F. M.; Zoli, M.; Marubio, L.; McIntosh, J. M.; Changeux, J. P., Distribution and pharmacology of alpha 6-containing nicotinic acetylcholine receptors analyzed with mutant mice. The Journal of neuroscience, 2002, 22 (4), 1208-17. Quik, M.; Polonskaya, Y.; Kulak, J. M.; McIntosh, J. M., Vulnerability of 125I-alpha-conotoxin MII binding sites to nigrostriatal damage in monkey. The Journal of neuroscience, 2001, 21 (15), 5494-500. Quik, M.; Bordia, T.; Forno, L.; McIntosh, J. M., Loss of alpha-conotoxin MII- and A85380-sensitive nicotinic receptors in Parkinson's disease striatum. Journal of neurochemistry 2004, 88 (3), 668-79). Hence, α6/α3β2β3 nAChRs-specific blocking agents are valuable tools for studying and explaining physiological functions of α6* nAChRs in different tissues, medicaments for treatment of associated diseases such as addiction, Parkinson's diseases, or tool drugs for screening such medicaments.

New research shows that blocking nAChRs containing α3β4 can effectively prevent onset of smoking addiction, morphine and cocaine addiction, significantly inhibit desire for smoking and drug (Brunzell D H, Boschen K E, Hendrick E S, Beardsley P M, McIntosh J M. Alpha-conotoxin MII-sensitive nicotinic acetylcholine receptors in the nucleus accumbens shell regulate progressive ratio responding maintained by nicotine, Neuropsychopharmacology, 2010, 35(3):665-73).

Surveys show that about ⅙ population suffer pains, including arthritis, neuralgia, sore pain, in which neuralgia affects 4-8% of population, and neuralgia may be caused by alcoholism, ischioneuralgia, cancers and cancer chemotherapy, diabetes mellitus, prosopalgia, sclerosis, herpes zoster, mechanical injury. The nAChRs containing α3-subunit, including α3β2 and α3β4 subtypes, are mainly expressed in peripheral nervous system, and also distributed in central nervous system, and are targets for action of neuralgic medicines. The α-conotoxin capable of blocking α3β2 or α3β4 nAChRs shows excellent analgesic activity to many chronic pains in clinic, and is not addicted. Chronic pains are a health challenge worldwide, and in urgent need of new therapeutic drugs (Napier, I. A.; Klimis, H.; Rycroft, B. K.; Jin, A. H.; Alewood, P. F.; Motin, L.; Adams, D. J.; Christie, M. J., Intrathecal α-conotoxins Vc1.1, AuIB and MII acting on distinct nicotinic receptor subtypes reverse signs of neuropathic pain. Neuropharmacology 2012, 62 (7), 2202-2207. Blyth, F. M.; March, L. M.; Brnabic, A. J.; Jorm, L. R.; Williamson, M.; Cousins, M. J., Chronic pain in Australia: a prevalence study. PAIN 2001, 89 (2-3), 127-34. Cousins, M. J.; Brennan, F.; Carr, D. B., Pain relief: a universal human right. PAIN 2004, 112 (1-2), 1-4. Eisenberg, E.; McNicol, E. D.; Carr, D. B., Efficacy and safety of opioid agonists in the treatment of neuropathic pain of nonmalignant origin: systematic review and meta-analysis of randomized controlled trials. JAMA: the journal of the American Medical Association 2005, 293 (24), 3043-52.).

The α3β4 nAChRs are main acetylcholine receptor subtypes in sensory and autonomic nerve centers. The α3β4 nAChRs are also branches of central nervous system (CNS) neurons, such as habenula extended to central and back marrow, and relate to addiction of nicotine and other abuse drugs (Millar, N. S.; Gotti, C., Diversity of vertebrate nicotinic acetylcholine receptors. Neuropharmacology 2009, 56 (1), 237-46; Tapper, A. R.; McKinney, S. L.; Nashmi, R.; Schwarz, J.; Deshpande, P.; Labarca, C.; Whiteaker, P.; Marks, M. J.; Collins, A. C.; Lester, H. A., Nicotine activation of alpha4* receptors: sufficient for reward, tolerance, and sensitization. Science 2004, 306 (5698), 1029-32.). The α3β4 nAChR relates to limbic dopamine pathways, and plays very important role to reward effects generated by abuse substances (such as drugs). In β4-subunit knockout mice, the motion and reward effects caused by nicotine decrease significantly, which suggests the important effects of α3β4 nAChR on nicotine addiction in CNS (Sales, R., Sturm, R., Boulter, J., and De Biasi, M. (2009) Nicotinic receptors in the habenulo-interpeduncular system are necessary for nicotine withdrawal in mice. J. Neurosci. 29, 3014-3018). The α3β4 nAChRs also play a very important role in threatening response, and significantly affect the regulation of glutamic acid and the release of noradrenaline (Zhu, P. J.; Stewart, R. R.; McIntosh, J. M.; Weight, F. F., Activation of nicotinic acetylcholine receptors increases the frequency of spontaneous GABAergic IPSCs in rat basolateral amygdala neurons. Journal of neurophysiology 2005, 94 (5), 3081-91. Alkondon, M.; Albuquerque, E. X., A non-alpha7 nicotinic acetylcholine receptor modulates excitatory input to hippocampal CA1 interneurons. Journal of neurophysiology 2002, 87 (3), 1651-4. Luo, S.; Kulak, J. M.; Cartier, G. E.; Jacobsen, R. B.; Yoshikami, D.; Olivera, B. M.; McIntosh, J. M., alpha-conotoxin AuIB selectively blocks alpha3 beta4 nicotinic acetylcholine receptors and nicotine-evoked norepinephrine release. The Journal of neuroscience: the official journal of the Society for Neuroscience 1998, 18 (21), 8571-9. Kulak, J. M.; McIntosh, J. M.; Yoshikami, D.; Olivera, B. M., Nicotine-evoked transmitter release from synaptosomes: functional association of specific presynaptic acetylcholine receptors and voltage-gated calcium channels. Journal of neurochemistry 2001, 77 (6), 1581-9.).

The α-CTxs having extraordinary selectivity to specific subtypes of nAChRs are necessary tools for studying distribution and functions of various subtypes and medicaments for treatment of associated diseases (Kasheverov, I. E., Utkin, Y. N., and Tsetlin, V. I. (2009) Naturally Occurring and Synthetic Peptides Acting on Nicotinic Acetylcholine Receptors. Current Pharmaceutical Design 15, 2430-2452; Nicke, A., Wonnacott, S., and Lewis, R. J. (2004) alpha-Conotoxins as tools for the elucidation of structure and function of neuronal nicotinic acetylcholine receptor subtypes. Eur. J. Biochem. 271, 2305-2319). The α-CTx being capable of specifically blocking α3β2 subtype, while having very small or even no activity of blocking very similar α6β2* subtype is very valuable, that is a ligand capable of distinguishing α3β2 and α6β2* subtypes has very important scientific and application value. The reason is that α6β2* subtype dominates dopaminergic region. Our knowledge about composition, properties and physiological functions of receptors in this important physiological region are merely from application of α-CTx MII, while α-CTx MII has poor selectivity to α3β2 and α6β2* subtypes, and cannot distinguishes them; or they are studied using selective blocking agents for α6β2* subtypes (Dowell, C., Olivera, B. M., Garrett, J. E., Staheli, S. T., Watkins, M., Kuryatov, A., Yoshikami, D., Lindstrom, J. M., and McIntosh, J. M. (2003) α-Conotoxin PIA Is Selective for 6 Subunit-Containing Nicotinic Acetylcholine Receptors. The Journal of Neuroscience 23, 8445-8452; McIntosh, J. M., Azam, L., Staheli, S., Dowell, C., Lindstrom, J. M., Kuryatov, A., Garrett, J. E., Marks, M. J., and Whiteaker, P. (2004) Analogs of alpha-conotoxin MII are selective for alpha 6-containing nicotinic acetylcholine receptors. Molecular pharmacology 65, 944-952; Quik, M., Perez, X. A., and Grady, S. R. (2011) Role of alpha 6 nicotinic receptors in CNS dopaminergic function: relevance to addiction and neurological disorders. *Biochemical pharmacology* 82, 873-882; Letchworth, S. R., and Whiteaker, P. (2011) Progress and challenges in the study of alpha 6-containing nicotinic acetylcholine receptors. *Biochemical pharmacology* 82, 862-872; Champtiaux, N., Gotti, C., Cordero-Erausquin, M., David, D. J., Przybylski, C., Lena, C., Clementi, F., Moretti, M., Rossi, F. M., Le Novere, N., McIntosh, J. M., Gardier, A. M., and Changeux, J. P. (2003) Subunit composition of functional nicotinic receptors in dopaminergic neurons investigated with knock-out mice. *Journal of Neuroscience* 23, 7820-7829). However, the expression of α3β2* nAChRs usually results in expression interlapping of α6β2* nAChRs, and α3β2* nAChRs are sometimes dominant (Whiteaker, P., McIntosh, J. M., Luo, S. Q., Collins, A. C., and Marks, M. J. (2000) I-125-alpha-conotoxin MII identifies a novel nicotinic acetylcholine receptor population in mouse brain. *Molecular pharmacology* 57, 913-925; Whiteaker, P., Peterson, C. G., Xu, W., McIntosh, J. M., Paylor, R., Beaudet, A. L., Collins, A. C., and Marks, M. J. (2002) Involvement of the alpha 3 subunit in central nicotinic binding populations. *Journal of Neuroscience* 22, 2522-2529; McClure-Begley, T. D., Wageman, C. R., Grady, S. R., Marks, M. J., McIntosh, J. M., Collins, A. C., and Whiteaker, P. (2012) A novel alpha-conotoxin MII-sensitive nicotinic acetylcholine receptor modulates H-3-GABA release in the superficial layers of the mouse superior colliculus. *J Neurochem* 122, 48-57). In addition, α3β2* nAChRs in spine also play an important role in transmission of pain stimulation and are analgesic action targets (Young, T., Wittenauer, S., McIntosh, J. M., and Vincler, M. (2008) Spinal α3β2* nicotinic acetylcholine receptors tonically inhibit the transmission of nociceptive mechanical stimuli. *Brain research* 1229, 118-124). Thus, finding a real α3β2* vs. α6β2* nAChRs selective blocking agent has very important value to comprehensively studying and understanding the functions and meanings of the subtype under normal and disease states.

It can be seen that α-conotoxins have tremendous potency for developing new medicines for treatment of pains, smoking cessation, rehabilitation, treatment of Parkinson's disease, dementia, depression and schizophrenia, and for studying mechanisms of associated diseases, and molecular probe tool drugs for distinguishing specific nAChRs subtypes as well as inventive drugs for treatment of neuralgia and addiction are also in urgent need to relieve damage and serious social problems caused by pains, smoking addiction and drug addiction. At present, it is still in urgent need to develop new nAChRs blocking agents with high specificity.

Contents of the Invention

After intensive study and creative efforts, the inventors of the present invention find a new type of α-conotoxin peptides, which can specifically block acetylcholine receptor, especially have strong activity of blocking a neuralgic drug target α3β2 nAChRs, α3β4 nAChRs or α6/α3β4 nAChRs, and an addictive drug target α6/α3β2β3 nAChRs or α3β4 nAChRs, and show very potent analgesic activity in animal models, so have good application prospect in aspects of manufacturing a medicament for analgesia, smoking cessation and rehabilitation, preventing and treating depression, dementia, schizophrenia, Parkinson's disease, or using as neuroscientific tool drugs. Thus, the following invention is provided:

One aspect of the present invention relates to a peptide, which has an amino acid sequence as shown in Formula I:

$GCCSX_1PX_2CX_3X_4X_5X_6PX_7X_8CX_9$ (SEQ ID NO: 68)     Formula I wherein,
$X_1$ represents D or H,
$X_2$ represents P, A or V,
$X_3$ represents R, N or S,
$X_4$ represents N, V or A,
$X_5$ represents K, D, M or A,
$X_6$ represents H or S,
$X_7$ represents D, E or $X_7$ is absent,
$X_8$ represents L or I,
$X_9$ represents G or $X_9$ is absent;
optionally, the C-terminal of the polypeptide of Formula I is amidated.

The above amino acids D, H, P, A, V, R, N, S, K, M, H, E, L, I, G are abbreviations of amino acids, which have the meanings well known by those skilled in the art.

The amidation of C-terminal of the polypeptide of Formula I can also be represented by #, i.e., $GCCSX_1PX_2CX_3X_4X_5X_6PX_7X_8CX_9\#$. (SEQ ID NO: 68)

The present invention further relates to a polypeptide, which is or comprises the amino acid sequence of any one of the following items (1) to (3):

(1) an amino acid sequence as shown in any one of sequences of SEQ ID NO: 3, SEQ ID NO: 4, SEQ ID NO: 6, SEQ ID NO: 11-15, SEQ ID NO: 26-28 or SEQ ID NO: 30;

(2) an amino acid sequence having at least 80%, preferably at least 85%, more preferably at least 90%, especially preferably at least 95%, most preferably at least 97% identity with the amino acid sequence of (1); or (3) an amino acid sequence different from the sequence of (1) or (2) in substitution, deletion, insertion and/or addition of 1-5, preferably 1-3, more preferably 1-2, most preferably 1 amino acid residue.

For one purpose of the present invention, identity of two or more amino acid sequences is determined by BLAST2.0 Protein Database Query Program (Aaltschul et al., 1997, Nucleic Acid Research 25: 3389-3402) using the following parameters: blastall -p blastp-a4-e10-E0-v500-b250-I [query document]-d prot_all, in which -p refers to the name of program, -a refers to number of servers, -e refers to expectancy value, -E refers to cost of extension gap, -v refers to number of one-line description, -b refers to comparison number to be displayed, -I refers to query document, -d refers to database used for query.

The differences between the amino acid sequence of homologic polypeptide and amino acid sequence of any one of SEQ ID NO: 3, SEQ ID NO: 4, SEQ ID NO: 6, SEQ ID NO: 11-15, SEQ ID NO: 26-28 or SEQ ID NO: 30 may lie in substitution, insertion addition and/or deletion of 1 or more, preferably 1-5, more preferably 1-3, especially preferably 1-2, most preferably 1 amino acid residue. Preferably, the change of amino acid is a change having little effect on the property, i.e., it is a conservative amino acid substitution, a deletion of small fragment which usually is a deletion of 1 to about 5, preferably 1-3, more preferably 1 amino acid, a small amino or carboxyl terminal extension such as a methionine residue added to amino terminal, a small linker peptide having up to about 20-25 residues; or a small extension contributing to purification via changing net charge or other function such as polyhistidine fragment, epitope, binding domain, all of which do not significantly affect folding and/or activity of protein.

An example of conservative substitution is a substitution within basic amino acids (arginine, lysine, and histidine), acidic amino acids (glutamic acid and aspartic acid), polar amino acids (glutamine and asparagine), hydrophobic amino acids (leucine, isoleucine and valine), aromatic amino acids (phenylalanine, tryptophane and tyrosine), and small amino acids (glycine, alanine, serine, threonine and methionine). The amino acid substitutions usually not changing specific activity are known in the art, and are described in, for example, "Proteins", H. Neurath and R. L. Hill, 1979, Academic Press, New York. The commonest substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, etc., and reversely performed substitutions.

The present invention further comprises fused polypeptides or lysable fused polypeptides in which the N-terminal and/or C-terminal of α-conotoxin is fused with other peptide/polypeptide. The technology for generating fused polypeptides is known in the art, comprising linking a coding sequence coding the peptide of the present invention with a coding sequence coding the other peptide/polypeptide so that they are in one reading frame and the expression of the fused polypeptide is controlled by the same promoter and terminator.

The polypeptide according to any one of items of the present invention preferably has an amino acid sequence as shown in SEQ ID NO: 4 (α-LvIA/LvD21), or SEQ ID NO: 3 (this peptide is actually a propeptide of α-LvIA/LvD21).

In the polypeptide according to any one of items of the present invention, the C-terminal of the polypeptide is preferably amidated. The amidation can be carried out via artificial chemical synthesis, or via an amidation enzyme in vivo or in vitro.

In the polypeptide according to any one of items of the present invention, preferably, the $1^{st}$ cysteine and the $3^{rd}$ cysteine of the N-terminal of the polypeptide form a disulfide bond, and the $2^{nd}$ cysteine and the $4^{th}$ cysteine form a disulfide bond; or the $1^{st}$ cysteine and the $4^{th}$ cysteine of the N-terminal of the polypeptide form a disulfide bond, and the $2^{nd}$ cysteine and the $3^{rd}$ cysteine form a disulfide bond; or the $1^{st}$ cysteine and the $2^{nd}$ cysteine of the N-terminal of the polypeptide form a disulfide bond, and the $3^{rd}$ cysteine and the $4^{th}$ cysteine form a disulfide bond.

The polypeptide of the present invention is conotoxin; specifically, α-conotoxin.

The conotoxin can be extracted from *Conus lividus* or *Conus textile* produced in Hainan Province of China; or can be an amino acid of chemical synthesis (e.g., the methods of Examples 2-(1) to 2-(3)); or a polypeptide obtained by expressing its nucleotide via genetic recombination (the nucleotide sequence can be prepared by the methods of Examples 1-(1) to 1-(3) or by the methods for direct polypeptide artificial synthesis of Examples 2-(1) to 2-(3)); or by referring to the following method:

Another aspect of the present invention relates to a method for preparing the polypeptides of any one of items of the present invention, comprising the following steps:

1) synthesizing a linear polypeptide by ABI Prism 433a polypeptide synthesizer or by manual method, in which side-chain protecting groups of Fmoc amino acid are: Pmc (Arg), Trt or Acm (Cys), But (Thr, Ser, Tyr), OBut (Asp) and Boc (Lys);

2) cutting the linear polypeptide synthesized in step 1) from resin;

3) using glacial diethyl ether to precipitate and wash the linear polypeptide obtained in step 2), and recovering a crude product of linear polypeptide;

4) using a preparative reversed phase HPLC C18 column (Vydac) to purify the crude product of linear polypeptide obtained in step 3);

5) subjecting the product obtained in step 4) to two- or one-step oxidative folding.

Another aspect of the present invention relates to a polynucleotide which codes an amino acid sequence of the polypeptide of any one of items of the present invention.

Preferably, the polynucleotide of any one of items of the present invention is or comprises a nucleotide sequence selected from any one of the following items (1) to (3):

(1) a nucleotide sequence as shown in any one of sequences of SEQ ID NO: 1, SEQ ID NO: 2, SEQ ID NO: 5, SEQ ID NO: 7, SEQ ID NO: 8, SEQ ID NO: 16-21, SEQ ID NO: 22-25, SEQ ID NO: 29 or SEQ ID NO: 31;

(2) a complementary sequence of the nucleotide sequence of (1);

(3) a nucleotide sequence capable of hybridizing with the nucleotide sequence of (1) under a stringent condition.

As for hybridization between polynucleotides, reference can be made to many documents in the art, including, for example, Molecular Cloning: A Laboratory Manual, Edition 2, Sambrook, etc., Cold Spring Harbor Laboratory Press, Cold Spring, 1989. The hybridization can use stringent conditions of various degrees, for example, moderately stringent conditions, moderately-highly stringent conditions, or highly stringent conditions. The more stringent the conditions are, the higher complementary degree required for forming double helix. The stringent degree can be controlled via temperature, probe concentration, probe length, ion strength, time, etc. For double-stranded DNA, the hybridization is performed at a temperature 20-25° C. lower than the melting temperature [Tm] of DNA heterozygote in 6×SSPE, 5×Denhardt's solution, 0.1% SDS, 0.1 mg/ml denatured DNA overnight. The washing is usually performed as follows: at Tm-20° C. in 0.2×SSPE, 0.1% SDS, once, 15 minutes (washing under moderately stringent condition).

Another aspect of the present invention relates to a nucleic acid construct, which comprises the polynucleotide of any one of items of the present invention.

Another aspect of the present invention relates to an expression vector, which comprises the nucleic acid construct of the present invention.

Another aspect of the present invention relates to a transformed cell, which comprises the expression vector of the present invention.

Another aspect of the present invention relates to a fused protein, which comprises the polypeptide of any one of items of the present invention.

Another aspect of the present invention relates to a pharmaceutical composition, which comprises the polypeptide of any one of items of the present invention, or the fused protein of the present invention; optionally, which further comprises a pharmaceutically acceptable carrier or excipient.

Another aspect of the present invention relates to a method for blocking acetylcholine receptor, comprising the step of using an effective amount of the polypeptide or fused protein of any one of items of the present invention; specifically, said acetylcholine receptor is α3β2 acetylcholine receptor, α6/α3 β2β3 acetylcholine receptor or α3β4 acetylcholine receptor.

Another aspect of the present invention relates to a method for screening an inhibitor of an acetylcholine receptor or determining the subtype of an acetylcholine receptor, the method comprising: the step of contacting an acetylcholine receptor with the polypeptide or fused protein of any one of items of the present invention in the presence or absence of a candidate compound; specifically, said acetylcholine receptor is α3β2 acetylcholine receptor, α6/α3β2β3 acetylcholine receptor or α3β4 acetylcholine receptor. When the polypeptide or fused protein can specifically block α3β2 acetylcholine receptor (e.g., α-conotoxin LvIA/LvD21), can specifically block α6/α3β2β3 acetylcholine receptor (e.g., α-conotoxin TxIB/Txd4) r, or can specifically block α3β4 acetylcholine receptor (e.g., α-conotoxin TxIC/Txd1), it can be determined that the acetylcholine receptor is α3β2 subtype, α6β2* subtype (α6/α3β2β3 acetylcholine receptor) or α3β4 subtype acetylcholine receptor.

Another aspect of the present invention relates to a use of the polypeptide or fused protein of any one of items of the present invention in blocking acetylcholine receptor; specifically, the acetylcholine receptor is α3β2 acetylcholine receptor, α6/α3β2β3 acetylcholine receptor or α3β4 acetylcholine receptor.

Another aspect of the present invention relates to a use of the polypeptide or fused protein of any one of items of the present invention in the manufacture of a medicament or reagent for blocking acetylcholine receptor; specifically, said acetylcholine receptor is α3β2 acetylcholine receptor, α6/α3β2β3 acetylcholine receptor or α3β4 acetylcholine receptor.

Another aspect of the present invention relates to a use of the polypeptide or fused protein of any one of items of the present invention in the manufacture of a medicament for treatment and/or prophylaxis and/or adjuvant therapy of a nervous system disease, such as addiction, neuralgia, Parkinson's disease, or dementia, or a use in the manufacture of a drug for killing a pest, analgesia, smoking cessation, or addiction treatment; specifically, said neuralgia is induced by the following causes: cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, lymphatic neuralgia, myeloma, multipoint motor neuralgia, chronic congenital esthesioneurosis, acute spontaneous neuralgia, squeezing neuralgia, angiitis, vasculitis, ischemia, uremia, children biliary liver disease, chronic respiratory disorder, complex neuralgia, multiple organ failure, sepsis/pyaemia, hepatitis, *porphyria*, avitaminosis, chronic liver diseases, primary biliary cirrhosis, hyperlipidemia, leprosy, Lyme arthritis, sensory perineuritis, allergies, etc.

Another aspect of the present invention relates to a method for treatment and/or prophylaxis and/or adjuvant therapy of nervous system diseases, such as pains, addiction of tobacco, alcohol and drugs, dementia, schizophrenia, central nerve disorder, epilepsy, Parkinson's disease, mental disorder, neuromuscular blockade, myasthenia gravis, depression, hypertension, arrhythmia, asthma, muscular flaccidity, apoplexy, breast cancer and lung cancer, or a method for killing a pest, analgesia, smoking cessation, or addiction treatment, comprising the step of administering an effective amount of the polypeptide (conotoxin peptide or propeptide thereof) or fused protein of the present invention or the pharmaceutical composition of the present invention; specifically, said addiction is induced by addictive substance such as nicotine, morphine, cocaine, alcohol; the neuralgia is induced by the following reasons: cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, lymphatic neuralgia, myeloma, multipoint motor neuralgia, chronic congenital esthesioneurosis, acute spontaneous neuralgia, squeezing neuralgia, angiitis, vasculitis, ischemia, uremia, children biliary liver disease, chronic respiratory disorder, complex neuralgia, multiple organ failure, sepsis/pyaemia, hepatitis, *porphyria*, avitaminosis, chronic liver diseases, primary biliary cirrhosis, hyperlipidemia, leprosy, Lyme arthritis, sensory perineuritis, allergies, etc.

The conotoxin peptide of the present invention can exert effects by binding α3β2 acetylcholine receptor (nAChR), α6/α3β2β3 acetylcholine receptor or α3β4 acetylcholine, have analgesia effect, can be used for studying, diagnosis and treatment nervous system diseases such as addiction, neuralgia, Parkinson's disease, dementia, schizophrenia, depression, and as a useful molecular probe in studying. Affinity of different α-CTx to vertebrate receptor is diverse, for example, in several orders of magnitude. Such diversity among germ lines makes α-CTx be useful as a probe for studying phylogenesis of vertebrates, or be useful as a molecular probe for determining different subtypes of nAchRs. They are candidate drugs, primary drugs and therapeutic drugs in developing new drugs.

The terms used in the present invention are explained as follows.

Neuralgia

The polypeptide of the present invention relates to a use for treatment of various neuralgias. Neuralgia is a pain caused by a primary or secondary lesion or a functional disorder or a transient disorder of peripheral or central nervous system, manifesting in spontaneous pain, sense hypersensitivity, etc. Neuralgia may be caused by many diseases, including cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, myeloma, multipoint neuralgia, chronic congenital esthesioneurosis, acute fierce spontaneous neuralgia, squeezing neuralgia, angiitis (vasculitis)/ischemia, uremia, children biliary liver disease, chronic respiratory disorder, complex neuralgia, multiple organ failure, sepsis/pyaemia, hepatitis, *porphyria*, avitaminosis, chronic liver diseases, primary biliary cirrhosis, hyperlipidemia, leprosy, Lyme arthritis, sensory perineuritis, allergies, etc.

Addiction

The polypeptide of the present invention relates to treatment of addiction caused by various dependent substances. Addiction refers to a periodical or chronic poisoning state of a subject who repeatedly uses a psychoactive substance. The psychoactive substance refers to nicotine, opium, heroine, methylamphetamine (ice), morphine, marihuana, cocaine, and other narcotics and psychotropic substances that can cause addiction in human and are controlled by national regulations. Addiction relates to the generation of a great amount of dopamine, exhibiting uncontainable use of a favorite substance or a use behavior that can hardly be restrained or rectified, and unscrupulously using any means to obtain psychoactive substances for acquiring good feel or avoiding withdrawal symptoms. Typical situations are increase of resistance and occurrence of withdrawal symptoms. The life of addict is totally mastered by the addictive substance and thus is seriously affected, and even rejects other important action and all responsibility. Hence, the use of addictive substance would bring bout damage to both individual and society. When using with alcohol, addiction is equivalent to chronic alcoholism. The term "addiction" also covers both physical and psychological contents. Psychological addiction emphasizes control impaired experience in alcohol drinking and drug administration, while physical addiction refers to resistance and withdrawal symptoms.

Nucleic Acid Construct

The present invention further relates to a nucleic acid construct comprising the nucleic acid sequence of the present invention and 1 or more regulatory sequences operably linked thereto, in which the regulatory sequences under compatible conditions thereof can guide an encoding sequence to express in a suitable host cell. The expression should be understood to comprise any steps relating to produce polypeptide, including but not limited to transcription, modification after transcription, translation, modification and secretion after translation.

In the text, "nucleic acid construct" is defined as a single chain or double chain nucleic acid molecule, which is separated from natural gene, or comprises nucleic acid fragments combined and collocated in non-natural manner via modification. When the nucleic acid construct comprises all regulatory sequences necessary for expressing the coding sequence of the present invention, the term "nucleic acid construct" has the same meaning of expression kit. In the text, the term "coding sequence" is defined as a part of nucleic acid sequence for directly determining amino acid sequence of protein product. The boundaries of coding sequence usually are determined with ribosome bind site (corresponding to prokaryotic cell) closely adjacent to mRNA 5' terminal open reading frame upstream and transcription termination sequence closely adjacent to mRNA 3' terminal open reading frame downstream. Coding sequence can comprise but is not limited to DNA, cDNA and recombinant nucleic acid sequence.

The separated nucleic acid sequence encoding the peptide of the present invention can be manipulated in many manners so as to express the peptide. Depending on expression vector, the nucleic acid sequence can be processed before insertion into the vector if necessary. The technology of modifying nucleic acid sequence using recombinant DNA method is well known in the art.

The term "regulatory sequences" in the text is defined as all components necessary for or contributive to the expression of the peptide of the present invention. Each regulatory sequence naturally exists in or is extraneously added to the nucleic acid sequence coding the polypeptide. These regulatory sequences include but are not limited to leader sequences, polyadenylate sequences, propeptide sequences, promoters, signal sequences and transcription terminators. The lowest limit is that the regulatory sequences should comprise promoters and termination signals for transcription and translation. In order to introduce a specific restriction site to link the regulatory sequence to the coding region of nucleic acid sequence coding the polypeptide, a regulatory sequence with a connector can be provided. The term "operably linking" in the text refers to a conformation in which the regulatory sequence is at a suitable position of coding sequence corresponding to DNA sequence so that the regulatory sequence guides the expression of the polypeptide.

The regulatory sequence can be any suitable promoter sequence, i.e., a nucleic acid sequence that can be recognized by a host cell expressing nucleic acid sequence. The promoter sequence comprises a transcriptional regulatory sequence mediating polypeptide expression. The promoter can be any nucleic acid sequence having transcription activity in a selected host cell, including mutant, truncated and hybridized promoters, and can be obtained from a gene coding extracellular or intracellular polypeptide homologous or heterogeneous to host cell.

The regulatory sequence can further be a suitable transcription termination sequence, i.e., a sequence capable of being recognized by a host cell so as to terminate transcription. The termination sequence is operably linked to 3' terminal of the nucleic acid sequence coding the polypeptide. Any terminators having such function in a selected host cell can be used in the present invention.

The regulatory sequence can further be a suitable leader sequence, i.e., a mRNA untranslated region very important for translation of host cell. The leader sequence is operably linked to 5' terminal of the nucleic acid sequence coding the polypeptide. Any leader sequence capable of exerting the function in a selected host cell can be used in the present invention.

The regulatory sequence can further be a coding region of signal peptide, and the region codes an amino acid sequence linked to amino terminal of polypeptide, and can lead the coded polypeptide into cell secretion route. The 5' terminal of coding region of nucleic acid sequence can naturally contain a signal peptide coding region consistent to translation reading frame and naturally linked to a coding region of secreted polypeptide. Or, the 5' terminal of coding region can contain extraneous signal peptide coding region relative to the coding sequence. When the coding sequence does not contain signal peptide coding region under normal condition, an extraneous signal peptide coding region may be added. Or, an extraneous signal peptide coding region can be used to simply substitute a natural signal peptide coding region so as to enhance secretion of polypeptide. However, any signal peptide coding region capable of leading an expressed polypeptide to enter into a secretion route of a used host cell can be used in the present invention.

The regulatory sequence can further be a propeptide coding region, and the region codes an amino acid sequence at amino terminal of polypeptide. The obtained polypeptide is called as proenzyme or propolypeptide. The propolypeptide usually has not activity, and can be transformed into a mature active polypeptide by cutting propeptide from propolypeptide via catalysis or self-catalysis.

When the amino terminal of polypeptide has both signal peptide and propeptide, the propeptide is close to the amino terminal of polypeptide, while the signal peptide is close to the amino terminal of the propeptide.

It may also be necessary to add a regulatory sequence capable of regulating polypeptide expression according to growth conditions of host cells. Examples of regulatory system are systems capable of responding to a chemical or physical stimulation (included in a condition having a regulatory compound) so as to open or close gene expression. Other examples of the regulatory sequence are regulatory sequences capable of amplifying gene. In these examples, the nucleic acid sequence coding polypeptide should be operably linked to the regulatory sequence.

Expression Vector

The present invention further relates to a recombinant expression vector comprising the nucleic acid sequence of the present invention, a promoter and a terminal signal for transcription and translation. The above nucleic acids and regulatory sequences could be linked together to prepare a recombinant expression vector, and the vector can comprise 1 or more convenient restriction sites so that the nucleic acid sequence coding the polypeptide can be inserted or substituted at these sites. Or, the nucleic acid sequence or a nucleic acid construct comprising the sequence can be inserted into a suitable expression vector to express the nucleic acid sequence of the present invention. When the expression vector is prepared, the coding sequence can be in the vector so as to operably link to a suitable expression regulatory sequence.

The recombinant expression vector can be any vector (e.g., plasmid or virus) capable of performing recombinant DNA operation and expressing nucleic acid. The selection of vector usually depends on compatibility of vector and host cell into which the vector is introduced. The vector can be a linear or closed plasmid.

The vector can be an autonomously replicating vector (i.e., an extrachromosomal complete construct, which can be replicated independent of chromosome), such as plasmid, extrachromosomal component, minute chromosome, or artificial chromosome. The vector can comprise any mechanism ensuring self-replication. Or, the vector is a vector that is integrated into genome and replicated together with the chromosome into which it is integrated when the vector is introduced into a host cell. In addition, the used vector can be a single vector or plasmid, or generally contained 2 or more vectors or plasmids of total DNA to be introduced into host cell genome, or a transposon.

Preferably, the vector of the present invention comprises 1 or more selective markers convenient for selecting transformed cells. The selective marker is such a gene which product provides a resistance against a biocide, a resistance against a heavy metal, or provides an auxotroph prototrophy. Examples of bacterial selective markers are daI gene of bacillus subtilis or bacillus licheniformis, or resistance makers including antibiotics such as ampicillin, kanamycin, chloromycetin, or tetracycline.

Preferably, the vector of the present invention comprises components ensuring the vector to be stably integrated into genome of host cell, or ensuring the vector to be autonomously replicated independent to cell genome in cell.

As to autonomous replication, the vector can further comprise a replication organ so that the vector can be autonomously replicated in host cell. The replication organ can have a mutation that makes it a temperature-sensitive type in the host cell (see: for example, fEhrlich, 1978, National Academy of Sciences, 75:1433).

More than one copy of the nucleic acid sequence of the present invention can be inserted into a host cell to increase the output of gene product. The number of copies of the nucleic acid sequence can be increased by inserting at least one additional copy of the sequence into genome of host cell, or by inserting the nucleic acid sequence together with an amplification selective marker, culturing cells in the presence of a suitable selective reagent, picking out cells that have selective marker gene for copy amplification and thus have additional copies of the nucleic acid.

The steps for linking the above components to construct the recombinant expression vector of the present invention are well known in the art (see: for example, Molecular Cloning: A Laboratory Manual, Edition 2, Sambrook, etc., Cold Spring Harbor Laboratory Press, Cold Spring, 1989).

Host Cells

The present invention further relates to a recombinant host cell comprising the nucleic acid sequence of the present invention for recombination production of polypeptide. A vector comprising the nucleic acid sequence of the present invention can be introduced into a host cell so that the vector is maintained in form of the above chromosomal integrated body or self-replicable extrachromosomal vector. The term "host cell" covers any offspring that are different from parent cells due to mutation during replication period. The selection of host cell mainly depends on polypeptide coding gene and source thereof.

The host cell can be a prokaryotic cell or an eukaryotic cell, for example, a bacterium or yeast cell. The vector can be introduced into the host cell by a technology well known in the art.

Preparation Method

The present invention further relates to a method for recombination production of the peptide of the present invention, the method comprising: (a) culturing a host cell having a nucleic acid construct under conditions suitable to produce the peptide, the nucleic acid construct comprising a nucleic acid sequence encoding the peptide; and (b) recovering the peptide.

In the preparation method of the present invention, the cell is cultured in a nutrient medium suitable for polypeptide production by a method known in the art. For example, the cell is cultured by shake-flask culture, laboratory culture, small or large scale fermentation in industrial fermentation tank (including continuous, batch, batch charging or solid state fermentation) in a suitable culture medium under conditions allowing polypeptide expression and/or separation. The culture can be carried out with steps known in the art in a suitable culture medium containing carbon source and nitrogen source and inorganic salt. The suitable culture medium can be provided by suppliers or prepared according to a composition known in the art (for example, those in the catalogue of American Type Culture Collection). If the polypeptide is secreted in the culture medium, the polypeptide can be directly recovered from the culture medium. If the polypeptide is not secreted, it can be recovered from cell lysate.

The produced polypeptide can be recovered by a method known in the art. For example, the polypeptide can be recovered from the culture medium by conventional steps (including but not limited to centrifugation, filtration, spray drying, evaporation or precipitation).

The polypeptide of the present invention can be purified by known steps in the art, and these steps include but are not limited to chromatography (e.g., ion exchange chromatography, affinity chromatography, hydrophobic interaction chromatography, chromatofocusing, and size exclusion chromatography), HPLC, electrophoresis (e.g., preparative isoelectric focusing), differential solubility (e.g., ammonium sulfate precipitation), SDS-PAGE or extraction (see: for example, Protein Purification, edited by J. C. Janson and Lars Ryden, VCH Publishers, New York, 1989).

Transgenic Animals and Plants

The present invention further relates to an animal or plant cell transformed with the nucleic acid sequence of the present invention, preferably a plant cell of wheat, maize, so as to give the transformed host a new property (e.g., pest resistance). This can be fulfilled by transforming the animal or plant cell with the construct disclosed in the present invention by a method well known in the art.

Method and Preparation for Controlling Pests

Many methods known by those skilled in the art can be used for controlling pests with the conotoxin peptide or polynucleotide of the present invention. These methods comprise, for example, applying a recombinant microorganism to pests (or their locus), and transforming a plant with a gene encoding the conotoxin peptide of the present invention. The transformation can be carried out by conventional methods known by those skilled in the art. Necessary substances for such transformation are disclosed here or can be readily obtained via other routes by those skilled in the art.

The preparation containing the conotoxin peptide or the recombinant microorganism of the polynucleotide of the present invention can be applied to soil. The prepared product can further be used for seed coating or root treatment or application on whole plant in later period of plant growth cycle. The preparation can comprise a diffusion-thickening adjuvant, a stabilizing agent, other pesticide additives, or a surfactant. A liquid preparation can be aqueous or nonaqueous, and used in form of foam, gel, suspension, emulsible concentrate. Components can comprise rheological agents, surfactants, emulsifying agents, dispersing agents, or polymers.

Those skilled in the art understand that pesticide can have a widely variable concentration due to nature of specific preparations, especially, it can be a concentrate or directly used. Pesticide can be in an amount of at least 1% by weight, or 100% by weight. Dry preparation usually has about 1-95% by weight of pesticide, while liquid preparation usually has a solid content of about 1-60% by weight in liquid phase. A preparation containing cells usually have about $10^2$ to about $10^4$ cells/mg. These preparations can be applied in an amount of 50 mg (liquid or dry) to 1 kg per hectare. The preparations can be applied to pest environment such as soil and plant by spraying, scattering, splashing.

Pharmaceutical Composition

The present invention further relates to a pharmaceutical composition comprising the peptide of the present invention and a pharmaceutically acceptable carrier and/or excipient. The pharmaceutical composition can be used for studying, diagnosis, alleviation or treatment of diseases or disorders relating to addiction, neuralgia, mental retardation, pain, Parkinson's disease, mental disorders, depression, myasthenia gravis, cancers, etc. In an embodiment, a pharmaceutical composition comprising a therapeutically effective amount of the peptide of the present invention is prepared and administered in a way facilitating medicinal application, while clinical state of individual patient, delivery site, administration method, administration schedule and other factors known by doctor should also be considered. Thus, "effective amount" for the purpose in the text is determined with consideration in these aspects.

A pharmaceutical composition comprising a therapeutically effective amount of the peptide of the present invention can be administered parenterally, orally, intracisternally, intrathecally. "Pharmaceutically acceptable carrier" refers to a nontoxic solid, semi-solid or liquid filler, diluent, capsule material or any type of formula assistants. The term "parenterally" in the text refers to administration manners including intravenous, intramuscular, intraperitoneal, intrathoracic, subcutaneous, intrathecal, and intra-articular injection or infusion. The polypeptide of the present invention can also be administered via a sustained-release system.

The present invention further relates to a pharmaceutical composition for specifically blocking nAChRs.

The conotoxin peptide of the present invention can be used as a probe for studying phylogenesis of animal nAChRs; as a probe for determining different subtypes of nAChRs; as a molecular model for designing new drug; as a tool drug and treatment drug for studying and diagnosis of neurological diseases such as addiction, Parkinson's diseases, dyspraxia, schizophrenia; a candidate drug for treatment of breast cancer, lung cancer, small cell lung cancer, or as a polypeptide pesticide for developing a new type of biopesticide.

Beneficial Effects of the Invention

The α-conotoxin peptide of the present invention can specifically block acetylcholine receptors (nAChRs), and has potent activity of analgesia and addiction withdrawal, and functions for treatment of Parkinson's disease, breast cancer and lung cancer cells, as well as functions for treatment of diseases such as addiction, dementia, schizophrenia, depression.

BRIEF DESCRIPTION OF THE DRAWINGS

FIG. 1: shows a propeptide gene sequence of α-conotoxin LvIA/LvD21 (LvIA) (SEQ ID NO:67) and a propeptide produced by coding the same, as well as a mature peptide produced by modification after translation (SEQ ID NO: 3). The arrow points out a processing site for modification after translation. The deduced proteinase hydrolysis processing site 1 (processing 1) is after alkaline amino acid arginine (R); the C-terminal amidation processing site is at the position of glycine indicated by the arrow, which is signed with character shading, i.e., processing 2. The first glycine at C-terminal of mature peptide that is closely adjacent to cysteine (Cys) usually is a processing site for modification after amidation translation, and the mature peptide produced by amidation at processing site 2 is named as LvIA/LvD21 (or LvIA), which sequence is: GCCSHPACNVDHPEIC# (# represents C-terminal amidation, SEQ ID NO: 4). The region of propeptide is indicated with italicizes, in which cysteine (C) is indicated with bold-face, and termination codon is indicated with *.

FIG. 2: shows sequences of synthesized linear peptide and mature peptide α-LvIA/LvD21 (SEQ ID NO: 4) and which disulfide bond linkage manners I-III and II-IV, as well as corresponding HPLC chromatogram.

FIG. 3: FIG. 3B shows a dose-response curve of α-LvIA/LvD21 highly selective blocking rat α3β2 vs. α6/α3β2β3 nAChRs; FIG. 3C shows dose-response curves of α-LvIA/LvD21 against other rat nervous subtypes and mouse muscular nAChRs; FIG. 3D shows dose-response curves of α-LvIA/LvD21 highly selective blocking human α3β2 vs. α6/α3β2β3 nAChRs. The values in FIG. 3 are mean values of currents obtained from 3-9 Xenopus oocytes.

FIG. 4: shows effects of different doses of α-LvIA/LvD21 on current of various nAChRs. In FIG. 4, "C" refers to control current, and the one closely following "C" refers to toxin concentration of α-LvIA/LvD21. The arrow indicates the current trace formed by the first Ach pulse as LvIA/LvD21 blocking corresponding receptor subtype after 5 min of incubation. FIG. 4 shows 100 nM α-LvIA/LvD21 specifically blocks α3β2 nAChR, while 10 µM totally does not block α2β2(B) and Mα1βδε(C) nAChRs subtypes.

FIG. 6: shows effects of 10 nM α-LvIA/LvD21 on currents of rat α3β2 nAChRs wild type (A), mutants α3β2 [F119Q] (B), α3β2[T59K] (C) and α3β2[V111I] (D), as well as different elution rates after blocking. In FIG. 6, "C" refers to the control current, the arrow indicates the current trace (~0 nA) formed by the first Ach pulse after 5 min of incubation with 10 nM α-LvIA/LvD21, "washout" refers to elution, and the time interval between two current traces is 1 min.

FIG. 11: shows mature peptide sequences of α-TxIB/Txd4 (FIG. 11A) and TxIB(G) (FIG. 11B) and their disulfide bond linkage manners I-III, II-IV.

FIG. 12: α-TxIB and TxIB(G) are specific blocking agents with high selectivity α6/α3β2β3 nAChR. In FIG. 12A, "C" refers to the control current, the arrow indicates the current trace (~0 nA) formed by the first Ach pulse after 5 min of incubation with 1 µM α-TxIB.

FIG. 14: shows α-conotoxin TxIC/Txd1 (TxIC) propeptide gene sequence (SEQ ID NO: 22/23), a propeptide produced by coding the same, and a mature peptide produced by modification after translation (SEQ ID NO:26/27). The arrow indicates the processing site for modification after translation. The deduced proteinase hydrolysis processing site 1 (processing site 1) follows alkaline amino acid arginine (R); the C-terminal amidation processing site is at glycine as indicated by the arrow, which is indicated with character shading, i.e., processing site 2. The first glycine residue of the mature peptide C-terminal that is closely adjacent to cysteine (Cys) is usually the processing site for modification after amidation translation, the mature peptide produced by amidation at processing site 2 is named as TxIC/Txd1 (or TxIC), which sequence is: GCCSHPVC-SAMSPIC # (# represents C-terminal amidation). The propeptide region is indicated with italicize, the mature peptide is indicated with underline, in which cysteine (C) is indicated with bold-face, and terminal codon is indicated with *.

FIG. 15: A shows mature peptide α-TxIC/Txd1 (SEQ ID NO: 28) sequence and its disulfide bond linkage manners I-III, II-IV. B shows HPLC chromatogram of α-TxIC/Txd1 containing disulfide bond linkage manners I-III, II-IV, in which the chromatography analysis conditions for this toxin peptide are: using Vydac C18 HPLC reversed phase analytic column, performing linear gradient elution within 40 min, from 15% to 50% for B solution, from 85% to 50% for A solution, in which A solution is 0.65% trifluoroacetic acid (TFA), B is aqueous solution of 0.5% TFA and 90% acetonitrile. Ultraviolet analytic optic wavelength is 214 nm, and TxIC has a peak time, i.e., retention time of 23.366 min.

SPECIFIC MODELS FOR CARRYING OUT THE INVENTION

Figure 2A:
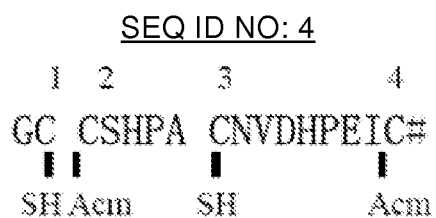
FIG. 2A shows the synthesized linear peptide sequence, as well as free —SH of Cys1 and Cys3 and protection group S-Acm (S-acetamidomethyl) of Cys2 and Cys4.

The embodiments of the present invention are illustrated in conjunction with examples as follows. Those skilled in the art would understand the following examples are merely used for illustrating the present invention, rather than limiting the scope of the present invention. The specific technologies or conditions that are not given in the specification are carried out according to the technologies or conditions described in the documents in the art (e.g., Molecular Cloning: A Laboratory Manual, Edition 3, J. Sambrook, etc., translated by HUANG Peitang, etc., Science Press), corresponding reference documents or specifications. All reagents or instruments which manufacturers are not given are commercially available conventional products.

Example 1-(1)

Cloning and Sequence Analysis of α-Conotoxin LvIA/LvD21 Gene

1. Extraction of Genome DNA of *C. textile* Linnaeus

Living bodies of *C. textile* Linnaeus were collected from coastal area of Hainan Island and Xisha Islands, and stored at −80° C. for standby use. Poison glands of cone shells were dissected out and weighed. The genome DNA of the poison glands were extracted using marine animal genome DNA extraction kit (purchased from China Beijing Tiangen Biochemical Science and Technology Co., Ltd.), in which the specific steps were performed by referring to the specification of the kit; or to reference documents, for example, Zheng Xiaodong, Gao Bingsen, Li Baozhu, Peng Chao, Wu Aiying, Zhu Xiaopeng, Chen Xin, Zhangsun Dongting, Luo Sulan, Screening primer for novel type α-conotoxin genetic clone, Chinese Journal of Biotechnologies, 2011, 21(4): 40-44.

The extracted poison gland genome total DNA was dissolved in 100 μL TE, 5 μL was used for 1.0% agarose gel electrophoresis, in which λ-EcoT14 I digest DNA Marker was standard, the integrality and size of the obtained DNA were measured. A nucleic acid/protein analyzer was used for measuring $OD_{260}$, $OD_{280}$ and ratio of $OD_{260}/OD_{280}$ of DNA solution, and the concentration (μg·ml$^{-1}$), purity and DNA yield (μg·g$^{-1}$) of DNA were calculated.

The extracted DNA was used as a template for conotoxin gene cloning and for following PCR amplification.

2. PCR reaction as well as cloning, sequencing and sequence analysis of product thereof According to α-CTx precursor gene intron sequence and its 3'-terminal untranslated region (3'-UTR) sequence, α-CTx specific primer is designed.

```
Upstream intron primer sequence:
                                    (SEQ ID NO: 9)
5'-GTGGTTCTGGGTCCAGCA-3';

Downstream 3'-UTR primer sequence:
                                    (SEQ ID NO: 10)
5'-GTCGTGGTTCAGAGGGTC-3'.
```

Each of the primers was a oligonucleotide fragment having 18 bases.

The extracted genome DNA raw solution was diluted and used as a template for PCR amplification. The following PCR amplification system and reaction conditions were used.

(1) PCR Reaction System:

| PCR reaction system | Reaction volume (25 μl) |
|---|---|
| Template DNA | 4 μl |
| P1 forward primer (5 μmol/μl) | 1 μl |
| P1 backward primer (5 μmol/μl) | 1 μl |

-continued

| PCR reaction system | Reaction volume (25 μl) |
|---|---|
| 2 × Taq PCR MasterMix | 12.5 μl |
| Aseptic dd H$_2$O | 6.5 μl |

(2) PCR Reaction Conditions:

| | | |
|---|---|---|
| Predenaturation 94° C. 5 min | 94° C. 7 min | |
| Denaturation | 94° C. 30 s | |
| Annealing | 50° C. 1 min | } 35 cycles |
| Extension | 72° C. 2 min | |
| Re-extension | 72° C. 10 min | |
| Preservation | 4° C. | |

The PCR specific amplification product was recovered, linked to T-easy vector (Promega), then used to transform *E. coli* XL1 strain (other commercially available competence *E. coli* could also be used), recon was picked out using blue-white colonies and ampicillin resistance, and the recon plasmid was extracted and purified and used for sequencing analysis. The following sequencing result was obtained:

(SEQ ID NO: 1)
*GTGGTTCTGGGTCCAGCATTTCGTGGCAGGGACGCCGCAGCCAAAGCGTC*
TGGCCTGGTTGGTCTGACTGACAGGAGAGGATGCTGTTCTCATCCTGCCT
GTAACGTAGATCATCCAGAAATTTGTGGCTGA.

In the above sequence, italicize letters are incon, corresponding primer.

The obtained PCR specific amplification product sequence was analyzed using DNAStar software to obtain the protein sequence coded thereby, 3'-untranslated region (UTR) sequence. By sequence analysis and comparison, the precursor gene of novel α4/7-CTx LvIA/LvD21 of the present invention was obtained, i.e., underlined parts of SEQ ID NO: 1, which were nucleotide sequence encoding LvIA/LvD21 conotoxin propeptide, as follows (114aa):

(SEQ ID NO: 2)
TTTCGTGGCAGGGACGCCGCAGCCAAAGCGTCTGGCCTGGTTGGTCTGAC
TGACAGGAGAGGATGCTGTTCTCATCCTGCCTGTAACGTAGATCATCCAG
AAATTTGTGGCTGA.

According to characteristics of the precursor gene and conotoxin, it was deduced that LvIA/LvD21 conotoxin propeptide is in the amino acid sequence as shown in SEQ ID NO: 2 (37aa), it was also called in the following text as α-conotoxin LvIA/LvD21 precursor or α-LvIA/LvD21 precursor or LvIA/LvD21 precursor or LvIA or LvD21 precursor, as follows:

(SEQ ID NO: 3)
*FRGRDAAAKASGLVGLTDRR*GCCSHPACNVDHPEICG.

The prediction of signal peptide, propeptide and mature peptide of the conotoxin proprotein was performed using online ProP 1.0 Server (Duckert, P.; Brunak, S.; Blom, N., Prediction of proprotein convertase cleavage sites. *Protein engineering, design & selection: PEDS* 2004, 17 (1), 107-12.). The methods and mechanism for the prediction can be seen in Luo S, Zhangsun D, Zhang B, Quan Y, Wu Y. Novel alpha-conotoxins identified by gene sequencing from cone snails native to Hainan, and their sequence diversity. *J Pept Sci*. 2006, 12 (11):693-704. The derivation process and results were also shown in FIG. 1.

According to the propeptide sequence, the mature peptide LvIA/LvD21 was also be derived, which had an amino acid sequence as shown in SEQ ID NO: 4 (16aa; hereinafter also cited as α-conotoxin LvIA/LvD21 or α-LvIA/LvD21 or LvIA/LvD21 or LvIA or LvD21):

GCCSHPACNVDHPEIC# (SEQ ID NO: 4; # represents C-terminal amidation).

LvIA/LvD21 had α-CTx specific CC-C-C cysteine pattern, in which disulfide bond linkage manners were I-III, II-IV (FIG. 2A-B), that was, two disulfide bonds were separately formed between the first and the third cysteines and between the second and the forth cysteines. LvIA/LvD21 is 4/7 type α-CTx (FIG. 1 and FIG. 2A-B).

In fact, the mature peptide LvIA/LvD21 of the present invention could also be obtained by correspondingly processing the propeptide (SEQ ID NO: 3 or 6) in vivo or in vitro (e.g., those shown in FIG. 1); optionally, by amidation of C-terminal in vivo or in vitro using amidation enzyme.

The nucleotide sequence encoding LvIA/LvD21 is as follows (48 bp):

(SEQ ID NO: 5)
GGATGCTGTTCTCATCCTGCCTGTAACGTAGATCATCCAGAAATTTGT.

The present invention further relates to the sequence (17aa) of mature peptide that is not subjected to the second processing site (processing 2):

(SEQ ID NO: 6)
GCCSHPACNVDHPEIC G;

and the corresponding nucleotide sequence thereof is as follows (54 bp):

(SEQ ID NO: 7)
GGATGCTGTTCTCATCCTGCCTGTAACGTAGATCATCCAGAAATTTGTGG
CTGA;
or 51 bp
(SEQ ID NO: 8)
GGATGCTGTTCTCATCCTGCCTGTAACGTAGATCATCCAGAAATTTGTG
GC.

Example 1-(2)

Cloning and Sequence Analysis of α-Conotoxin TxIB/Txd4 Gene

1. Extraction of Genome DNA of *C. textile* Linnaeus

*C. textile* Linnaeus living bodies collected from coastal areas such as Hainan Island and Xisha Islands were used as test materials, and stored at −80° C. for standby use. Poison glands of cone shells were firstly collected by dissection and weighed. Then, marine animal genome DNA extraction kits (purchased from Beijing Tiangen Biochemical Science and Technology Co., Ltd) were used to extract genome DNA, in which specific operations were performed according to the specification of the kits. The extracted genome total DNA of cone shells was dissolved in 100 μL TE, 5 μL was taken to perform 1.0% agarose gel electrophoresis, and integrality and size of the obtained DNA were detected using λ-EcoT14 I digest DNA Marker as standard. An analyzer for nucleic acid/protein was used to measure OD260, OD280 values and OD260/OD280 ratio of the DNA solution, and DNA concentration (μg·ml$^{-1}$), purity and DNA yield (μg·g$^{-1}$) were calculated. The extracted complete DNA was used as template in the next PCR amplification for conotoxin gene.

2. PCR Reaction and Cloning, Sequencing and Sequence Analysis of its Product

The method, system, conditions and primers to be used for PCR reaction were the same of Example 1-(1), except the template was a diluted liquid of the genome DNA raw liquid as extracted in Example 1.

The recovered PCR specific amplification product was linked to T-easy vector (Promega) and used to transform *E. coli* XL1 strain (other commercial competent *E. coli* cells could also be used), recombinants were picked out using blue and white colonies and ampicillin resistance, recombinant plasmids were extracted and purified and used for sequencing, to obtain the sequence of PCR specific amplification product.

Figures 9, 10:
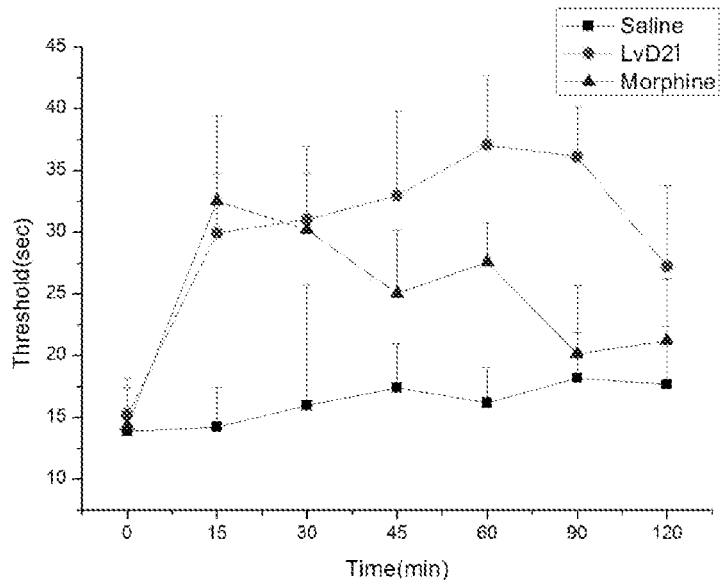
FIG. 9: shows analgesic effects of α-LvIA/LvD21 after intra-cerebral ventricle administration (ICV) for 120 min in mice hot plate test model. In the figure, the negative control Saline is physiological saline (Saline), the positive control is morphine (Morphine), which dose is 100 µg/kg mouse body weight; the dose of α-LvIA/LvD21 is 0.1 nmol/kg mouse body weight. In the figure, the abscissa Time (min) is number of minutes after administration; the ordinate Threshold (sec) is observed pain threshold with unit of second. The ordinate values of points in the figure are mean values and standard errors (Mean±SD). The comparison probability of significant difference is #p<0.05, and number of mice in each group is 10 (n=10).
FIG. 10: shows α-conotoxin TxIB/Txd4(TxIB) propeptide gene sequence, a propeptide produced by coding the same, and a mature peptide produced by modification after translation. The arrow indicates the processing site for modification after translation. The deduced proteinase hydrolysis processing site 1 (processing site 1) follows alkaline amino acid arginine (R); the C-terminal amidation processing site may at sites of two glycines indicated by the arrow, which is indicated with character shading, i.e., processing site 2 or processing site 3. The first or second glycine residues of the mature peptide C-terminal which are closely adjacent to cysteine are usually processing sites for modification after amidation translation, the mature peptide produced by amidation at processing site 2 is named as TxIB/Txd4 (or TxIB), which sequence is: GCCSDPPCRNKHPDLC# (# represents C-terminal amidation, SEQ ID NO: 11); the mature peptide produced by amidation at processing site 3 is named as TxIB/Txd4(G) (or TxIB(G)), which sequence is: GCCSDPPCRNKHPDLCG# (# represents C-terminal amidation, SEQ ID NO: 12). The C-terminal of TxIB(G) has one more glycine (G) than that of TxIB, and thus is an analogue of TxIB. The propeptide region is indicated with italicize, the mature peptide is indicated with underline, in which cysteine is indicated with bold-face, and terminal codon is indicated with *.

The obtained PCR specific amplification product sequence was analyzed with DNAStar software to obtain its protein coding sequence, 3'-untranslated region (UTR) sequence. By sequence analysis, the precursor gene of a novel α-CTx TxIB/Txd4 of the present invention was obtained (SEQ ID NO: 21) (FIG. 10).

The predication of signal peptide, propeptide and mature peptide of the conotoxin precursor protein was performed by on-line ProP 1.0 Server (Duckert, P.; Brunak, S.; Blom, N., Prediction of proprotein convertase cleavage sites. *Protein engineering, design & selection: PEDS* 2004, 17 (1), 107-12.).

According to the features of the precursor gene and conotoxin, TxIB/Txd4 conotoxin propeptide was deduced, which had a protein sequence containing 41 amino acids as shown in SEQ ID NO: 15.

According to the propeptide sequence, the mature peptide TxIB/Txd4 or TxIB/Txd4(G) were deduced, which separately had amino acid sequence as shown in SEQ ID NO: 11 or SEQ ID NO: 12, in which the method and principle for deduction could be seen in Luo S, Zhangsun D, Zhang B, Quan Y, Wu Y. Novel alpha-conotoxins identified by gene sequencing from cone snails native to Hainan, and their sequence diversity. J Pept Sci. 2006, 12 (11):693-704, and on-line software ProP 1.0 Server.

The details of results of the deduction could be seen in FIG. 10.

All mature peptides have cysteine pattern of CC-C-C. TxIB(G) has one more glycine (G) at C-terminal than TxIB, and thus is an analogue of TxIB. TxIB/Txd4 or TxIB/Txd4 (G) contains specific cysteine pattern of CC-C-C of α-CTx, in which disulfide bond linkage manner can be I-III, II-IV (FIG. 11, A-B), that is, two pairs of disulfide bonds can separately formed between the first cysteine and the third cysteine, and between the second cysteine and the forth cysteine. TxIB/Txd4 and TxIB/Txd4(G) are 4/7 type α-CTx (FIG. 10 and FIG. 11).

(1) Amino acid sequence (mature peptide) as shown in SEQ ID NO: 11 (also called in the text as α-conotoxin TxIB/Txd4 or α-TxIB/Txd4 or TxIB/Txd4 or TxIB):

(16aa)
(SEQ ID NO: 11)
GCCSDPPCRNKHPDLC.

Preferably, the C-terminal cysteine (C) is amidated, i.e., is represented by GCCSDPPCRNKHPDLC # (SEQ ID NO: 11), in which # represents C-terminal amidation.

(2) Amino acid sequence (mature peptide) as shown in SEQ ID NO: 12 (also called in the text as α-conotoxin TxIB/Txd4(G) or α-TxIB/Txd4(G) or TxIB/Txd4(G) or TxIB(G)):

(17aa)
(SEQ ID NO: 12)
GCCSDPPCRNKHPDLC G.

Preferably, the C-terminal glycine (G) is amidated, i.e., is represented by GCCSDPPCRNKHPDLC G # (SEQ ID NO: 12), in which # represents C-terminal amidation.

Without being restricted by any theory, the unamidated C-terminal glycine (at the $17^{th}$ site) of SEQ ID NO: 12 can be a recognition site for amidation enzyme (intracellular or extracellular), so as to result in the amidation of cysteine (C, at the $16^{th}$ site) closely adjacent to the glycine, and an amidated SEQ ID NO: 11 (GCCSDPPCRNKHPDLC #) would be obtained in this case.

(3) Amino acid sequence as shown in SEQ ID NO: 13:

(18aa)
(SEQ ID NO: 13)
GCCSDPPCRNKHPDLC GG.

Without being restricted by any theory, the $18^{th}$ site glycine of SEQ ID NO: 13 can be a recognition site for amidation enzyme (intracellular or extracellular), so as to result in the amidation of glycine (G) at the $17^{th}$ site closely adjacent to the glycine, and an amidated SEQ ID NO: 12(GCCSDPPCRNKHPDLC G #) would be obtained in this case.

or, the $17^{th}$ site glycine of SEQ ID NO: 13 can be a recognition site for amidation enzyme (intracellular or extracellular), so as to result in the amidation of cysteine (C) at the $16^{th}$ site closely adjacent to the glycine, and an amidated SEQ ID NO: 11(GCCSDPPCRNKHPDLC #) would be obtained in this case.

(4) Amino acid sequence as shown in SEQ ID NO: 14:

(20aa)
(SEQ ID NO: 14)
GCCSDPPCRNKHPDLC GGRR.

Without being restricted by any theory, the $18^{th}$ site glycine of SEQ ID NO: 14 can be a recognition site for amidation enzyme (intracellular or extracellular), so as to result in the amidation of glycine (G) at the $17^{th}$ site closely adjacent to the glycine, and an amidated SEQ ID NO: 12 (GCCSDPPCRNKHPDLC G #) would be obtained in this case.

or, the $17^{th}$ site glycine of SEQ ID NO: 14 can be a recognition site for amidation enzyme (intracellular or extracellular), so as to result in the amidation of cysteine (C) at the $16^{th}$ site closely adjacent to the glycine, and an amidated SEQ ID NO: 11(GCCSDPPCRNKHPDLC #) would be obtained in this case.

(5) Amino acid sequence as shown in SEQ ID NO: 15 (also called in the text as α-conotoxin TxIB/Txd4 precursor or α-TxIB/Txd4 precursor or TxIB/Txd4 precursor or TxIB precursor) (precursor peptide):

(41 aa)
(SEQ ID NO: 15)
FDGRNTSANNKATDLMALPVR GCCSDPPCRNKHPDLC GGRR.

(6) Nucleotide sequence as shown in SEQ ID NO: 16 (coding TxIB/Txd4 mature peptide):
(48 bp)

-continued (SEQ ID NO: 16)
GGATGCTGTTCCGATCCTCCCTGTAGAAACAAGCACCCAGATCTTTGT.

(7) Nucleotide sequence as shown in SEQ ID NO: 17
(coding TxIB/Txd4 mature peptide or coding TxIB(G)
mature peptide):
(51 bp)

(SEQ ID NO: 17)
GGATGCTGTTCCGATCCTCCCTGTAGAAACAAGCACCCAGATCTTTGTG
GC.

(8) Nucleotide sequence as shown in SEQ ID NO: 18
(coding TxIB/Txd4 mature peptide or coding TxIB(G)
mature peptide):
(54 bp)

(SEQ ID NO: 18)
GGATGCTGTTCCGATCCTCCCTGTAGAAACAAGCACCCAGATCTTTGTG
GCGGA.

(9) Nucleotide sequence as shown in SEQ ID NO: 19
(coding TxIB/Txd4 mature peptide or coding TxIB(G)
mature peptide):
(63 bp)

(SEQ ID NO: 19)
GGATGCTGTTCCGATCCTCCCTGTAGAAACAAGCACCCAGATCTTTGTG
GCGGAAGACGCTGA.

(10) Nucleotide sequence as shown in SEQ ID NO: 20
(coding TxIB/Txd4 or TxIB(G) precursor protein
sequence):
(123 bp)

(SEQ ID NO: 20)
TTTGATGGCAGGAATACCTCAGCCAACAACAAAGCGACTGACCTGATGG
CTCTGCCTGTCAGGGGATGCTGTTCCGATCCTCCCTGTAGAAACAAGCA
CCCAGATCTTTGTGGCGGAAGACGCTGA.

(11) Nucleotide sequence as shown in SEQ ID NO: 21:
(170 bp)

(SEQ ID NO: 21)
*GTGGTTCTGGGTCCAGCATTTGATGGCAGGAATACCTCAGCCAACAACA*
*AAGCGACTGACC*TGATGGCTCTGCCTGTCAGGGGATGCTGTTCCGATCC
TCCCTGTAGAAACAAGCACCCAGATCTTTGTGGCGGAAGACGCTGATGC
TCCAGGACCCTCTGAACCACGAC
(italic characters are intron, corresponding to
primer).

Example 1-(3)

Cloning and Sequence Analysis of α-Conotoxin
TxIC/Txd1 Gene

1. Extraction of Genome DNA of Poison Gland of *C. textile* Linnaeus

*C. textile* Linnaeus living bodies collected from coastal areas such as Hainan Island and Xisha Islands were used as test materials, and stored at −80° C. for standby use. Poison glands of cone shells were firstly collected by dissection and weighed. Then, marine animal genome DNA extraction kits (purchased from Beijing Tiangen Biochemical Science and Technology Co., Ltd) were used to extract genome DNA of poison glands, in which specific operations were performed according to the specification of the kits, to obtain the genome DNA of poison glands.

The extracted poison gland genome DNA was dissolved in 100 μL TE, 5 μL was taken to perform 1.0% agarose gel electrophoresis, and integrality and size of the obtained DNA were detected using λ-EcoT14 I digest DNA Marker as standard. An analyzer for nucleic acid/protein was used to measure $OD_{260}$, $OD_{280}$ values and $OD_{260}/OD_{280}$ ratio of the DNA solution, and DNA concentration (μg·ml$^{-1}$), purity and DNA yield (μg·g$^{-1}$) were calculated.

The extracted DNA was used as template for cloning conotoxin gene in the next PCR amplification.

2. PCR Reaction and Cloning, Sequencing and Sequence Analysis of its Product

The method, system, conditions and primers to be used for PCR reaction were the same of Example 1-(1), except the template was a diluted liquid of the genome DNA raw liquid as extracted in Example 1, which had a final concentration of 3 μg·ml$^{-1}$.

8 μl of amplification product was subjected to 1.5% agarose gel electrophoresis, electric voltage of 90V, for 20 min, to detect the size of amplification product using DL2000 DNA Marker as standard.

The PCR amplification product was recovered, linked to T-easy vector (Promega) and used to transform *E. coli* XL1 strain (other commercial competent *E. coli* cells could also be used), recombinants were picked out using blue and white colonies and ampicillin resistance, recombinant plasmids were extracted and purified and used for sequencing. Two sequencing results were obtained, i.e., SEQ ID NO: 22 and SEQ ID NO: 23 (FIG. 14, 168 bp), which were respectively shown as follows:

(SEQ ID NO: 22)
GTGGTTCTGGGTCCAGCATTTGATGGCAGGAATGCTGCAGGCAACGAC

AAAATGTCCGCCCTGATGGCTCTGACCA[C]CAGGGGATGCTGTTCCCATCC

TGTCTGTAGCGCGATGAGTCCAATCTGTGGCTGAAGACGCTGATGCTCCAG

GACCCTCTGAACCACGACA,
or (SEQ ID NO: 23)
GTGGTTCTGGGTCCAGCATTTGATGGCAGGAATGCTGCAGGCAACGAC

AAAATGTCCGCCCTGATGGCTCTGACCA[T]CAGGGGATGCTGTTCCCATCC

TGTCTGTAGCGCGATGAGTCCAATCTGTGGCTGAAGACGCTGATGCTCCA

GGACCCTCTGAACCACGACA.

The above two sequences were different only in base at the 77$^{th}$ site, which was marked with frame.

The obtained PCR specific amplification product sequence was analyzed using DNAStar software to obtain the protein sequence coded thereby, 3'-untranslated region (UTR) sequence. By sequence analysis and comparison, the precursor gene of novel α4/6-CTx TxIC/Txd1 of the present invention was obtained, i.e., underlined parts of SEQ ID NO: 22 and SEQ ID NO: 23, which were nucleotide sequence encoding TxIC/Txd1 conotoxin propeptide, as follows (114aa):

(SEQ ID NO: 24)
TTTGATGGCAGGAATGCTGCAGGCAACGACAAAATGTCCGCCCTGATG

GCTCTGACCA[C]CAGGGGATGCTGTTCCCATCCTGTCTGTAGCGCGATGAG

TCCAATCTGTGGCTGA;

(SEQ ID NO: 25)
TTTGATGGCAGGAATGCTGCAGGCAACGACAAAATGTCCGCCCTGATG

GCTCTGACCA[T]CAGGGGATGCTGTTCCCATCCTGTCTGTAGCGCGATGAG

TCCAATCTGTGGCTGA.

According to characteristics of the precursor gene and conotoxin, it was deduced that TxIC/Txd1 conotoxin propeptide is in the amino acid sequence as shown in SEQ ID NO: 26 or SEQ ID NO: 27 (37aa), it was also called in the following text as α-conotoxin TxIC/Txd1 precursor or α-TxIC/Txd1 precursor or TxIC/Txd1 precursor or TxIC precursor):

```
                                              (SEQ ID NO: 26)
FDGRNAAGNDKMSALMALTTR↓GCCSHPVCSAMSPIC G;

(SEQ ID NO: 27)
FDGRNAAGNDKMSALMALTIR↓GCCSHPVCSAMSPIC G.
```

The prediction of signal peptide, propeptide and mature peptide of the conotoxin precursor protein was performed using online ProP 1.0 Server (Duckert, P.; Brunak, S.; Blom, N., Prediction of proprotein convertase cleavage sites. *Protein engineering, design & selection: PEDS* 2004, 17 (1), 107-12.). The methods and mechanism for the prediction can be seen in Luo S, Zhangsun D, Zhang B, Quan Y, Wu Y. Novel alpha-conotoxins identified by gene sequencing from cone snails native to Hainan, and their sequence diversity. *J Pept Sci.* 2006, 12 (11):693-704. The derivation process and results were also shown in FIG. 14.

According to the propeptide sequence, the mature peptide TxIC/Txd1 was also be derived, which had an amino acid sequence as shown in SEQ ID NO: 28 (hereinafter also cited as α-conotoxin TxIC/Txd1 or α-TxIC/Txd1 or TxIC/Txd1 or TxIC):

GCCSHPVCSAMSPIC #(SEQ ID NO: 28, # represents C-terminal amidation, 15aa)

TxIC/Txd1 had α-CTx specific CC-C-C cysteine pattern, in which disulfide bond linkage manners were I-III, II-IV (FIG. 15A), that was, two disulfide bonds were separately formed between the first and the third cysteines and between the second and the forth cysteines. TxIC/Txd1 is 4/6 type α-CTx (FIG. 14 and FIG. 15A). TxIC/Txd1 is a new α-conotoxin, which comparisons of sequence and activity with other α-CTx were shown in Table 6.

In fact, the mature peptide TxIC/Txd1 of the present invention could also be obtained by correspondingly processing the propeptide (SEQ ID NO: 26 or 27 or 30) in vivo or in vitro (e.g., those shown in FIG. 14); optionally, by amidation of C-terminal in vivo or in vitro using amidation enzyme.

The nucleotide sequence encoding TxIC/Txd1 is as follows (45 bp):

```
                                              (SEQ ID NO: 29)
GGATGCTGTTCCCATCCTGTCTGTAGCGCGATGAGTCCAATCTGT.
```

The present invention further relates to the sequence of mature peptide (16aa) that is not subjected to the second processing site (processing 2):

```
                                              (SEQ ID NO: 30)
     GCCSHPVCSAMSPIC G,
``` and the corresponding nucleotide sequence is as follows (51 bp):

```
                                              (SEQ ID NO: 31)
GGATGCTGTTCCCATCCTGTCTGTAGCGCGATGAGTCCAATCTGTGGC
TGA.
```

Example 2-(1)

Artificial Synthesis of α-Conotoxin LvIA/LvD21

According to the amino acid sequence (SEQ ID NO: 4, C-terminal amidated) of αO-conotoxin LvIA/LvD21 mature peptide, LvIA/LvD21 linear peptide (FIG. 2B) was artificially synthesized by Fmoc method. The specific method was as follows.

The resin peptide was artificially synthesized by Fmoc chemical method, for example by polypeptide synthesizer or manual synthesis method. Except cysteines, residual amino acids were protected with standard side chain protecting groups. As for LvIA/LvD21, the —SH groups of its $1^{st}$ and $3^{rd}$ cysteines (Cys) were protected with Trt (S-trityl), and the —SH groups of its $2^{nd}$ and $4^{th}$ cysteines (Cys) were protected with Acm (S-acetamidomethyl) in pairs. The synthesis steps comprised: using Fmoc and FastMoc methods of solid phase synthesis method, synthesizing 3 isomer linear peptides by ABI Prism 433a polypeptide synthesizer. The side chain protecting groups of Fmoc amino acids were: Pmc (Arg), Trt(Cys), But (Thr, Ser, Tyr), OBut (Asp), Boc (Lys). Fmoc HOBT DCC method, Rink amidation resin and Fmoc amino acids were used, and synthesis steps were carried out according to synthesis manual of instruments. In order to complete synthesis, piperidine deprotecting time and coupling time were properly extended, respectively, double coupling was used for amino acids difficult to link, and thus the resin peptides were obtained. The linear peptide was cut from resin using reagent K (trifluoroacetic acid/water/ethanedithiol/phenol/thioanisole; 90:5:2.5:7.5:5, v/v/v/v), and subjected to glacial diethyl ether precipitation and washing to recover a crude product of the linear peptide, reversed phase prep-HPLC C18 column (Vydac) was used for purification, and elution linear gradient was 0-40% B90 within 0-40 min, 40-100% B90 within 40-45 min. Solution B90 was 90% ACN (acetonitrile), 10% $H_2O$, 0.05% TFA (trifluoroacetic acid); solution A was 0.075% TFA aqueous solution. Ultraviolet absorption analysis was carried out under 214 nm. The purified linear peptide was subjected to purity detection with HPLC C18 column (Vydac) (FIG. 2C), in which HPLC conditions were the same of the preparation and purification, flow rate was 0.75 ml/min, and α-conotoxin LvIA/LvD21 linear peptide had an appearance time of 27.713 min.

Figure 2B:
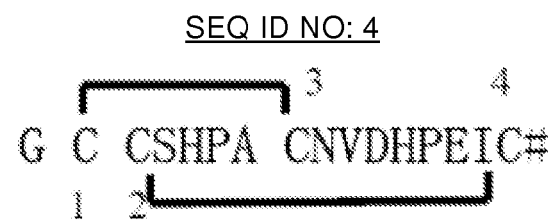
FIG. 2B shows the mature peptide α-LvIA/LvD21 sequence after oxidation folding, as well as I-III and II-IV disulfide bond linkage manners as contained (SEQ ID NO: 4)
Figure 2C:
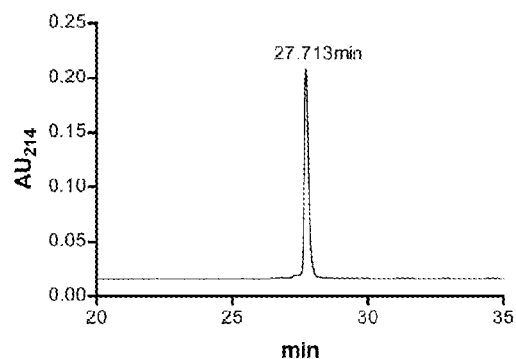
FIG. 2C shows the HPLC chromatogram of the synthesized linear peptide in FIG. 2A, which retention time is 27.713 min.
Figure 2D:
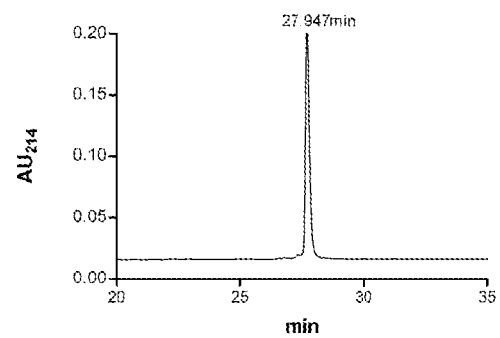
FIG. 2D shows the HPLC chromatogram of the oxidation peptide in FIG. 2B, which retention time is 27.947 min.

The linear peptide of LvIA/LvD21 was subjected to two-step oxidation folding reaction according to documents (Dowell, C.; Olivera, B. M.; Garrett, J. E.; Staheli, S. T.; Watkins, M.; Kuryatov, A.; Yoshikami, D.; Lindstrom, J. M.; McIntosh, J. M., Alpha-conotoxin PIA is selective for alpha6 subunit-containing nicotinic acetylcholine receptors. *The Journal of neuroscience* 2003, 23 (24), 8445-52.), which steps were briefly described as follows:

Firstly, the first pair of disulfide bond between two cysteines with Trt protecting groups was formed by potassium ferricyanide method (20 mM potassium ferricyanide, 0.1 M Tris, pH 7.5, 30 min). After monocycle peptide was purified with reversed phase HPLC C18 column (Vydac), iodine oxidation was carried out (10 mM iodine in $H_2O$:trifluoroacetic acid:acetonitrile (78:2:20 by volume, 10 min), to remove Acm of another 2 cysteines, and form the second pair of disulfide bond between the 2 cysteines at the same time (FIG. 2B). Dicyclic peptide was purified with reversed phase HPLC C18 column (Vydac) to obtain αO-conotoxin in which disulfide bonds were directionally formed between corresponding cysteines in sequence of N-terminal to C-terminal, the appearance time of LvIA/LvD21 was 27.947 min (FIG. 2D), and confirmed with mass spectrum (MS). HPLC analytic conditions were: using Vydac C18 reversed phase prep-HPLC column, performing linear gradient elution within 40 min, in which solution B was from 0% to 40%, and solution A was from 100% to 60%; the solution A was 0.075% TFA (trifluoroacetic acid), solution B was 0.05% TFA and 90% ACN (acetonitrile), the flow rate was 0.75 ml/min. Ultraviolet absorption analysis was carried out under 214 nm.

The theoretical molecular weight (monoisotopic mass) of the LvIA/LvD21 after oxidation folding was in consistent with the measured molecular weight; the monoisotopic mass of the LvIA/LvD21 was 1678.91 Da, while the measured molecular weight of LvIA/LvD21 was 1678.7977 Da, which was 4 Da smaller than its linear peptide molecular weight of 1682.91 Da. Colorimetric assay was used to detect polypeptide concentration under wavelength of 280 nm, and polypeptide concentration and mass were calculated according to Beer-Lambert equation. These quantified and well-folded toxin peptides were used for subsequent activity assay in the following examples.

Example 2-(2)

Artificial Synthesis of α-Conotoxin TxIB and TxIB(G)

According to the amino acid sequences (SEQ ID NO: 11 and 12, both C-terminal amidated) of αO-conotoxin TxIB and TxIB(G) mature peptide, TxIB and TxIB(G) linear peptides (FIG. 11) were artificially synthesized by Fmoc method. The specific method was as follows:

The resin peptides were artificially synthesized by Fmoc chemical method, for example by polypeptide synthesizer or manual synthesis method. Except cysteines, residual amino acids were protected with standard side chain protecting groups. As for TxIB and TxIB(G), the —SH groups of its $1^{st}$ and $3^{rd}$ cysteines (Cys) were protected with Trt (S-trityl), and the —SH groups of its $2^{nd}$ and $4^{th}$ cysteines (Cys) were protected with Acm (S-acetamidomethyl) in pairs. The synthesis steps comprised: using Fmoc and FastMoc methods of solid phase synthesis method, synthesizing 3 isomer linear peptides by ABI Prism 433a polypeptide synthesizer. The side chain protecting groups of Fmoc amino acids were: Pmc (Arg), Trt(Cys), But (Thr, Ser, Tyr), OBut (Asp), Boc (Lys). Fmoc HOBT DCC method, Rink amidation resin and Fmoc amino acids were used, and synthesis steps were carried out according to synthesis manual of instruments. In order to complete synthesis, piperidine deprotecting time and coupling time were properly extended, respectively, double coupling was used for amino acids difficult to link, and thus the resin peptides were obtained. The linear peptides were cut from resin using reagent K (trifluoroacetic acid/water/ethanedithiol/phenol/thioanisole; 90:5:2.5:7.5:5, v/v/v/v/v), and subjected to glacial diethyl ether precipitation and washing to recover a crude product of the linear peptide, reversed phase prep-HPLC C18 column (Vydac) was used for purification, and elution linear gradient was 2-42% B60 within 0-40 min, 42-100% B60 within 42-47 min. Solution B60 was 60% ACN (acetonitrile), 40% $H_2O$, 0.05% TFA (trifluoroacetic acid); solution A was 0.075% TFA aqueous solution.

The purified linear peptide was subjected to purity detection with analytic HPLC C18 column (Vydac), in which elution gradient was 2-42% B60 within 0-40 min, 42-100% B60 within 42-47 min, flow rate was 1 ml/ml. It had a purity of up to 95% or more, and was used for oxidization folding.

The linear peptide of TxIB and TxIB(G) was subjected to two-step oxidation folding reaction according to documents (Dowell, C.; Olivera, B. M.; Garrett, J. E.; Staheli, S. T.; Watkins, M.; Kuryatov, A.; Yoshikami, D.; Lindstrom, J. M.; McIntosh, J. M., Alpha-conotoxin PIA is selective for alpha6 subunit-containing nicotinic acetylcholine receptors. *The Journal of neuroscience* 2003, 23 (24), 8445-52.), which steps were briefly described as follows:

Firstly, the first pair of disulfide bond between two cysteines with Trt protecting groups was formed by potassium ferricyanide method (20 mM potassium ferricyanide, 0.1 M Tris, pH 7.5, 30 min). After monocycle peptide was purified with reversed phase HPLC C18 column (Vydac), iodine oxidation was carried out (10 mM iodine in $H_2O$: trifluoroacetic acid:acetonitrile (78:2:20 by volume, 10 min), to remove Acm of another 2 cysteines, and form the second pair of disulfide bond between the 2 cysteines at the same time. Dicyclic peptide was purified with reversed phase HPLC C18 column (Vydac) to obtain αO-conotoxin in which disulfide bonds were directionally formed between corresponding cysteines in sequence of N-terminal to C-terminal, and confirmed with mass spectrum (MS).

The theoretical molecular weight (monoisotopic mass) of the TxIB and TxIB(G) after oxidation folding was in consistent with the measured molecular weight; the monoisotopic mass of the TxIB was 1738.7 Da, while the measured molecular weight of TxIB was 1738.6 Da; the monoisotopic mass of the TxIB(G) was 1795.7 Da, while the measured molecular weight of TxIB(G) was 1795.6 Da. Colorimetric assay was used to detect polypeptide concentration under wavelength of 280 nm, and polypeptide concentration and mass were calculated according to Beer-Lambert equation. These quantified and well-folded toxin peptides were used for subsequent activity assay in the following examples.

Example 2-(3)

Artificial Synthesis of α-Conotoxin TxIC

According to the amino acid sequence (SEQ ID NO: 28, C-terminal amidated) of αO-conotoxin TxIC mature peptide, TxIC linear peptide (FIG. 15A) was artificially synthesized by Fmoc method. The specific method was as follows.

The resin peptides were artificially synthesized by Fmoc chemical method, for example by polypeptide synthesizer or manual synthesis method. Except cysteines, residual amino acids were protected with standard side chain protecting groups. As for TxIC, the —SH groups of its $1^{st}$ and $3^{rd}$ cysteines (Cys) were protected with Trt (S-trityl), and the —SH groups of its $2^{nd}$ and $4^{th}$ cysteines (Cys) were protected with Acm (S-acetamidomethyl) in pairs. The synthesis steps comprised: using Fmoc and FastMoc methods of solid phase synthesis method, synthesizing 3 isomer linear peptides by ABI Prism 433a polypeptide synthesizer. The side chain protecting groups of Fmoc amino acids were: Pmc (Arg), Trt(Cys), But (Thr, Ser, Tyr), OBut (Asp), Boc (Lys). Fmoc HOBT DCC method, Rink amidation resin and Fmoc amino acids were used, and synthesis steps were carried out according to synthesis manual of instruments. In order to complete synthesis, piperidine deprotecting time and coupling time were properly extended, respectively, double coupling was used for amino acids difficult to link, and thus the resin peptides were obtained. The linear peptides were cut from resin using reagent K (trifluoroacetic acid/water/ethanedithiol/phenol/thioanisole; 90:5:2.5:7.5:5, v/v/v/v/v), and subjected to glacial diethyl ether precipitation and washing to recover a crude product of the linear peptide, reversed phase prep-HPLC C18 column (Vydac) was used for purification, and elution linear gradient was 15-50% B90 within 0-40 min, 50-100% B90 within 40-45 min. Solution B90 was 90% ACN (acetonitrile), 10% $H_2O$, 0.5% TFA (trifluoroacetic acid); solution A was 0.65% TFA aqueous solution.

Ultraviolet absorption analysis was carried out under 214 nm. The purified linear peptide was subjected to purity detection with analytic HPLC C18 column (Vydac), in which elution gradient was 2-42% B60 within 0-40 min, 42-100% B60 within 42-47 min, flow rate was 1 ml/ml. It had a purity of up to 95% or more, and was used for oxidization folding.

The linear peptide of TxIC was subjected to two-step oxidation folding reaction according to documents (Dowell, C.; Olivera, B. M.; Garrett, J. E.; Staheli, S. T.; Watkins, M.; Kuryatov, A.; Yoshikami, D.; Lindstrom, J. M.; McIntosh, J. M., Alpha-conotoxin PIA is selective for alpha6 subunit-containing nicotinic acetylcholine receptors. *The Journal of neuroscience* 2003, 23 (24), 8445-52.), which steps were briefly described as follows:

Firstly, the first pair of disulfide bond between two cysteines with Trt protecting groups was formed by potassium ferricyanide method (20 mM potassium ferricyanide, 0.1 M Tris, pH 7.5, 30 min). After monocycle peptide was purified with reversed phase HPLC C18 column (Vydac), iodine oxidation was carried out (10 mM iodine in $H_2O$: trifluoroacetic acid:acetonitrile (78:2:20 by volume, 10 min), to remove Acm of another 2 cysteines, and form the second pair of disulfide bond between the 2 cysteines at the same time. Dicyclic peptide was purified with reversed phase HPLC C18 column (Vydac), in which the linear gradient was still 15-50% B90 within 0-40 min, 50-100% B90 within 40-45 min, the solvent B90 was 90% ACN (acetonitrile), 10% $H_2O$, 0.5% TFA (trifluoroacetic acid); solution A was 0.65% TFA aqueous solution. Ultraviolet absorption analysis was carried out under 214 nm. Thus, the αO-conotoxin in which disulfide bonds were directionally formed between corresponding cysteines in sequence of N-terminal to C-terminal was obtained, the appearance time of TxIC was 23.366 min (FIG. 15B), and confirmed with mass spectrum (MS).

The theoretical molecular weight (monoisotopic mass) of the TxIC after oxidation folding was in consistent with the measured molecular weight; the monoisotopic mass of the TxIC was 1488.81 Da, while the measured molecular weight of TxIC 1488.4266 Da, which was 4 Da smaller than its linear peptide molecular weight of 1492.815 Da. Colorimetric assay was used to detect polypeptide concentration under wavelength of 280 nm, and polypeptide concentration and mass were calculated according to Beer-Lambert equation. These quantified and well-folded toxin peptides were used for subsequent activity assay in the following examples.

Example 3-(1)

Experiment of Blocking Various nAChRs with α-Conotoxin LvIA/LvD21

The methods of document (Azam L, Yoshikami D, McIntosh J M. Amino acid residues that confer high selectivity of the alpha6 nicotinic acetylcholine receptor subunit to alpha-conotoxin MII[S4A,E11A,L15A]. *J Biol Chem*. 2008; 283 (17):11625-32.), the specification of in vitro transcription kit (mMessage mMachine in vitro transcription kit (Ambion, Austin, Tex.)) were referred to prepare cRNAs of various rat nervous type nAChRs subtypes (α3β2, α6/α3β2β3, α6/α3β4, α9α10, α4β2, α4β4, α3β4, α2β2, α2β4, α7), humanα3β2, α6/α3β2β3, α3β4, and mice muscle type nAChRs (α1β1δε), their concentrations were measured and calculated by OD values under UV 260 nm. Oocytes (frogspawns) of *Xenopus* (*Xenopus laveis*) were collected and dissected, cRNA was injected into frogspawns, the injection dose for each subtype was 5 ng cRNA. For muscle nAChR, each subtype was injected with 0.5-2.5 ng DNA. The frogspawns were cultured in ND-96. The collected frogspawns were injected with cRNA within 1-2 days, and used for nAChRs voltage clamp recording within 1-4 days after the injection.

One of the frogspawns injected with cRNA was placed in 30 uL of Sylgard record tank (diameter 4 mm×depth 2 mm), gravity perfused with ND96 perfusate (96.0 mM NaCl, 2.0 mM KCl, 1.8 mM $CaCl_2$, 1.0 mM $MgCl_2$, 5 mM HEPES, pH 7.1-7.5) containing 0.1 mg/ml BSA (bovine serum albumin), or ND96 (ND96A) containing 1 mM atropine, flow rate was 1 ml/min. All conotoxin solutions also contained 0.1 mg/ml BSA to reduce non-specific adsorption of toxin, a change-over valve (SmartValve, Cavro Scientific Instruments, Sunnyvale, Calif.) could be used for freely switching between perfusion of toxin and acetylcholine (ACh), and a series of three-way solenoid valves (solenoid valves, model 161TO31, Neptune Research, Northboro, Mass.) were used for freely switching between perfusion of ND96 and ACh. Ach gating current was set at "slow" clamp with double-electrode voltage clamp amplifier (model OC-725B, Warner Instrument Corp., Hamden, Conn.), and on-line recording of clamp gain was performed at the maximum value (×2000) position. Glass electrodes were drawn from glass capillaries (fiber-filled borosilicate capillaries, WPI Inc., Sarasota, Fla.) with 1 mm external diameter×0.75 mm internal diameter, and filled with 3 M KCl as voltage and current electrodes. Membrane voltage was clamped at −70 mV. The control of whole system and data recording were carried out with a computer. ACh pulse was to automatically perfuse ACh for 1 s per interval of 5 min. ACh had concentration of 10 μM for oocyte expression of muscle type nAChRs and nervous type α9α10 nAChRs; 200 μM for α7 of nervous type nAChRs, and 100 μM for other subtypes. At least 4 oocytes were used for recording situations of current response and current tracks of a subtype under different toxin concentrations.

The measured current data were subjected to statistic analysis with GraphPad Prism software (San Diego, Calif.), dose-response curves were plotted, half-blocking concentration ($IC_{50}$) of conotoxin and many other parameters relating to toxin-blocking nAChRs were calculated.

The results shown that LvIA/LvD21 (as prepared in Example 2-(1)) showed blocking effect on rat α3β2 nAChRs, and had feature of fast elution (FIG. 3). LvIA/LvD21 showed most potent effect on α3β2 nAChRs, and which half-blocking dose $IC_{50}$ of merely 8.69 nM, with error ranges of 6.9-11.0 n (Table 1). 100 nM α-LvIA/LvD21 completely blocked the current generated by Ach-gated rat α3β2 nAChRs open, and could be completely eluted within 2 min, and this blocking was reversible (FIG. 3A). The blocking activity of LvIA/LvD21 to α6/α3β4 nAChRs took the second place, showing half-blocking dose $IC_{50}$ and error range as 120.9 (86.1-169.8) nM; at the third place was α3β4, showing half-blocking dose $IC_{50}$ and error range as 148.4 (103.2-213.2) nM. The blocking activity of LvIA/LvD21 to α6/α3β2β3 nAChRs was very weak, showing half-blocking dose $IC_{50}$ and error range as 852 (590-1230) nM; extremely weak blocking activity to α7, α2β4 was observed, which half-blocking dose $IC_{50}$ and error range were separately up to 3000 (1797-4997) nM and 15520 (11600-20770) nM. It showed no blocking activity to other subtypes, including α9α10, α2β2, α4β2, α4β4 and Mα1β1δε, which $IC_{50}$>10 μM (Table 1). The dose-response curves of LvIA/LvD21 to various nAChRs subtypes were shown in FIG. 3B, 3C, 3D.

Figure 3A:
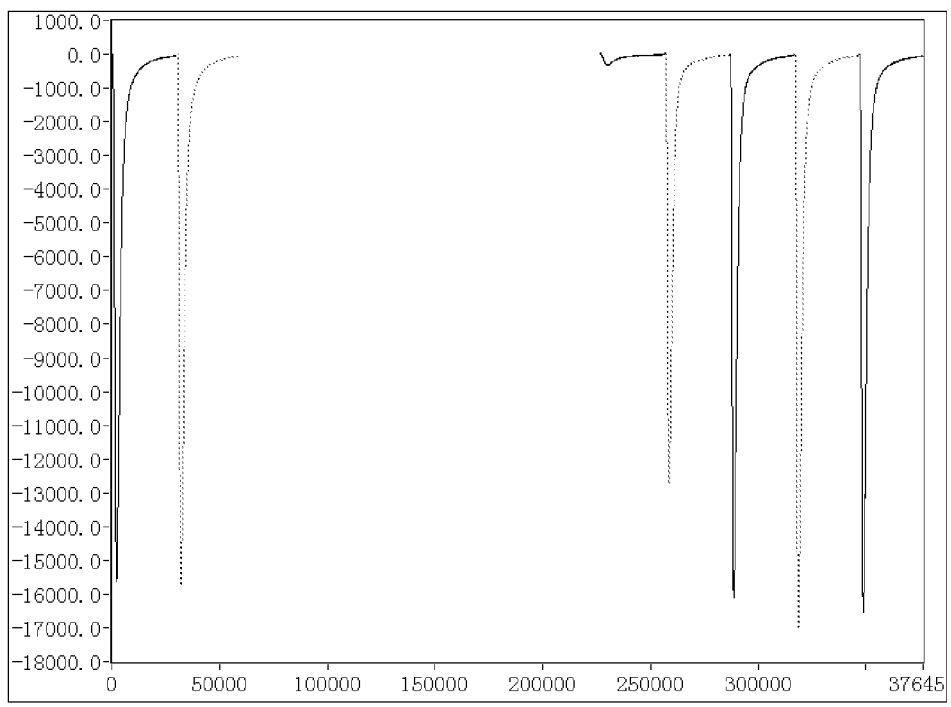
FIG. 3A shows effects of 100 nM α-LvIA/LvD21 on electric current of α3β2 nAChR, in which clamping voltage is 70 mV, "C" in FIG. 3A refers to control current, the arrow indicates the current trace (~0 nA) formed by the first Ach pulse after 5 min of incubation with 100 nM α-LvIA/LvD21, and the time interval between two current traces is 1 min.
Figure 3B:
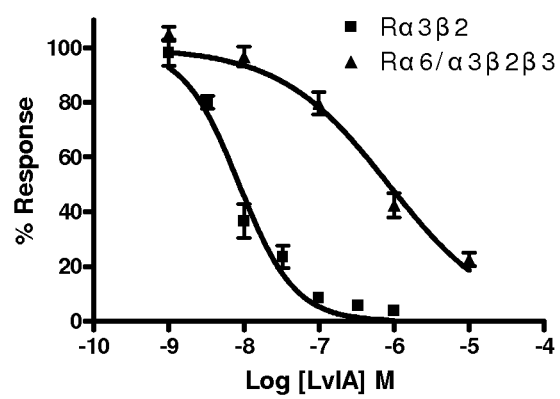
FIG. 3B, 3C, 3D separately show dose-response curves of α-LvIA/LvD21 against various subtypes of nAChRs (11 of rat, and 2 of human), in which abscissa represents log value of molar concentration (M) of the used α-LvIA/LvD21 (Log [LvIA/LvD21]M); ordinate represents dose response percentage (%), which is a percentage of acetylcholine receptor current to the control current under toxin with corresponding concentration.
Figure 3C:
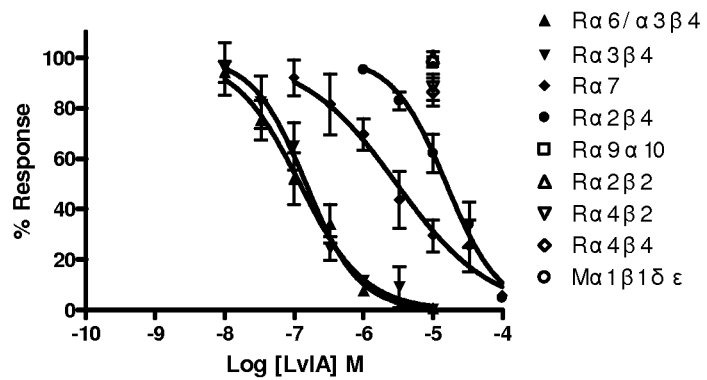
Figure 3D:
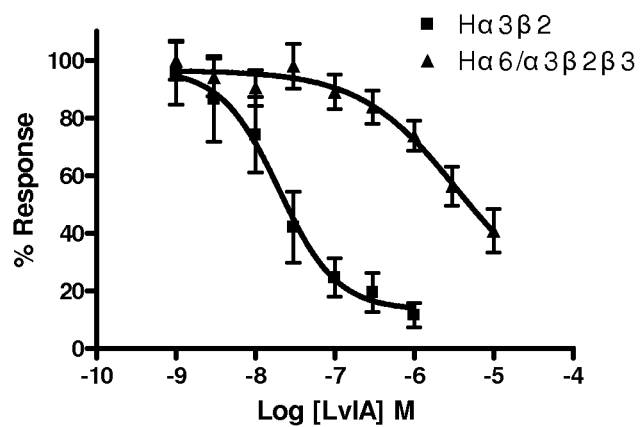

In comparison, the blocking activity of α-LvIA/LvD21 to α3β2 was ≥100 times greater than that to α6/α3β2β3, that was, ~100 times higher in rats, and ~305 times higher in human (FIG. 3B, 3D and Table 1). Thus, α-LvIA/LvD21 was the first ligand with the best selectivity and discrimination for α3β2 vs. α6/α3β2β3. All conotoxins as disclosed in the art block α6/α3β2β3 nAChRs almost at the same time. Hence, α-LvIA/LvD21 is the first real novel blocking agent with high selectivity for α3β2* vs. α6β2* nAChRs, and thus has very important value for studying and understanding the function and meanings of said subtype under normal and disease states.

The α-LvIA/LvD21 showed higher selectivity in blocking α3β2 nAChRs.

Figure 4A:
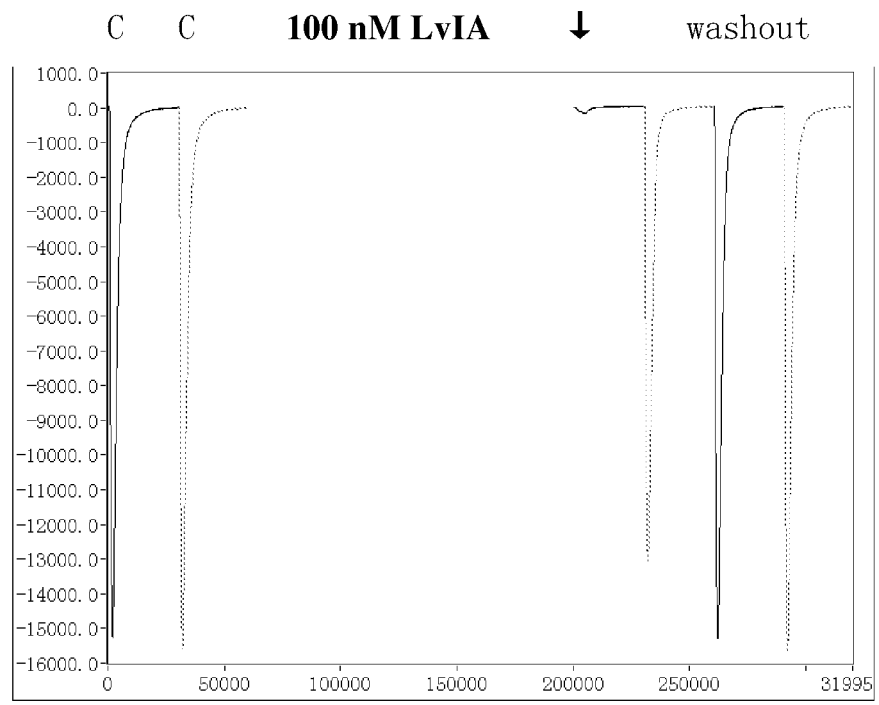
FIG. 4A shows effects of 100 nM α-LvIA/LvD21 on current of rat α3β2 nAChRs.
Figure 4B:
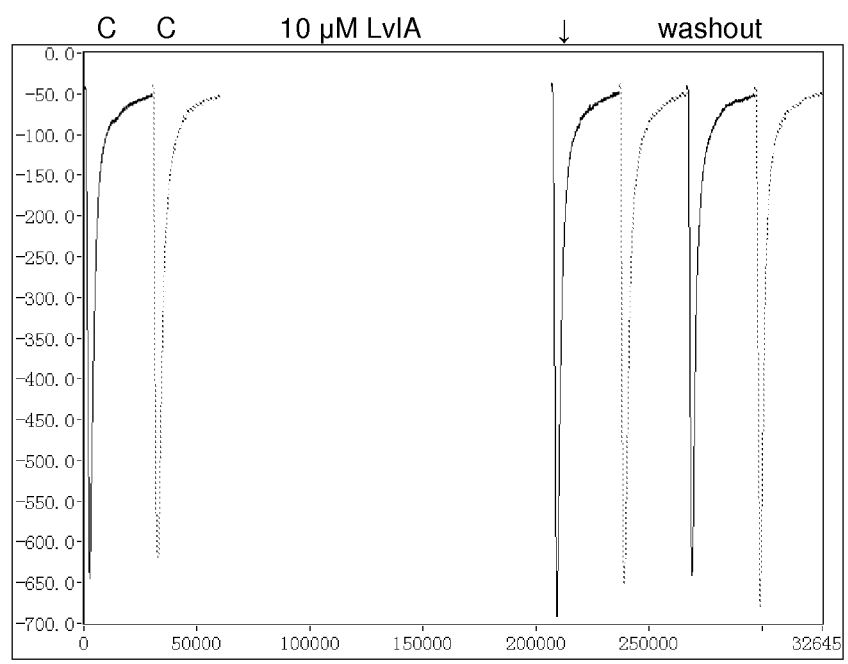
FIG. 4B shows 10 μM α-LvIA/LvD21 on current of α2β2 nAChRs.
Figure 4C:
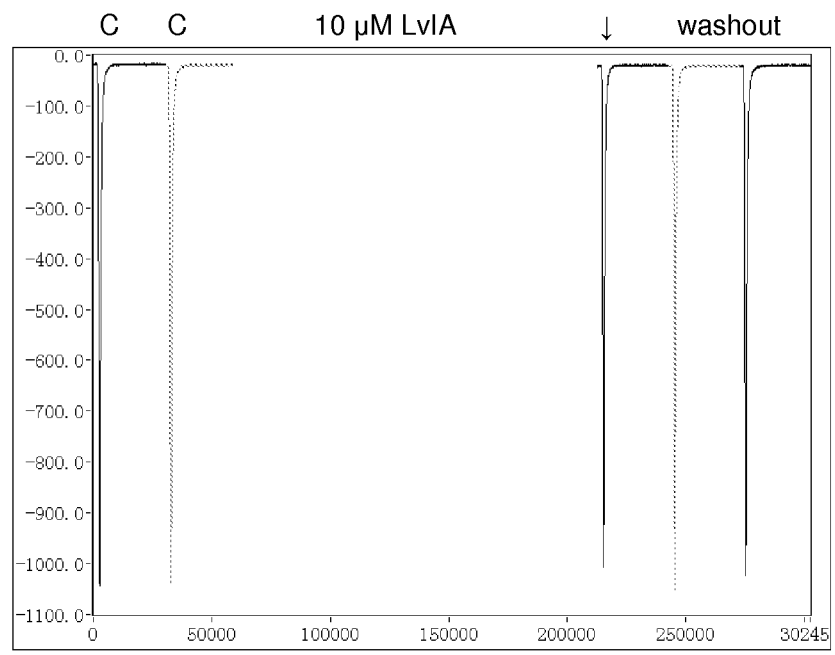
FIG. 4C shows effects of 10 μM α-LvIA/LvD21 on current of mice muscular (Mα1βδε) nAChRs.

It can be seen from the effects of 100 nM α-LvIA/LvD21 on electric current of α3β2 nAChRs (FIG. 4A), and effects of 10 μM α-LvIA/LvD21 on electric current of similar α2β2 (FIG. 4B) and Mα1β1δεα7 (FIG. 4C) nAChRs (FIG. 4), 100 nM α-LvIA/LvD21 completely blocks α3β2 nAChRs (FIG. 4A), while the toxin with 100 times higher concentration showed no blocking activity to α2β2, and Mα1β1δε nAChRs subtype (FIG. 4B-C).

Hence, α-LvIA/LvD21 is a novel α-conotoxin disclosed by the inventors, which shows very strong activity to α3β2 nAChRs, and is the first ligand with the best selectivity and discrimination for α3β2 vs. α6/α3β2β3.

Example 3-(2)

Experiments of α-Conotoxin TxIB and TxIB(G) in Specifically Blocking α6/α3β2β3 nAChRs The methods of document (Azam L, Yoshikami D, McIntosh J M. Amino acid residues that confer high selectivity of the alpha6 nicotinic acetylcholine receptor subunit to alpha-conotoxin MII[S4A,E11A,L15A]. J Biol Chem. 2008; 283 (17):11625-32.), the specification of in vitro transcription kit (mMessage mMachine in vitro transcription kit (Ambion, Austin, Tex.)) were referred to prepare cRNAs of various rat nervous type nAChRs subtypes, (α3β2, α6/α3β2β3 (i.e., α6β2*-nAChRs), α6/α3β4, α9α10, α4β2, α4β4, α3β4, α2β2, α2β4, α7), human α6/α3β2β3, and mice muscle type nAChRs (α1β1δε), their concentrations were measured and calculated by OD values under UV 260 nm. Oocytes (frogspawns) of Xenopus (Xenopus laveis) were collected and dissected, cRNA was injected into frogspawns with an injection dose of 5 ng cRNA for each subtype. For muscle nAChR, each subtype was injected with 0.5-2.5 ng DNA. The frogspawns were cultured in ND-96. The collected frogspawns were injected with cRNA within 1-2 days, and used for nAChRs voltage clamp recording within 1-4 days after the injection.

TABLE 1

$IC_{50}$ and hill slopes of dose-response curves of α-LvIA/LvD21 to various nAChRs subtypes

| Subtypes (receptor subtypes) | $IC_{50}$ (nM)[a] (half-blocking dose)[a] | Ratio[b] (ratio)[b] | Hill slope[a] (hill slope of dose-response curve)[a] |
|---|---|---|---|
| α3β2 | 8.69 (6.9-11.0) | 1 | 1.17 (0.88-1.46) |
| α6/α3β4 | 120.9 (86.1-169.8) | 14 | 0.94 (0.66-1.22) |
| α3β4 | 148.4 (103.2-213.2) | 17 | 1.14 (0.72-1.55) |
| α6/α3β2β3 | 852 (590-1230) | 98 | 0.60 (0.48-0.72) |
| α7 | 3000 (1797-4997) | 345 | 0.65 (0.43-0.87) |
| α2β4 | 15520 (11600-20770) | 1786 | 1.13 (0.78-1.48) |
| α9α10 | >10000 | — | — |
| α2β2 | >10000 | — | — |
| α4β2 | >10000 | — | — |
| α4β4 | >10000 | — | — |
| Mα1β1δε | >10000 | — | — |
| Hα3β2 | 17.5 (16.6-21.6) | 1[c] | 0.81 (0.44-1.18) |
| Hα6/3β2β3 | 5342 (1763-8921) | 305[c] | 0.85 (0.55-1.15) |

[a]Numbers in parentheses are 95% confidence intervals; [a] in the table refers to confidence interval with confidence degree of 95%.
[b]nAChR subtype $IC_{50}$/α3β2 $IC_{50}$; [b] refers to a ratio of half-blocking dose (IC50) between other subtype and α3β2 nAChRs.
[c]nAChR subtype IC50/Human α3β2 IC50; [c] refers to a ratio of half-blocking dose (IC50) between human α6/3β2β3 subtype and human α3β2 nAChRs.
"M" denotes mouse subunits used,
"H" denotes human subunits used.
"M" represents mouse,
"H" represents human.

It was shown in some researches that α3β2, α6/α3β4 and α3β4 nAChR are drug action targets for treatment of neuropsychological diseases, such as neuralgia, addiction, Parkinson's disease, dementia, schizophrenia, depression, fear, etc. (see relevant documents in the Background Art). Hence, the novel α-conotoxin LvIA/LvD21 of the present invention is extremely promising in areas of mechanism research, diagnosis and treatment of the above diseases.

One of the frogspawns injected with cRNA was placed in 30 uL of Sylgard record tank (diameter 4 mm×depth 2 mm), gravity perfused with ND96 perfusate (96.0 mM NaCl, 2.0 mM KCl, 1.8 mM $CaCl_2$, 1.0 mM $MgCl_2$, 5 mM HEPES, pH 7.1-7.5) containing 0.1 mg/ml BSA (bovine serum albumin), or ND96 (ND96A) containing 1 mM atropine, flow rate was 1 ml/min. All conotoxin solutions also contained 0.1 mg/ml BSA to reduce non-specific adsorption of toxin, a change-over valve (SmartValve, Cavro Scientific Instruments, Sunnyvale, Calif.) could be used for freely switching between perfusion of toxin and acetylcholine (ACh), and a series of three-way solenoid valves (solenoid valves, model 161TO31, Neptune Research, Northboro, Mass.) were used for freely switching between perfusion of ND96 and ACh. Ach gating current was set at "slow" clamp with double-electrode voltage clamp amplifier (model OC-725B, Warner Instrument Corp., Hamden, Conn.), and on-line recording of clamp gain was performed at the maximum value (×2000) position. Glass electrodes were drawn from glass capillaries (fiber-filled borosilicate capillaries, WPI Inc., Sarasota, Fla.) with 1 mm external diameter×0.75 mm internal diameter, and filled with 3 M KCl as voltage and current electrodes. Membrane voltage was clamped at −70 mV. The control of whole system and data recording were carried out with a computer. ACh pulse was to automatically perfuse ACh for 1 s per interval of 5 min. ACh had concentration of 10 μM for oocyte expression of muscle type nAChRs and nervous type α9α10 nAChRs; 200 μM for α7 of nervous type nAChRs, and 100 μM for other subtypes. At least 4 oocytes were used for recording situations of current response and current tracks of a subtype under different toxin concentrations.

The measured current data were subjected to statistic analysis with GraphPad Prism software (San Diego, Calif.), dose-response curves were plotted, half-blocking concentration ($IC_{50}$) of conotoxin and many other parameters relating to toxin-blocking nAChRs were calculated.

Figures 11A, 11B, 12A:
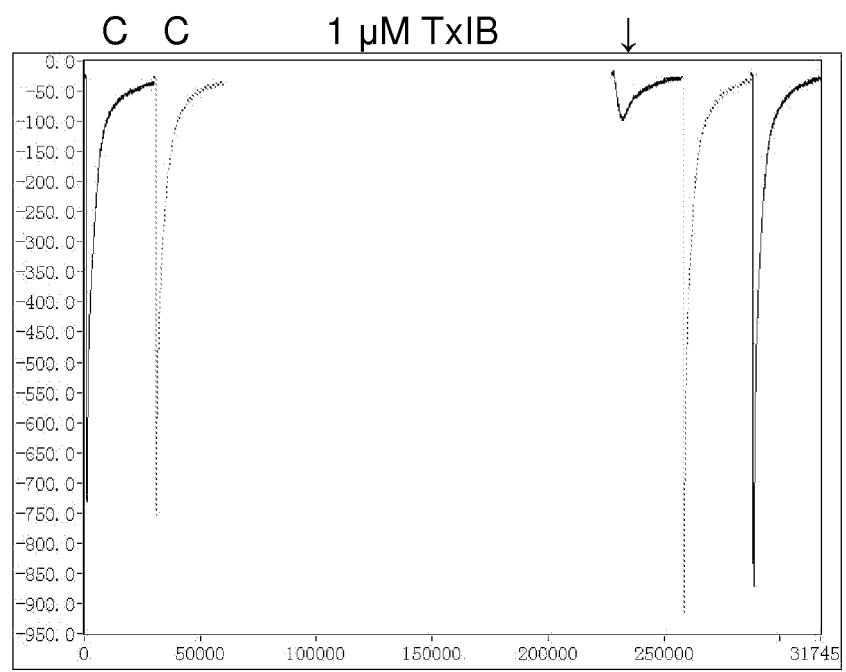
FIG. 12A shows effects of 1 µM α-TxIB on current of α6/α3β2β3 nAChR.
Figure 12B:
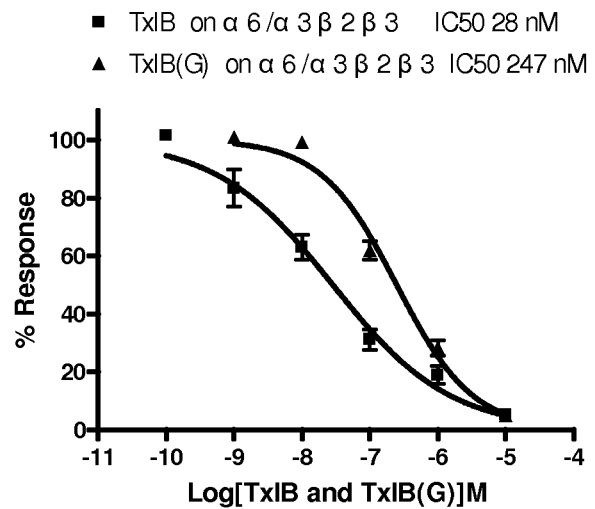
FIG. 12B shows dose-response curves of α-TxIB and TxIB(G) to α6/α3β2β3 nAChR, in the figure the abscissa is log value (Log [TxIB and TxIB(G)]M) of molar concentration (M) of the used α-TxIB and TxIB(G); the ordinate is dose-response percentage (% Response), which is a ratio percentage of acetylcholine receptor current to the control current under action of corresponding concentration of toxin.
Figure 12C:
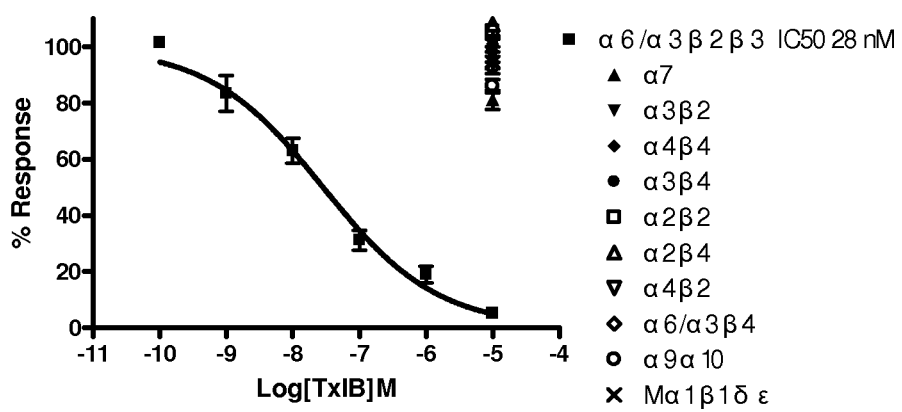
FIG. 12C shows dose-response curves of α-TxIB to various nAChRs subtypes, α-TxIB specifically blocks α6/α3β2β3 nAChR, which half-blocking dose (IC50) is 28 nM, and under 10 µM of toxin, TxIB has no blocking effect to other subtypes, which IC50>10 µM. In the figure, the values are mean values of currents obtained from 3-5 Xenopus oocytes.

The results shown that both α-TxIB and TxIB(G) (as prepared in Example 2-(2)) showed blocking effect on rat α6/α3β2β3 nAChR, and had feature of fast elution (FIG. 12). 1 μM α-TxIB/Txd4 almost total blocked the current generated by Ach-gated ratα6/α3β2β3 nAChR open, and could be rapidly eluted, and this blocking was reversible (FIG. 12A). In comparison, the activity of α-TxIB was 8.7 times higher than that of TxIB(G) (FIG. 12B), and their half-blocking doses $IC_{50}$ and error ranges for α6/α3β2β3 nAChRs were separately: α-TxIB, 28.4 (18.6-43.4) nM; α-TxIB(G), 247.4 (186.2-328.8) nM. Their hill slopes of dose-response curves and error ranges were separately: α-TxIB, 0.51 (0.41-0.60) and α-TxIB(G), 0.78 (0.63-0.93). Hence, α-TxIB and TxIB(G) showed no blocking activity on other nAChRs subtypes, and their IC50>10 μM (FIG. 12C, Table 2).

TABLE 2

Half-blocking dose IC50 and hill slopes of dose-response curves of α-TxIB and TxIB(G) to various nAChRs subtypes

| Polypeptide | Subtype | $IC_{50}$ (nM)[a] | Ratio[b] | Hill slope[a] |
|---|---|---|---|---|
| TxIB | α6/α3β2β3 | 28.41 (18.6-43.4) | 1 | 0.51 (0.41-0.60) |
| TxIB(G) | α6/α3β2β3 | 247.4 (186.2-328.8) | 8.7 | 0.78 (0.63-0.93) |
| TxIB | α6/α3β4 | >10000[c] | — | — |
| TxIB(G) | α7 | >10000 | — | — |
|  | α9α10 | >10000 | — | — |
|  | Mα1β1δε | >10000 | — | — |
|  | α2β2 | >10000 | — | — |
|  | α2β4 | >10000 | — | — |
|  | α3β2 | >10000 | — | — |
|  | α3β4 | >10000 | — | — |
|  | α4β2 | >10000 | — | — |
|  | α4β4 | >10000 | — | — |

In Table 2,
[a] refers to confidence interval with confidence degree of 95%;
[b] refers to a ratio of half-blocking dose (IC50) between TxIB(G) and TxIB.
[c] refers to showing no blocking activity under 10 μM.

Figure 13A:
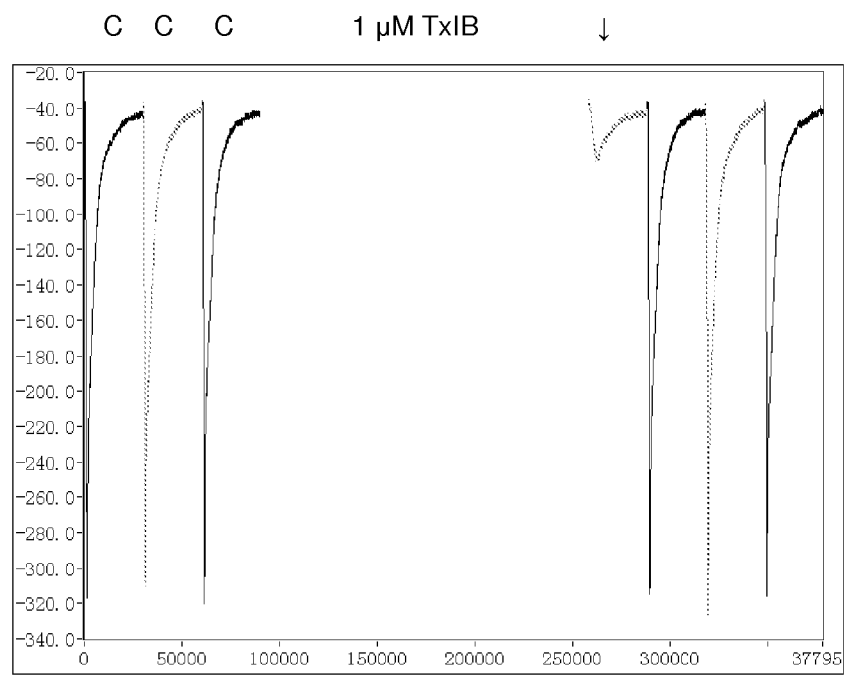
FIG. 13: shows the effects of 1 µM α-TxIB to current of α6/α3β2β3 nAChR (FIG. 13A), and 10 µM α-TxIB to current of very close α3β2 (FIG. 13B), α6/α3β4 (FIG. 13C), α3β4 (FIG. 13D) nAChRs. In the figure, "C" refers to control current, and it closely follows "C" is toxin concentration of α-TxIB. The arrow indicates the current trace formed by the first Ach pulse that TxIB blocks corresponding receptor subtype after 5 min of incubation. 1 µM α-TxIB specifically blocks α6/α3β2β3 nAChR (FIG. 13A), while 10 µM totally does not block α3β2 (FIG. 13B), α6/α3β4 (FIG. 13C) and α3β4 (FIG. 13D) nAChRs subtypes.
Figure 13B:
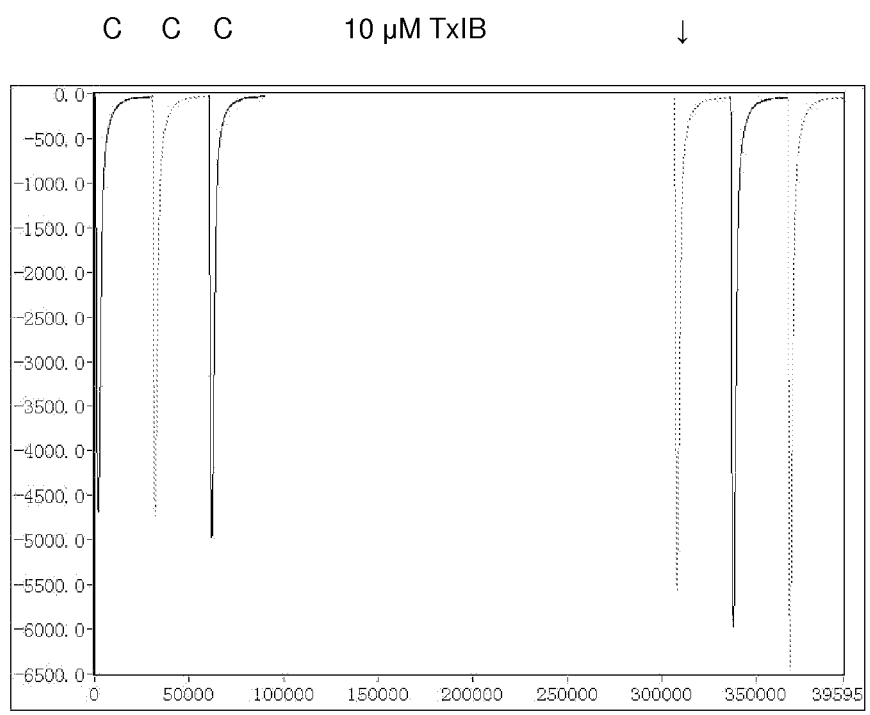
Figure 13C:
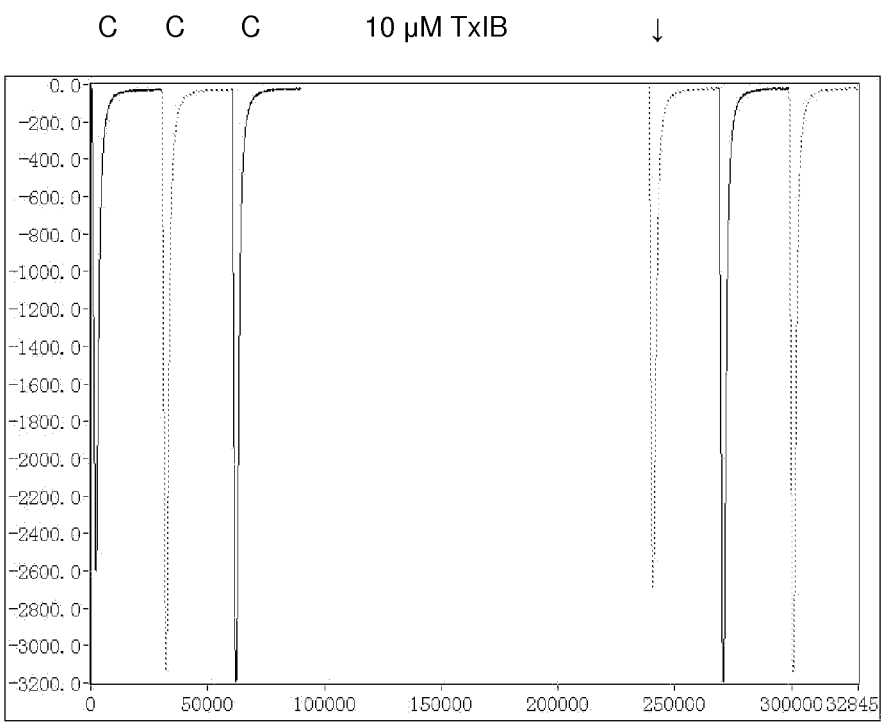
Figure 13D:
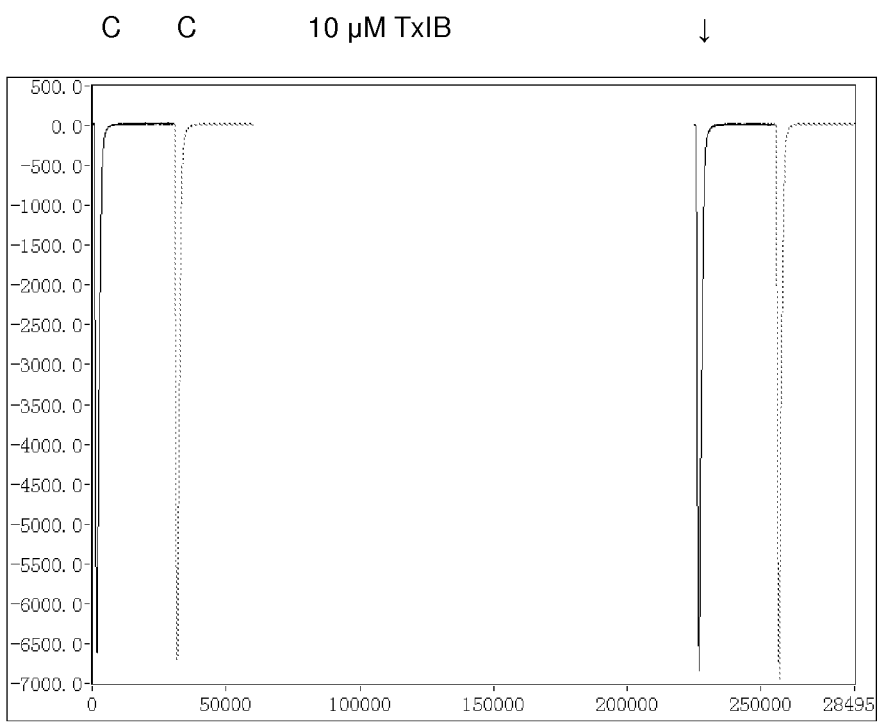

The α-TxIB/Txd4 shows a high selectivity in blocking α6/α3β2β3 nAChR. It can be seen from the effects of 1 μM α-TxIB/Txd4 on current of α6/α3β2β3 nAChR, and effects of 10 μM α-TxIB/Txd4 on currents of very similar α3β2(B), α6/α3β4(C), α3β4(D) nAChRs (FIG. 13), 1 μM α-TxIB/Txd4 specifically blocked α6/α3β2β3 nAChR (FIG. 13A), while the toxin with 10 times higher concentration showed no blocking activity to α3β2 (FIG. 13B), α6/α3β4 (FIG. 13C), and α3β4 (FIG. 13D) nAChRs subtypes. As for human α6/α3β2β3 nAChR, α-TxIB and TxIB(G) had blocking activity similar to those for rat α6/α3β2β3 nAChR. Hence, α-TxIB is an α-conotoxin with the best selectivity to α6/α3β2β3 nAChR, the comparison of activity is shown in Table 3.

Some existing researches show that α6/α3β2β3 nAChR is drug action target for treatment of neuropsychological diseases, such as addictions to nicotine, morphine and cocaine, Parkinson's disease, dementia, schizophrenia, depression, etc. (see relevant documents in the Background Art). Hence, the novel α-conotoxin TxIB/Txd4 and TxIB(G) of the present invention are extremely promising in areas of mechanism research, diagnosis and treatment of the above diseases.

The comparisons of sequences and activities of TxIB/Txd4 and TxIB/Txd4(G) with other α-CTx are shown in Table 3.

TABLE 3

Comparison sequences and activities of α-TxIB and other α-conotoxin precursor proteins

| Polypeptide (superfamily) | Species | Precursor peptide (pro-peptide) sequence | | nAChRs selectivity |
|---|---|---|---|---|
| | | Signal peptide (lower case), N-terminal pro-peptide regions (pro-regions) (upper case) | Mature peptide (UPPER CASE) (*, C-terminal amidation) | |
| TxIB (α4/7) | C. textile | FDGRNTSANNKATDLMALPVR↓ (SEQ ID NO: 32) | GCCSDPPCRNKHPDLC*ggrr (SEQ ID NO: 33) | α6/α3β2β3 (α6β2*-nAChRs) |
| TxIA (α4/7) | C. textile | mftvfllvvlatavvs FTSDRASDDGKAAASDLITLTIK↓ (SEQ ID NO: 34) | GCCSRPPCIANNPDLC*g (SEQ ID NO: 35) | α3β2 > α7 |
| MII (α4/7) | C. magus | mgmrmmftvfllvvlattvvsFPSD RASDGRNAAANDKASDVITLALK↓ (SEQ ID NO: 36) | GCCSNPVCHLEHSNLC* grrr (SEQ ID NO: 37) | α3β2 > α6/α3β2β3 > α7 |
| LtIA (α4/7) | C. litteratus | mgmrmmfimfmlvvlattvvtftsD RALDAMNAAASNKASRLIALAVR↓ (SEQ ID NO: 38) | GCCARAACAGIHQELC*g ggr (SEQ ID NO: 39) | α3β2 > α6/α3β2β3 |

TABLE 3-continued

Comparison sequences and activities of α-TxIB and other α-conotoxin precursor proteins

| | | Precursor peptide (pro-peptide) sequence | | |
|---|---|---|---|---|
| Polypeptide (superfamily) | Species | Signal peptide (lower case), N-terminal pro-peptide regions (pro-regions) (upper case) | Mature peptide (UPPER CASE) (*, C-terminal amidation) | nAChRs selectivity |
| PIA (α4/7) | C.purpurascens | mftvfllvvlattvgsFTLDRASDGR DAAANDKATDLIALTAR↓ (SEQ ID NO: 40) | RDPCCSNPVCTVHNPQI C*g (SEQ ID NO: 41) | α6/α3β2β3 > α6/ α3β4 > α3β2 > α3β4 |
| GIC (α4/7) | C.geographus | SDGRNDAAKAFDLISSTVKK↓ (SEQ ID NO: 42) | GCCSHPACAGNNQHIC*grrr (SEQ ID NO: 43) | α3β2 > α4β2 > α3β4 |
| PnIB (α4/7) | C.pennaceus | mgmrmmftvfllvvlattvvsFTSD RASDDGNAAASDLIALTIK↓ (SEQ ID NO: 44) | GCCSLPPCALSNPDYC*g (SEQ ID NO: 45) | α7 > α3β2 |
| SrIA/SrIB (α4/7) | C. spurius | mgmrmmftvfllvvlattvvsFTSD SAFDSRNVAANDKVSDMIALTAR↓ (SEQ ID NO: 46) | RTCCSRPTCRMEYPELC*grr (SEQ ID NO: 47) | Muscle nAChR/α4β2 |
| Vc1.1 (α4/7) | C. victoriae | mgmrmmftvfllvvlattvvsSTSG R REFRGRNAAAKASDLVSLTDKKR↓ (SEQ ID NO: 48) | GCCSDPRCNYDHPEIC*g (SEQ ID NO: 49) | α9α10 >> α6/ α3β2β3 > α6/α3β4 > α3β4~α3β2 |
| AuIB (α4/6) | C. aulicus | MFTVFLLVVLATTVVSFTSDRASDGR KDAASGLIALTMK↓ (SEQ ID NO: 50) | GCCSYPPCFATNPD-C*grrr (SEQ ID NO: 51) | α3β4 > α3β2 |
| BuIA (α4/4) | C. bullatus | mftvfllvvltttvvsFPSDRASDGR NAAANDKASDVVTLVLK↓ (SEQ ID NO: 52) | GCCSTPPCAVLY---C*grrr (SEQ ID NO: 53) | α6/α3β2β3 > α6/ α3β4 > α3β2 > α3β4 |
| RgIA (α4/3) | C. regius | SNKRKNAAMLDMIAQHAIR↓ (SEQ ID NO: 54) | GCCSDPRCRYR----CR (SEQ ID NO: 55) | α9α10 |
| Ac1.1a (α3/5) | C.achatinus | mgmrmmftlfllvvltttvvsYPSD SASDGRDDEAKDERSDMYELKR (SEQ ID NO: 56) | NGRCC-HPACGKHFN--C* gr (SEQ ID NO: 57) | Muscle nAChR |

In the table, asterisk (*) represents C-terminal amidation.
Short line (-) represents gap.

Example 3-(3)

Experiment of Specifically Blocking α3β4 and α6/α3β4 nAChRs with α-Conotoxin TxIC The methods of document (Azam L, Yoshikami D, McIntosh J M. Amino acid residues that confer high selectivity of the alpha6 nicotinic acetylcholine receptor subunit to alpha-conotoxin MII[S4A,E11A,L15A]. *J Biol Chem*. 2008; 283 (17):11625-32.), the specification of in vitro transcription kit (mMessage mMachine in vitro transcription kit (Ambion, Austin, Tex.)) were referred to prepare cRNAs of various rat nervous type nAChRs subtypes (α3β4, α6/α3β4, α9α10, α4β2, α4β4, α3β4, α2β2, α2β4, α7), human α3β4, and mice muscle type nAChRs (α1β1δε), their concentrations were measured and calculated by OD values under UV 260 nm. Oocytes (frogspawns) of *Xenopus* (*Xenopus laveis*) were collected and dissected, cRNA was injected into frogspawns with an injection dose of 5 ng cRNA for each subtype. For muscle nAChR, each subtype was injected with 0.5-2.5 ng DNA. The frogspawns were cultured in ND-96. The collected frogspawns were injected with cRNA within 1-2 days, and used for nAChRs voltage clamp recording within 1-4 days after the injection.

One of the frogspawns injected with cRNA was placed in 30 uL of Sylgard record tank (diameter 4 mm×depth 2 mm), gravity perfused with ND96 perfusate (96.0 mM NaCl, 2.0 mM KCl, 1.8 mM $CaCl_2$, 1.0 mM $MgCl_2$, 5 mM HEPES, pH 7.1-7.5) containing 0.1 mg/ml BSA (bovine serum albumin), or ND96 (ND96A) containing 1 mM atropine, flow rate was 1 ml/min. All conotoxin solutions also contained 0.1 mg/ml BSA to reduce non-specific adsorption of toxin, a change-over valve (SmartValve, Cavro Scientific Instruments, Sunnyvale, Calif.) could be used for freely switching between perfusion of toxin and acetylcholine (ACh), and a series of three-way solenoid valves (solenoid valves, model 161TO31, Neptune Research, Northboro, Mass.) were used for freely switching between perfusion of ND96 and ACh. Ach gating current was set at "slow" clamp with double-electrode voltage clamp amplifier (model OC-725B, Warner Instrument Corp., Hamden, Conn.), and on-line recording of clamp gain was performed at the maximum value (×2000) position. Glass electrodes were drawn from glass capillaries (fiber-filled borosilicate capillaries, WPI Inc., Sarasota, Fla.) with 1 mm external diameter×0.75 mm internal diameter, and filled with 3 M KCl as voltage and current electrodes. Membrane voltage was clamped at −70 mV. The control of whole system and data recording were carried out with a computer. ACh pulse was to automatically perfuse ACh for 1 s per interval of 5 min. ACh had concentration of 10 μM for oocyte expression of muscle type nAChRs and nervous type α9α10 nAChRs; 200 μM for α7 of nervous type nAChRs, and 100 μM for other subtypes. At least 4 oocytes were used for recording situations of current response and current tracks of a subtype under different toxin concentrations.

The measured current data were subjected to statistic analysis with Graph Pad Prism software (San Diego, Calif.), dose-response curves were plotted, half-blocking concentration ($IC_{50}$) of conotoxin and many other parameters relating to toxin-blocking nAChRs were calculated.

The results show that TxIC (as prepared in Example 2-(3)) showed specific blocking activity to α3β4 nAChR, which could be rapidly eluted (FIG. 16). TxIC is the strongest blocking agent for α3β4 nAChR, which half-blocking dose $IC_{50}$ was only 12.5 nM, and comparison of activity with other known conotoxins were shown in Table 4.

Figure 16A:
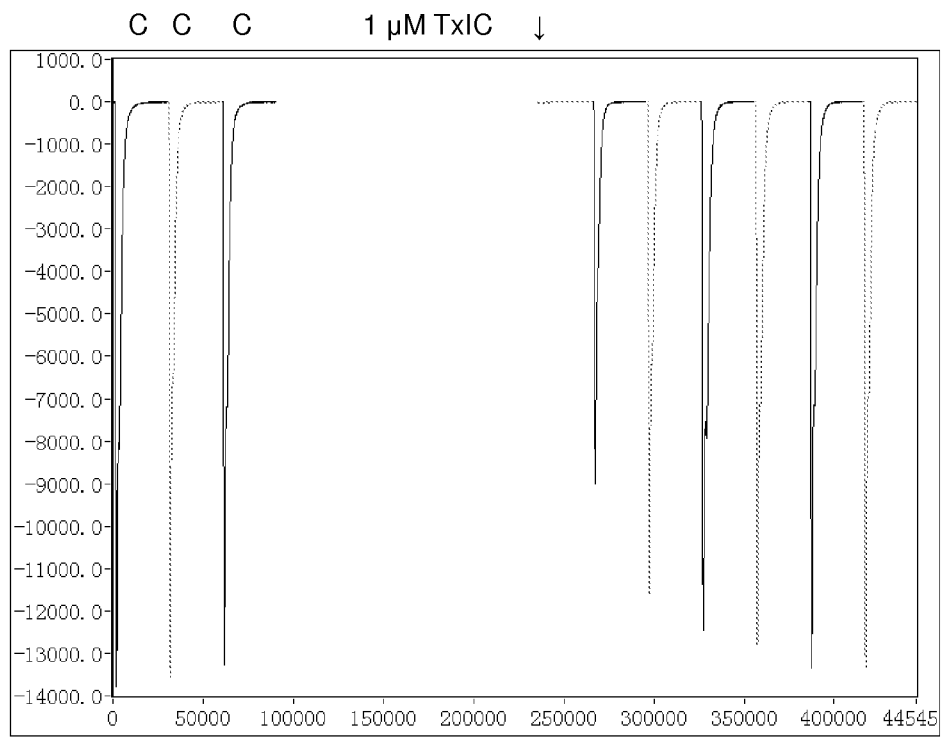
FIG. 16: shows α-TxIC is a selective potent blocking agent to α3β4 nAChR. A shows the effects of 1 μM α-TxIC on current of α3β4 nAChR. In Fig.A, "C" refers to the control current, the arrow indicates the current trace (~0 nA) formed by the first Ach pulse after 5 min of incubation with 1 μM α-TxIC. B shows dose-response curves of α-TxIC to other 10 nAChRs subtypes, in which the abscissa is log value (Log [TxIC]M) of molar concentration (M) of the used α-TxIC; the ordinate is dose-response percentage (% Response), which is a ratio percentage of acetylcholine receptor current to the control current under action of corresponding concentration of toxin. α-TxIC specifically blocks α3β4 nAChR, which half-blocking dose ($IC_{50}$) is merely 12.5 nM; α-TxIC also shows blocking activity to α6/α3β4 nAChR in some extent, which half blocking dose ($IC_{50}$) is 94 nM; α-TxIC shows very weak blocking activity to α2β4 nAChR, which half blocking dose is up to 4550 nM. Under 10 μM toxin concentration, TxIC shows no blocking activity to other subtypes, which $IC_{50}$>10 μM. The values in figure are mean values of current obtained from 3-8 *Xenopus* oocytes.
Figure 16B:
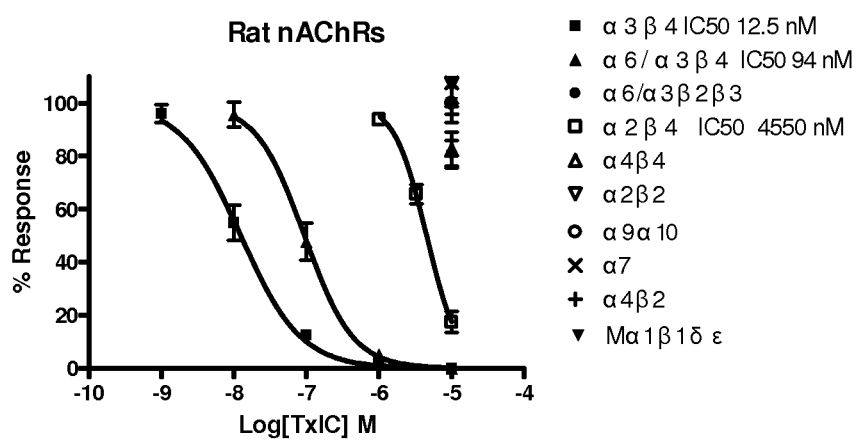

1 μM α-TxIC/Txd1 completely blocked the current generated by Ach-gated rat α3β4 nAChR open, and could be rapidly eluted, and this blocking was reversible (FIG. 16A). TxIC showed the strongest blocking activity to α3β4 nAChR, which half-blocking dose and error range thereof were: 12.5 nM (9.4-16.5 nM); the blocking activity of TxIC to α6/α3β4 nAChR took the second place, showing half-blocking dose $IC_{50}$ and error range as 94.1 nM (73-121 nM); the blocking activity of TxIC to α2β4 nAChR was very weak, showing half-blocking dose $IC_{50}$ and error range as 4550 nM (3950-5230 nM). The hill slopes of dose-response curves and error ranges of TxIC against them were separately: α3β4 nAChR, 0.19 (0.66-1.44); α6/α3β4 nAChR, 0.26 (0.73-1.87); α2β4 nAChR, 0.20 (1.48-2.42). The α-TxIC showed no blocking activity to other nAChRs subtypes, including α4β4, α4β2, α6/α3β2β3, α2β2, α9α10, α7, α1β1δε, in which $IC_{50}$>10 μM (FIG. 16B, Table 5), in comparison, α-TxIC showed a blocking activity to α3β4 7.5 times higher than that to α6/α3β4, and 524 times higher than that to α2β4 (FIG. 16B, Table 5).

Figure 17:
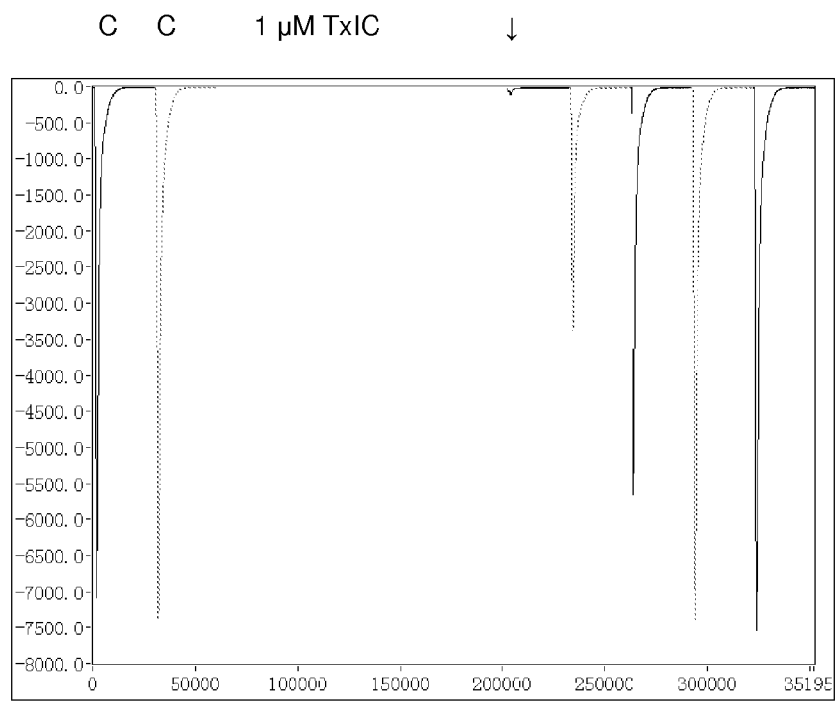
FIG. 17: shows effects of 1 μM α-TxIC to current of α3β4 nAChR(A), and 10 μM α-TxIC to current of very close α4β4(B), α7(C) nAChRs. In the figure, "C" refers to the control current, it closely following "C" is toxin concentration of α-TxIC. The arrow indicates the current trace formed by the first Ach pulse that TxIC blocks corresponding receptor subtype after 5 min of incubation. 1 μM α-TxIC specifically blocks α3β4 nAChR, while 10 μM totally does not block α4β4(B) and α7(C) nAChRs subtypes.
Figure 17:
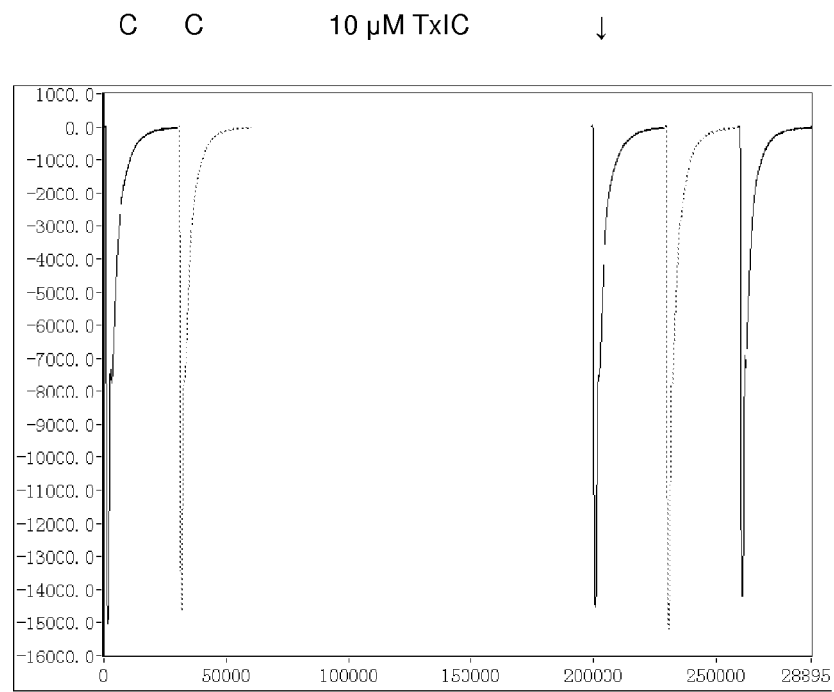
Figure 17:
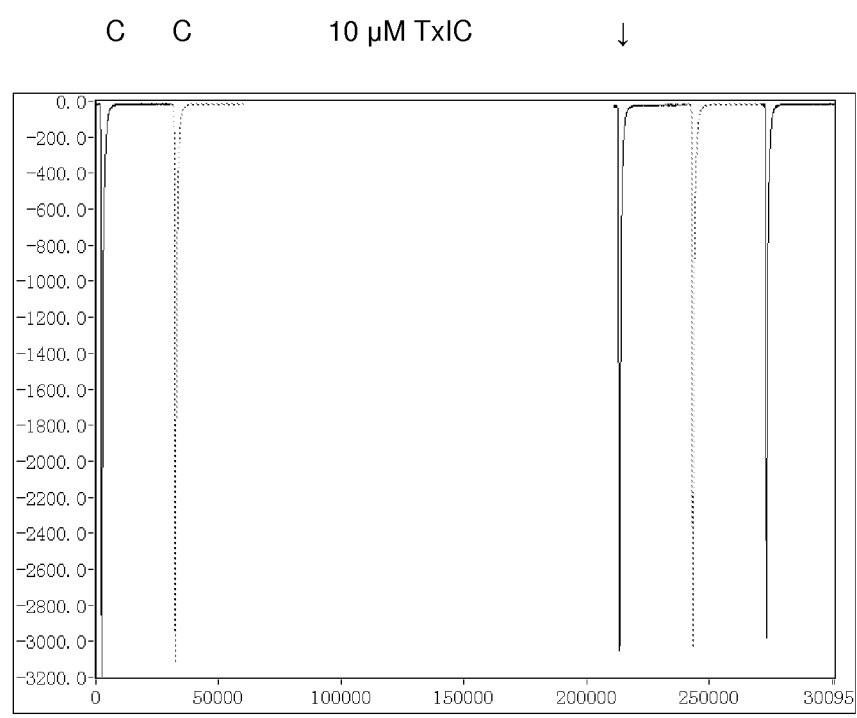

The α-TxIC/Txd1 showed high selectivity in blocking α3β4 nAChR. It can be seen from the effects of 1 μM α-TxIC/Txd1 on current of α3β4 nAChR, and effects of 10 μM α-TxIC/Txd1 on currents of very similar α4β4 (B), α7(C) nAChRs (FIG. 17), 1 μM α-TxIC/Txd1 specifically blocked α3β4 nAChR (FIG. 17A), while the toxin with 10 times higher concentration showed no blocking activity to α4β4 (FIG. 17B), and α7 (FIG. 17C) nAChRs subtypes. As for human α3β4 nAChR, α-TxIC showed similar blocking activity to that for rat α3β4 nAChR.

Hence, α-TxIC is α-conotoxin with the strongest activity to α3β4 nAChR as found so far, and also shows relatively strong blocking activity to α6/α3β4 nAChR, and the comparison of activities thereof was shown in Table 4.

TABLE 4

Comparison of sequences and activities of α-TxIC and other α-conotoxins

| Sub-type | poly-peptide | Species | Sequence | Target activity of acting on acetylcholine receptor (half-blocking dose $IC_{50}$ [nM]) |
|---|---|---|---|---|
| α4/6 | TxIC | C. textile | GCCSHPVCSAMSP-IC* (SEQ ID NO: 58) | α3β4 (12.5 nM) > α6/α3β4 (94 nM) > α2β4 (4550 nM) |
|  | AuIB | C. aulicus | GCCSYPPCFATNP-DC* (SEQ ID NO: 59) | α3β4 (750 nM) > α7 |
| α4/4 | BuIA | C. bullatus | GCCSTPPCAVLY---C* (SEQ ID NO: 60) | α6/α3β2β3 (0.26-0.46 nM) > α6/α3β4 (1.54-2.1 nM) > α3β2 (5.72 nM) > α3β4 (27.7 nM > α4β4 (69.9 nM) > α2β4 (121 nM ) > α7 (272 nM) |
| α4/3 | ImI | C. imperialis | GCCSDPRCAWR----C* (SEQ ID NO: 61) | α3β2(41 nM) > α7/5HT3 chimera (217 nM) > α7(595 nM) α9α10 (2000 nM) > α3β4 (3390 nM) |
| α4/7 | RegIIA | C. regius | GCCSHPACNVNNPHIC* (SEQ ID NO: 62) | α3β2 (33 nM) > α3β4 (97 nM) > α7 (103 nM) > α9α10 |
|  | PeIA | C. pergrandis | GCCSHPACSVNHPELC* (SEQ ID NO: 63) | α9α10 (6.9-54.9 nM) > α3β2 (23-97.5 nM) > α3β4 (480 nM) > α7 (1800 nM) |
|  | PIA | C. purpurascens | RDPCCSNPVCTVHNPQIC* (SEQ ID NO: 64) | α6/α3β2β3 (1-1.7 nM) > α6/α3β4(12.6-30.5 nM) > α3β2(74.2 nM) > α3β4 (518 nM) |
|  | Vc1.1 | C. victoriae | GCCSDPRCNYDHPEIC* (SEQ ID NO: 65) | α9α10 (19 nM) > α6/α3β2β3 (140 nM) > α6/α3β4 (980 nM) > α3β4 (4200 nM) > α3β2 (7300 nM) |
|  | GIC | C. geographus | GCCSHPACAGNNQHIC* (SEQ ID NO: 66) | α3β2 (1.1 nM) > α4β2 (309 nM) > α3β4 (755 nM) |

In the table, asterisk (*) represents C-terminal amidation.
Short line (-) represents gap.

TABLE 5

Half-blocking dose $IC_{50}$ and hill slopes of dose-response curves of α-TxIC to various nAChRs subtypes

| Subtype | $IC_{50}$ (nM)[a] | Ratio[b] | Hill slope[a] | subtype | $IC_{50}$ (nM)[c] |
|---|---|---|---|---|---|
| α3β4 | 12.5 (9.4-16.5) | 1 | 0.19 (0.66-1.44) | α6/α3β2β3 | >10000 |
| α6/α3β4 | 94.1 (73-121) | 7.5 | 0.26 (0.73-1.87) | α2β2 | >10000 |
| α2β4 | 4550 (3950-5230) | 524 | 0.20 (1.48-2.42) | α9α10 | >10000 |
| α4β4 | >10000 | — | — | α7 | >10000 |
| α4β2 | >10000 | — | — | α1β1δε | >10000 |

In Table 2,
[a] refers to confidence interval with confidence degree of 95%;
[b] refers to a ratio of half-blocking dose (IC50) between other subtypes and α3β4 nAChR;
[c] refers to showing no blocking activity under 10 μM.

Some existing researches show that α3β4, α6/α3β4 nAChRs are drug action targets for treatment of neuropsychological diseases, such as addictions to nicotine, morphine and cocaine, neuralgia, Parkinson's disease, dementia, schizophrenia, depression, fears etc. (see relevant documents in the Background Art). Hence, the novel α-conotoxin TxIC/Txd1 of the present invention are extremely promising in areas of mechanism research, diagnosis and treatment of the above diseases.

Example 4

Experiment of Blocking α3β2 nAChRs Mutants with α-Conotoxin LvIA/LvD21

Figure 5A:
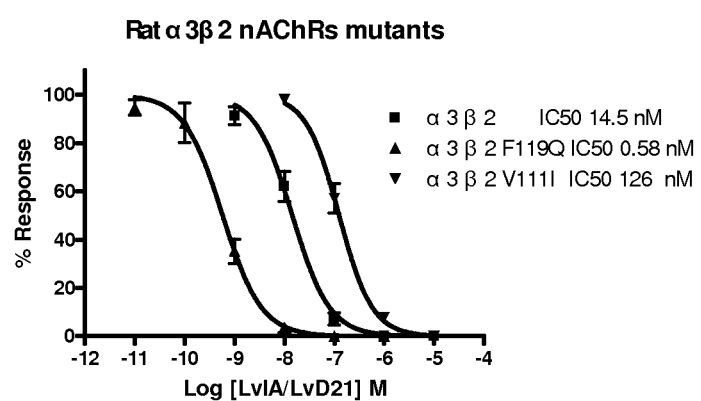
FIG. 5: shows dose-response curves of α-LvIA/LvD21 against α3β2 nAChRs and 7 β2 mutants thereof. The mutants in FIG. 5A are α3β2[F119Q], α3β2[V111I]; the mutants in FIG. 5B are α3β2[F119Q], α3β2[T59K], α3β2[T59L]; and the mutants in FIG. 5C are α3β2[T59I], α3β2[K79A], α3β2[Q34A].
Figure 5B:
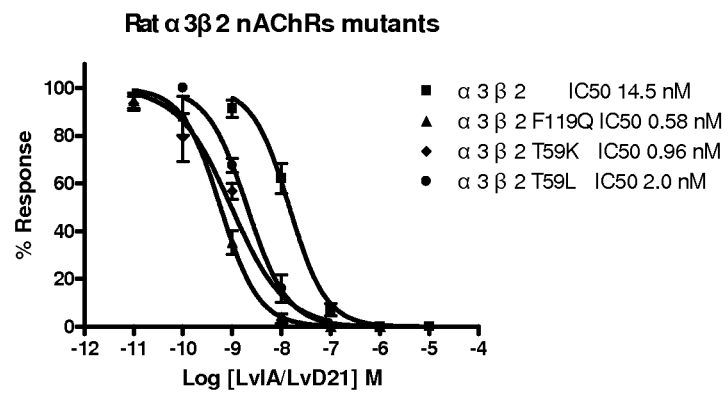
Figure 5C:
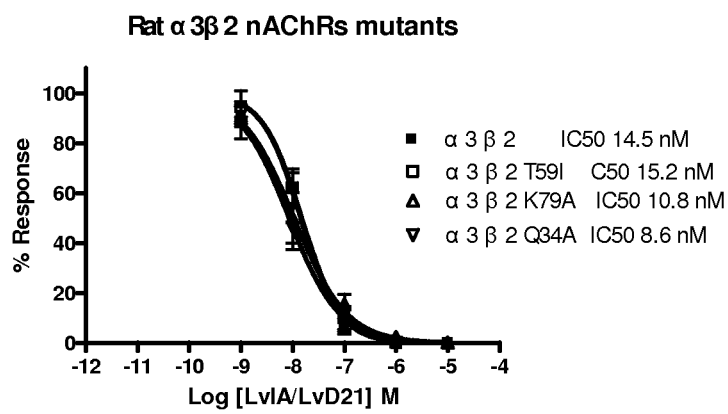
Figure 6A:
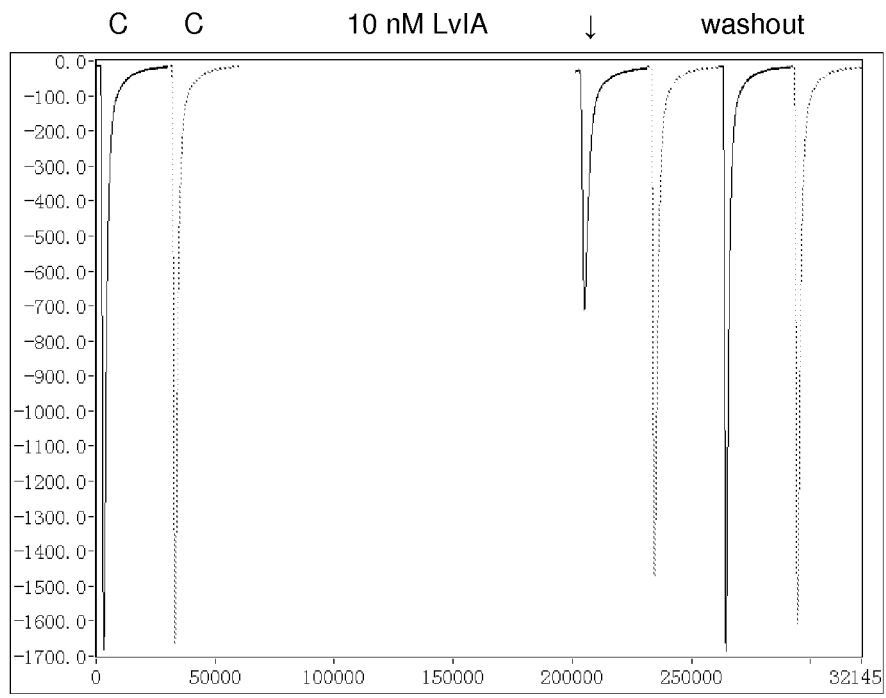
FIG. 6A shows 10 nM α-LvIA/LvD21 blocks about 50% current of α3β2 nAChRs wild type, in which elution rate is relatively great, and the current is completely recovered within 2 min of elution.
Figure 6B:
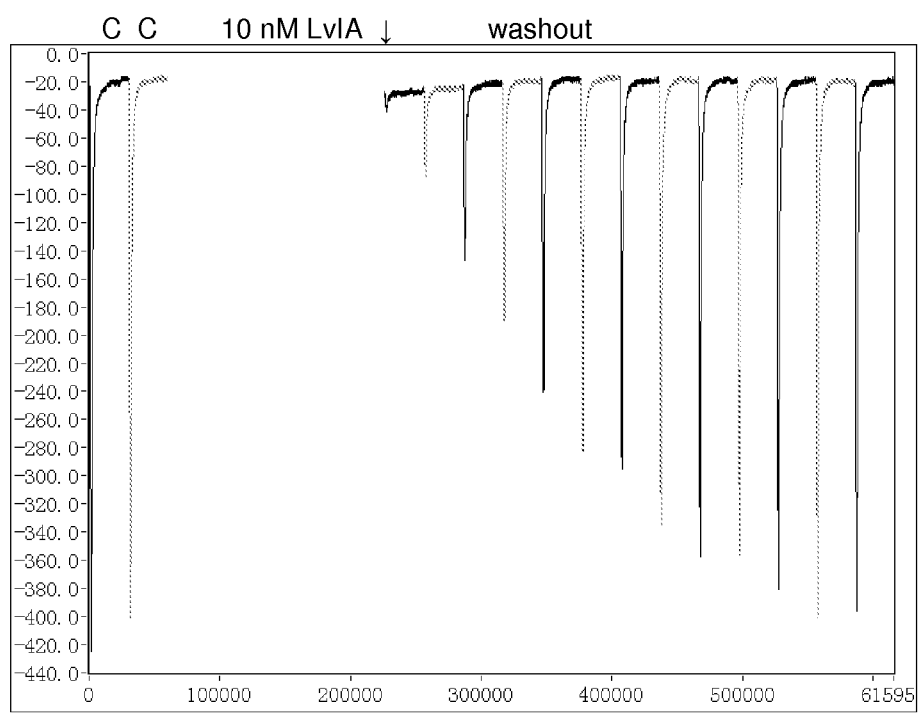
FIG. 6B shows 10 nM α-LvIA/LvD21 blocks all current of mutant α3β2[F119Q], in which elution rate is small, and the current is recovered after 12 min of elution.
Figure 6C:
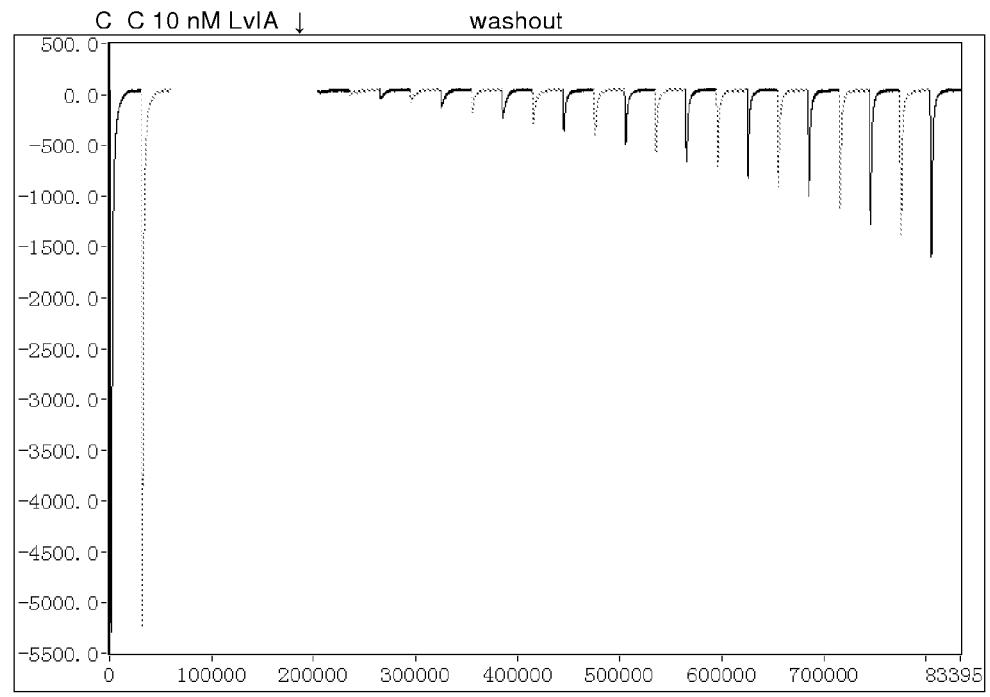
FIG. 6C shows 10 nM α-LvIA/LvD21 blocks all current of mutant α3β2[T59K], in which elution rate is very small, and the current is recovered to 27% of the control current after 20 min of elution.
Figure 6D:
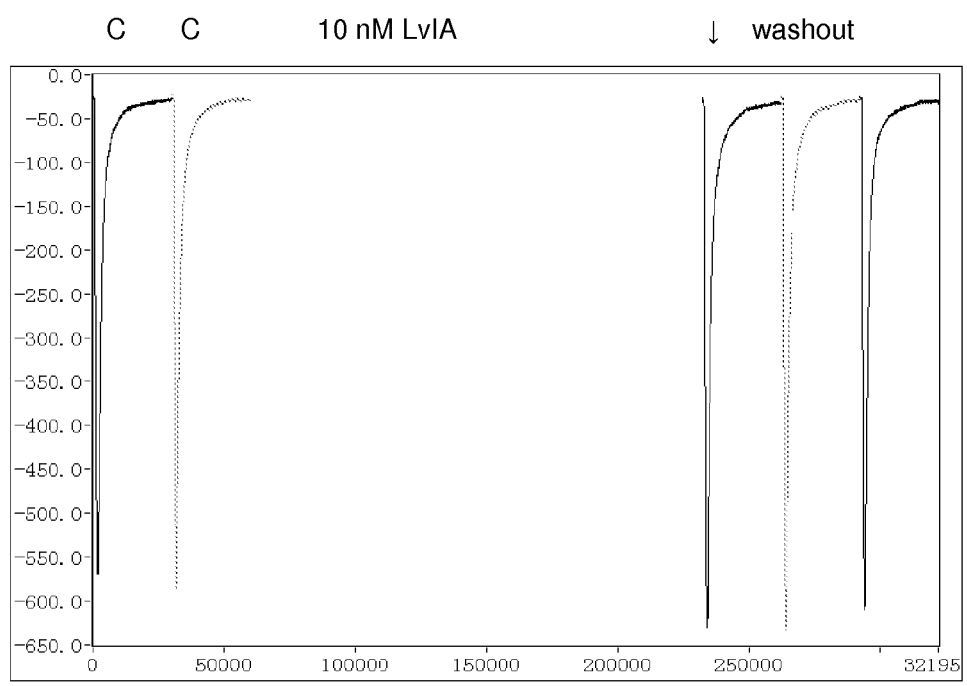
FIG. 6D shows 10 nM α-LvIA/LvD21 does not block at all the current of mutant α3β2[V111I].
Figure 7:
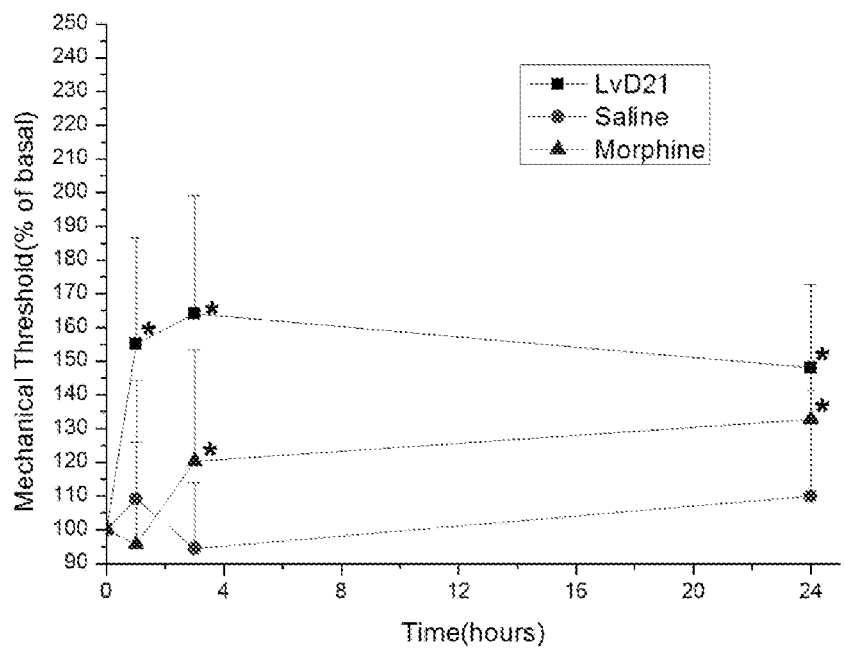
FIG. 7: shows analgesic effects of α-LvIA/LvD21 after intraperitoneal administration (IP) for 1-24 h in CCI model. In the figure, the negative control Saline is physiological saline (Saline), the positive control is morphine (Morphine), which dose is 1 mg/kg rat body weight; the dose of α-LvIA/LvD21 is 1 nmol/kg rat body weight. In the figure, the abscissa Time (hours) is number of hours after administration; the ordinate Mechanical Threshold is a percentage of observed pain threshold to basic pain threshold (100) (% of basal), the ordinate values of points in the figure are mean values and standard errors (Mean±SD). The comparison probability of significant difference is #p<0.05, and number of rats in each group is 8 (n=8).
Figure 8:
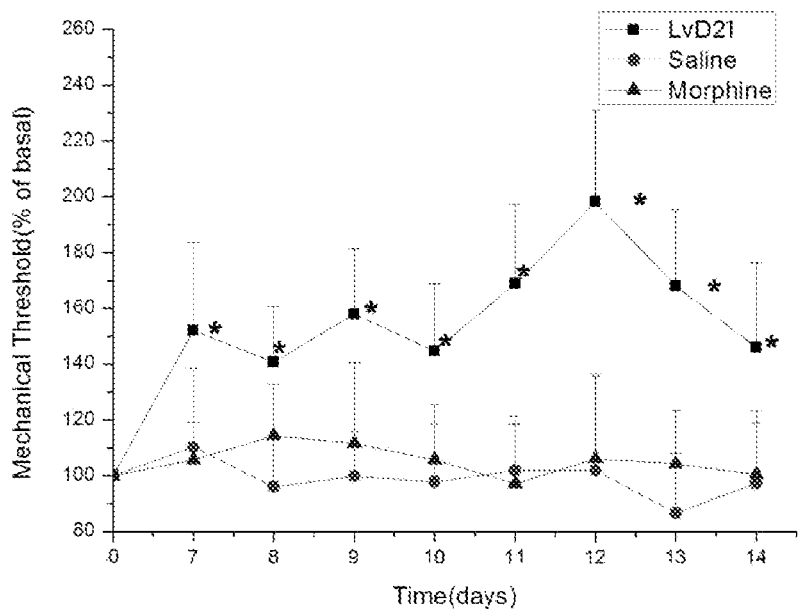
FIG. 8: shows analgesic effects of α-LvIA/LvD21 after intraperitoneal administration (IP) for 7-14 days in CCI model. In the figure, the negative control Saline is physiological saline (Saline), the positive control is morphine (Morphine), which dose is 1 mg/kg rat body weight; the dose of α-LvIA/LvD21 is 1 nmol/kg rat body weight. In the figure, the abscissa Time (days) is number of days after administration; the ordinate Mechanical Threshold is a percentage of observed pain threshold to basic threshold (100) (% of basal), the ordinate values of points in the figure are mean values and standard errors (Mean±SD). The comparison probability of significant difference is #p<0.05, and number of rats in each group is 8 (n=8).

The α-CTx LvIA/LvD21 showed great diverse in blocking activities to 7 β2 mutants of α3β2 nAChR: α3β2[T59K], α3β2[T59L], α3β2[T59I], α3β2 [V111I], α3β2[F119Q], α3β2 [Q34A], α3β2 [K79A] (FIG. 6-7; FIG. 5-6), and in these 7 mutants, the key amino acid residues in β2 subunit of nAChR and at site for binding ligand mutated into corresponding amino acid residues in β4 subunit (including α-CTx MII). The method for preparing the mutants was carried out according to the document, Shiembob D L, Roberts R L, Luetje C W, McIntosh J M. Determinants of alpha-conotoxin BuIA selectivity on the nicotinic acetylcholine receptor beta subunit. *Biochemistry*. 2006 Sep. 19; 45(37)11200-7.

The details of the former 5 α3β2 nAChRs mutants could be seen in documents, Shiembob D L, Roberts R L, Luetje C W, McIntosh J M. Determinants of alpha-conotoxin BuIA selectivity on the nicotinic acetylcholine receptor beta subunit. *Biochemistry*. 2006 Sep. 19; 45(37):11200-7; and Dutertre S, Nicke A, Lewis R J. β2 subunit contribution to 4/7 α-conotoxin binding to the nicotinic acetylcholine receptor. *J Biol Chem* 2005; 280:30460-8.

The latter 2 α3β2 nAChRs mutants, α3β2 Q34A, α3β2 K79A, related to key amino acids of α-CTx LtIA binding to α3β2 receptor (Luo, S., Akondi, K. B., Zhangsun, D., Wu, Y., Zhu, X., Hu, Y., Christensen, S., Dowell, C., Daly, N. L., Craik, D. J., Wang, C. I., Lewis, R. J., Alewood, P. F., and Michael McIntosh, J. (2010) Atypical alpha-conotoxin LtIA from *Conus litteratus* targets a novel microsite of the alpha3beta2 nicotinic receptor. *J. Biol. Chem.* 285, 12355-12366).

Specific experimental methods were the same of Example 3-(1), and the results were shown in Tables 6-7 and FIGS. 5-6.

It can be seen from Table 2 and FIG. 5, α-CTx LvIA/LvD21 had minimum blocking activity to mutant α3β2 [V111I], which $IC_{50}$ was 126 nM, which activity was 8.7 times lower than that to wild type α3β2 nAChR ($IC_{50}$ was 14.5 nM). Its blocking activities to mutants α3β2 [F119Q], α3β2 [T59K], α3β2 [T59L] were very strong, which $IC_{50}$ values were separately 0.58, 0.96 and 2.03 nM, and which activities were separately 25 times, 15 times and 7 times higher than that to wild type α3β2 nAChR. The α-CTx LvIA/LvD21 showed $IC_{50}$ of 8.64, 10.8 and 15.2 nM separately to mutants α3β2[Q34A], [K79A] and [T59I], which blocking activities were 0.6-1.05 times the blocking activity of wild type α3β2 nAChR, which showed no significant difference from the blocking activity of wild type α3β2 nAChR. The α-CTx LvIA/LvD21 showed blocking activity to mutant α3β2[F119Q] 217 times of that to α3β2[V111I]. This means that the valine at the $111^{th}$ site, the phenylalanine at the $119^{th}$ site, and the threonine at the $59^{th}$ site of β2 subunit played important roles in binding LvIA to α3β2, in which the changes of activity comprised 2 trends, i.e., increase and decrease, which was different from MII, LtIA and other sites as previously disclosed that bound α-CTxs to α3β2 nAChRs.

TABLE 6

$IC_{50}$ and hill slopes of dose-response curves of α-LvIA/LvD21 to wild type and mutants of α3β2 nAChRs

| Type of receptor | Half-blocking dose[a] | Ratio[b] | Ratio[c] | Hill slope of dose-response curves[a] |
|---|---|---|---|---|
| α3β2 | 14.5(11.1-18.8) | 1 | 25 | 1.17(0.79-1.54) |
| α3β2[F119Q] | 0.58(0.44-0.76) | 0.04 | 1 | 1.12(0.79-1.44) |
| α3β2[T59K] | 0.96(0.56-1.65) | 0.07 | 1.7 | 0.80(0.47-1.13) |
| α3β2[T59L] | 2.03(1.52-2.69) | 0.14 | 3.5 | 1.07(0.77-1.37) |
| α3β2[Q34A] | 8.64(4.80-15.5) | 0.60 | 15 | 0.90(0.22-1.58) |
| α3β2[K79A] | 10.8(6.44-18.0) | 0.74 | 19 | 0.86(0.43-1.30) |
| α3β2[T59I] | 15.2(9.71-23.9) | 1.05 | 26 | 1.15(0.43-1.86) |
| α3β2[V111I] | 126(97.2-163) | 8.70 | 217 | 1.31(0.66-1.96) |

In the above table,

[a] refers to confidence interval with confidence degree of 95%;

[b] refers to a ratio of half-blocking dose ($IC_{50}$) between mutant type and wild type of α3β2 nAChRs;

[c] refers to a ratio of half-blocking dose ($IC_{50}$) between other mutant types of α3β2 nAChRs, wild type and mutant type of α3β2[F119Q].

The α-CTx LvIA/LvD21 not only had great effects on blocking activity ($IC_{50}$) of some mutants of α3β2 nAChRs, but also had significant effects on their elution rates (FIG. 6 and Table 7). The research results showed that 10 nM α-LvIA/LvD21 blocked about 50% of current of wild type of α3β2 nAChRs, elution was carried out rapidly, and the current completely recovered within 2 min (FIG. 6A); while 10 nM α-LvIA/LvD21 blocked all current of mutant α3β2 [F119Q], elution was carried out slowly, and the current recovered after elution for 12 min (FIG. 6B); the more significant difference lied in that 10 nM α-LvIA/LvD21 blocked all current of mutant α3β2[T59K], elution was carried out very slowly, the current recovered to 27% of the control current after elution for 20 min (FIG. 6C); however, 10 nM α-LvIA/LvD21 totally did not block the current of mutant α3β2[V111I] (FIG. 6D). The effects of α-LvIA/LvD21 on elution rates of various mutant receptors were shown in Table 7. There were less effects on elution rates in 4 mutants, α3β2[K79A], α3β2[V111I], α3β2[Q34A], and α3β2[T59I], after being blocked with α-LvIA/LvD21, that was, in a very wide range of concentration like 10-10000 nM, their elution were always carried out rapidly, and their currents all recovered to the control level, i.e., 100%, within 1-3 min. As for mutant α3β2[T59L], its elution was carried out relatively slowly, and its current recovered to the control level after 5-8 min. As for mutant α3β2[F119Q], its elution was carried out further slowly, and its current recovered to the control level after 10-12 min. As for mutant α3β2 [T59K], its elution was carried out most slowly, and 10 nM LvIA/LvD21 completely blocked its current, which recovered to 28±3.5% of the control current after elution for 20 min, and after being blocked with 100 nM LvIA/LvD21, its current recovered to 13±2% of the control current after elution for 20 min. It can be seen that the mutant α3β2 [T59K] showed the greatest effects on binding manner of LvIA/LvD21. Hence, the structure and function of α-CTx LvIA/LvD21 provide an important basis for studying mechanism of interaction between α-CTxs and nAChRs, and provide an excellent tool and model therefor.

TABLE 7

Effects of α-CTx LvIA/LvD21 on elution rates of wild type and mutant types of α3β2 nAChRs

| Receptor subtype | Concentration[a] (nM) | Elution time[b] (min) | % of recovered current (%)[c] | Receptor subtype | Concentration[a] (nM) | Elution time[b] (min) | % of recovered current (%)[c] |
|---|---|---|---|---|---|---|---|
| α3β2 | 10-10000 | 2 | 100 | α3β2[T59I] | 10-10000 | 2 | 100 |
| α3β2[K79A] | 10-10000 | 1 | 100 | α3β2[T59L] | 10-10000 | 5-8 | 100 |
| α3β2[V111I] | 100-10000 | 1 | 100 | α3β2[F119Q] | 10-10000 | 10-12 | 100 |
| α3β2[Q34A] | 10-10000 | 2-3 | 100 | α3β2[T59K] | 10 | 20 | 28 ± 3.5[d] |
|  |  |  |  |  | 100 | 20 | 13 ± 2[d] |

In the above table,
[a]denotes concentration of toxin peptide α-CTx LvIA/LvD21;
[b]denotes elution time after blocking, with unit of minute (min);
[c]denotes percentage (%) of recovered current within elution time after blocking;
[d]denotes mean and error (Mean ± standard error) within 95% confidence interval.

Example 5

Experiment of Analgesic Activity of α-LvIA/LvD21

1. Using Rat CCI Model to Test Analgesic Activity of LvIA/LvD21
   (1) Test Animals and Test Materials
   SD (Sprague Dawley) rats were used to prepare chronic constriction injury model of ischiadic nerve (Chronic Constriction Injury model, CCI model), and analgesic activity of the tested conotoxin was measured with pressure pain tester (Rat 800G, which model was US IITC 2391). SD (Sprague Dawley) rats were purchased from the Medical Experimental Animal Center of Guangdong Province. The method of Bennett et al. (Bennett G J, Xie Y K. A peripheral mononeuropathy in rat that produces disorders of pain sensation like those seen in man [J]. *Pain,* 1988, 33(1): 87) was used to prepare the CCI model.

(2) Experimental Method

After being narcotized with intraperitoneal injection of pentobarbital sodium 80 mg/kg, right-lower extremity was incised under aseptic condition to expose stem of ischiadic nerve, which was loosely bound using four 4-0 chromium sutures with interval of 1 mm, the sutures had tightness not affecting blood supply of epineurium, then stitch was carried layer-by-layer. Left-lower extremity was incised to expose stem of ischiadic nerve which however was not ligated and thus used as sham-operation side. Penicillin powder was locally coated on wounds at both sides. Intraperitoneal injection of penicillin was carried out once per day, 80,000 units per time, for consecutive 3 days. 5 rats were raised in 1 cage before cathetering, while 1 rat was raised in 1 cage after cathetering. Qualified rats after primary election were randomly divided into 5 groups, i.e., physiological saline negative control group, morphine positive control group, and toxin peptide α-LvIA/LvD21 test groups, in which the toxin peptide α-LvIA/LvD21 test group was repeated for 2 times (i.e., the toxin peptide α-LvIA/LvD21 test groups were carried out for 3 times). Mechanical pain stimulation values of affected feet and sham-operation feet of rats were measured before operation, after 3 days, 1 week and 2 weeks of operation. The qualified Chronic Constriction Injury models (CCI models) were used as whole animal models for testing therapeutic effects of LvIA/LvD21 on neuralgia.

The analgesic effects of LvIA/LvD21 in CCI models were tested by intraperitoneal injection. Physiological saline (Saline) was used as blank control, i.e., negative control; morphine was positive control, with a dose of 1 mg/kg of rat body weight. The test group used toxin peptide α-LvIA/LvD21, with a dose of 1 nmol/kg (~1.7 μg/kg) rat body weight, in which each group had 8 rats (n=8). The analgesic activity was represented with Mechanical Threshold, which was a ratio percentage (% of basal) of observed pain threshold to basal pain threshold (100), and the greater the ratio, the better the analgesic effects.

(3) Test Results

The results are shown in FIG. 7-8.

FIG. 7 shows the analgesic effects in CCI models after intraperitoneal injection (IP) of α-LvIA/LvD21 for 1-24 h. LvIA/LvD21 showed potent analgesic effects on neuralgia after administration for 1 h, while the positive control of morphine showed no analgesic effect after administration for 1 h; LvIA/LvD21 showed the maximum of analgesic effects on neuralgia after administration for 3 h, an average analgesic value of 160%, and up to 200% in some cases, while the positive control of morphine showed an average analgesic value of 120% after administration for 3 h; and after 24 h, LvIA/LvD21 still exhibited an analgesic value far higher than morphine (FIG. 7).

After administration for consecutive 7 days, analgesic value was tested after withdrawal for 1 week (the $7^{th}$ to $14^{th}$ days), and the results are shown in FIG. 8. In the $7^{th}$ to $14^{th}$ days, LvIA/LvD21 showed mechanical threshold values significantly higher than that of morphine group, and the best analgesic effect was observed on the $12^{th}$ day, an average analgesic value was up to 200%, the morphine group showed no significant difference of analgesic value in comparison with the physiological saline control group. This indicates that the analgesic effect of morphine disappeared after withdrawal, while LvIA/LvD21 still maintained analgesic effect after withdrawal (FIG. 8), and this suggests LvIA/LvD21 has not only analgesic effects, but also curative effects on neuralgia.

The above results show that LvIA/LvD21 has more potent analgesic effects than morphine, and when expressed under same weight and dose, the analgesic effect of LvIA/LvD21 in CCI model is 823-1176 times higher than that of morphine. Intraperitoneal injection of LvIA/LvD21 shows potent analgesic effects and good persistence in rat CCI model, and conotoxins per se do not induce addiction.

2. Analgesic Activity of LvIA/LvD21 Using Mice Hot-Plate Test (1) Test Animals

Mice with response latency of less than 5 s or greater than 30 s were removed, and 50 female Kunming mice with body weight of 18±2 g were used. Before administration, the mice were placed on a metal plate of 55±0.5° C. hot-plate pain threshold detector (which type was US IITC 39), and latent period (S) was calculated with time for response of licking hind leg or jumping in mice.

(2) Test Method

The mice were divided according to random allocation numeration table into 3 groups, i.e., negative control physiological saline (Saline), positive control morphine (Morphine), and α-conotoxin LvIA/LvD21, 10 mice per group. For each of the groups, intracerebroventricular injection was carried out with an injection volume of 10 μL per mouse. The administration dosage for positive control morphine was 100 μg/kg mouse body weight; the administration dosage for α-LvIA/LvD21 was 0.1 nmol/kg (~0.17 μg/kg) mouse body weight. As expressed in same weight and dosage, the dosage of positive control morphine was 588 times higher than that of LvIA/LvD21. Before administration, the mice were placed on a metal plate of 55±0.5° C. hot-plate pain threshold detector (which type was US IITC 39), and latent period with unit of second (s) for response of licking hind leg or jumping in mice was used as pain threshold. Each mouse was measured twice and the average value thereof was used as basal pain threshold, and the time interval between the 2 measurements was 5 min. In order to avoid burning feet, closing time was 60 s, and the pain threshold for those over 60 s was recorded as 60 s. After administration, pain threshold values were separately measured at 15, 30, 45, 60, 90, 120 min, and the results were represented as $\bar{x}\pm s$.

(3) Test Results

The results are shown in FIG. 9.

The α-CTx LvIA/LvD21 showed very potent analgesic activity in hot-plate test models (FIG. 9). Before administration, the mice of 3 groups all had basal pain threshold between about 14 s and about 17 s. After administration, at all time-points, the pain threshold of positive control physiological saline (Saline) was maintained at about 14-17 s, while the pain threshold for LvIA/LvD21 increased rapidly to 30 s at 15 min after administration, and the pain threshold for morphine also increased rapidly to 32 s (FIG. 9), in the meantime, LvIA/LvD21 showed potent analgesic activity, which indicated LvIA/LvD21 LvIA showed very fast onset of analgesic action. Within 30-90 min after administration, the pain threshold of LvIA/LvD21 slightly decreased and then continuously increased, while the pain threshold of morphine continuously decreased, and the pain threshold of LvIA/LvD21 increased 1.3-1.5 times in comparison with the pain threshold of morphine. At 120 min after administration, the pain threshold of LvIA/LvD21 slightly decreased, but was still 1.3 times higher than the pain threshold of morphine at the time. If expressed in same weight and dosage, the analgesic effect of LvIA/LvD21 in hot-plate models was 764-882 times higher than that of morphine.

Although the embodiments of the present invention have been described in details, those skilled in the art would understand that these details can be modified or replaced according the disclosures, and all these changes fall into the protection scope of the present invention. The whole protection scope of the present invention is defined by the appended claims and any equivalents thereof.

What is claimed is:

1. A polypeptide, which comprises an amino acid sequence selected from the group consisting of SEQ ID NO: 11 and SEQ ID NO: 12, wherein the carboxyl terminal of the polypeptide is amidated.

2. The polypeptide according to claim 1, wherein at the N-terminal of the polypeptide, the 1st cysteine and the 3rd cysteine of said amino acid sequence form a disulfide bond, and the 2nd cysteine and the 4th cysteine of said amino acid sequence form a disulfide bond; or at the N-terminal of the polypeptide, the 1st cysteine and the 4th cysteine of said amino acid sequence form a disulfide bond, and the 2nd cysteine and the 3rd cysteine of said amino acid sequence form a disulfide bond; or at the N-terminal of the polypeptide, the 1st cysteine and the 2nd cysteine of said amino acid sequence form a disulfide bond, and the 3rd cysteine and the 4th cysteine of said amino acid sequence form a disulfide bond.

3. The polypeptide according to claim 1, wherein the polypeptide consists of an amino acid sequence selected from the group consisting of SEQ ID NO: 11 and SEQ ID NO: 12.

4. The polypeptide according to claim 3, wherein at the N-terminal of the polypeptide, the 1st cysteine and the 3rd cysteine of said amino acid sequence form a disulfide bond, and the 2nd cysteine and the 4th cysteine of said amino acid sequence form a disulfide bond; or at the N-terminal of the polypeptide, the 1st cysteine and the 4th cysteine of said amino acid sequence form a disulfide bond, and the 2nd cysteine and the 3rd cysteine of said amino acid sequence form a disulfide bond; or at the N-terminal of the polypeptide, the 1st cysteine and the 2nd cysteine of said amino acid sequence form a disulfide bond, and the 3rd cysteine and the 4th cysteine of said amino acid sequence form a disulfide bond.

5. A pharmaceutical composition, which comprises the polypeptide according to claim 1 and a pharmaceutically acceptable carrier or excipient.

6. A method for blocking an acetylcholine receptor or regulating acetylcholine level in cells, comprising the step of applying an effective amount of the polypeptide according to claim 1 to the cells, wherein said acetylcholine receptor is α6/α3β2β3 acetylcholine receptor.

7. The method of claim 6, wherein the cells are cells in vivo.

8. A method for preparing the polypeptide according to claim 1, comprising the following steps:
   1) synthesizing a linear polypeptide by ABI Prism 433a polypeptide synthesizer or by a manual method, in which side-chain protecting groups of Fmoc amino acids are: Pmc (Arg), Trt or Acm (Cys), But (Thr, Ser, Tyr), OBut (Asp), and Boc (Lys);

2) cutting the linear polypeptide of step 1) from resin;
3) using glacial diethyl ether to precipitate and wash the linear polypeptide obtained in step 2), and recovering a crude product of linear polypeptide;
4) using a preparative reversed phase HPLC C18 column to purify the crude product of linear polypeptide obtained in step 3); and
5) subjecting the product obtained in step 4) to two-step or one-step oxidative folding.

\* \* \* \* \*

SEQUENCE LISTING

```
<160> NUMBER OF SEQ ID NOS: 68

<210> SEQ ID NO 1
<211> LENGTH: 132
<212> TYPE: DNA
<213> ORGANISM: C. textile Linnaeus

<400> SEQUENCE: 1
gtggttctgg gtccagcatt tcgtggcagg gacgccgcag ccaaagcgtc tggcctggtt      60
ggtctgactg acaggagagg atgctgttct catcctgcct gtaacgtaga tcatccagaa     120
atttgtggct ga                                                         132

<210> SEQ ID NO 2
<211> LENGTH: 114
<212> TYPE: DNA
<213> ORGANISM: artificial sequence
<220> FEATURE:
<223> OTHER INFORMATION: Synthetic oligonucleotide

<400> SEQUENCE: 2
tttcgtggca gggacgccgc agccaaagcg tctggcctgg ttggtctgac tgacaggaga      60
ggatgctgtt ctcatcctgc ctgtaacgta gatcatccag aaatttgtgg ctga           114

<210> SEQ ID NO 3
<211> LENGTH: 37
<212> TYPE: PRT
<213> ORGANISM: artificial sequence
<220> FEATURE:
<223> OTHER INFORMATION: Synthetic peptide

<400> SEQUENCE: 3

Phe Arg Gly Arg Asp Ala Ala Ala Lys Ala Ser Gly Leu Val Gly Leu
```

```
                1               5                   10                  15
Thr Asp Arg Arg Gly Cys Cys Ser His Pro Ala Cys Asn Val Asp His
                    20                  25                  30

Pro Glu Ile Cys Gly
        35

<210> SEQ ID NO 4
<211> LENGTH: 16
<212> TYPE: PRT
<213> ORGANISM: artificial sequence
<220> FEATURE:
<223> OTHER INFORMATION: Synthetic peptide

<400> SEQUENCE: 4

Gly Cys Cys Ser His Pro Ala Cys Asn Val Asp His Pro Glu Ile Cys
1               5                   10                  15

<210> SEQ ID NO 5
<211> LENGTH: 48
<212> TYPE: DNA
<213> ORGANISM: artificial sequence
<220> FEATURE:
<223> OTHER INFORMATION: Synthetic oligonucleotide

<400> SEQUENCE: 5
ggatgctgtt ctcatcctgc ctgtaacgta gatcatccag aaatttgt                    48

<210> SEQ ID NO 6
<211> LENGTH: 17
<212> TYPE: PRT
<213> ORGANISM: artificial sequence
<220> FEATURE:
<223> OTHER INFORMATION: Synthetic peptide

<400> SEQUENCE: 6

Gly Cys Cys Ser His Pro Ala Cys Asn Val Asp His Pro Glu Ile Cys
1               5                   10                  15

Gly

<210> SEQ ID NO 7
<211> LENGTH: 54
<212> TYPE: DNA
<213> ORGANISM: artificial sequence
<220> FEATURE:
<223> OTHER INFORMATION: Synthetic oligonucleotide

<400> SEQUENCE: 7
ggatgctgtt ctcatcctgc ctgtaacgta gatcatccag aaatttgtgg ctga            54

<210> SEQ ID NO 8
<211> LENGTH: 51
<212> TYPE: DNA
<213> ORGANISM: artificial sequence
<220> FEATURE:
<223> OTHER INFORMATION: Synthetic oligonucleotide

<400> SEQUENCE: 8
ggatgctgtt ctcatcctgc ctgtaacgta gatcatccag aaatttgtgg c                51

<210> SEQ ID NO 9
<211> LENGTH: 18
<212> TYPE: DNA
<213> ORGANISM: artificial sequence
<220> FEATURE:
<223> OTHER INFORMATION: Synthetic oligonucleotide
```

```
<400> SEQUENCE: 9
gtggttctgg gtccagca                                              18

<210> SEQ ID NO 10
<211> LENGTH: 18
<212> TYPE: DNA
<213> ORGANISM: artificial sequence
<220> FEATURE:
<223> OTHER INFORMATION: Synthetic oligonucleotide

<400> SEQUENCE: 10
gtcgtggttc agagggtc                                              18

<210> SEQ ID NO 11
<211> LENGTH: 16
<212> TYPE: PRT
<213> ORGANISM: artificial sequence
<220> FEATURE:
<223> OTHER INFORMATION: Synthetic peptide

<400> SEQUENCE: 11

Gly Cys Cys Ser Asp Pro Pro Cys Arg Asn Lys His Pro Asp Leu Cys
1               5                   10                  15

<210> SEQ ID NO 12
<211> LENGTH: 17
<212> TYPE: PRT
<213> ORGANISM: artificial sequence
<220> FEATURE:
<223> OTHER INFORMATION: Synthetic peptide

<400> SEQUENCE: 12

Gly Cys Cys Ser Asp Pro Pro Cys Arg Asn Lys His Pro Asp Leu Cys
1               5                   10                  15

Gly

<210> SEQ ID NO 13
<211> LENGTH: 18
<212> TYPE: PRT
<213> ORGANISM: artificial sequence
<220> FEATURE:
<223> OTHER INFORMATION: Synthetic peptide

<400> SEQUENCE: 13

Gly Cys Cys Ser Asp Pro Pro Cys Arg Asn Lys His Pro Asp Leu Cys
1               5                   10                  15

Gly Gly

<210> SEQ ID NO 14
<211> LENGTH: 20
<212> TYPE: PRT
<213> ORGANISM: artificial sequence
<220> FEATURE:
<223> OTHER INFORMATION: Synthetic peptide

<400> SEQUENCE: 14

Gly Cys Cys Ser Asp Pro Pro Cys Arg Asn Lys His Pro Asp Leu Cys
1               5                   10                  15

Gly Gly Arg Arg
            20

<210> SEQ ID NO 15
<211> LENGTH: 41
```

```
<212> TYPE: PRT
<213> ORGANISM: artificial sequence
<220> FEATURE:
<223> OTHER INFORMATION: Synthetic peptide

<400> SEQUENCE: 15

Phe Asp Gly Arg Asn Thr Ser Ala Asn Asn Lys Ala Thr Asp Leu Met
1               5                   10                  15

Ala Leu Pro Val Arg Gly Cys Cys Ser Asp Pro Pro Cys Arg Asn Lys
            20                  25                  30

His Pro Asp Leu Cys Gly Gly Arg Arg
        35                  40

<210> SEQ ID NO 16
<211> LENGTH: 48
<212> TYPE: DNA
<213> ORGANISM: artificial sequence
<220> FEATURE:
<223> OTHER INFORMATION: Synthetic oligonucleotide

<400> SEQUENCE: 16
ggatgctgtt ccgatcctcc ctgtagaaac aagcacccag atctttgt              48

<210> SEQ ID NO 17
<211> LENGTH: 51
<212> TYPE: DNA
<213> ORGANISM: artificial sequence
<220> FEATURE:
<223> OTHER INFORMATION: Synthetic oligonucleotide

<400> SEQUENCE: 17
ggatgctgtt ccgatcctcc ctgtagaaac aagcacccag atctttgtgg c          51

<210> SEQ ID NO 18
<211> LENGTH: 54
<212> TYPE: DNA
<213> ORGANISM: artificial sequence
<220> FEATURE:
<223> OTHER INFORMATION: Synthetic oligonucleotide

<400> SEQUENCE: 18
ggatgctgtt ccgatcctcc ctgtagaaac aagcacccag atctttgtgg cgga       54

<210> SEQ ID NO 19
<211> LENGTH: 63
<212> TYPE: DNA
<213> ORGANISM: artificial sequence
<220> FEATURE:
<223> OTHER INFORMATION: Synthetic oligonucleotide

<400> SEQUENCE: 19
ggatgctgtt ccgatcctcc ctgtagaaac aagcacccag atctttgtgg cggaagacgc 60
tga                                                              63

<210> SEQ ID NO 20
<211> LENGTH: 126
<212> TYPE: DNA
<213> ORGANISM: artificial sequence
<220> FEATURE:
<223> OTHER INFORMATION: Synthetic oligonucleotide

<400> SEQUENCE: 20
tttgatggca ggaataccte agccaacaac aaagcgactg acctgatggc tctgcctgtc 60
agggatgctg ttccgatcct ccctgtagaa acaagcacc cagatctttg tggcggaaga 120
``` cgctga 126

<210> SEQ ID NO 21
<211> LENGTH: 170
<212> TYPE: DNA
<213> ORGANISM: C. textile Linnaeus

<400> SEQUENCE: 21
gtggttctgg gtccagcatt tgatggcagg aatacctcag ccaacaacaa agcgactgac    60
ctgatggctc tgcctgtcag gggatgctgt tccgatcctc cctgtagaaa caagcaccca   120
gatctttgtg gcggaagacg ctgatgctcc aggaccctct gaaccacgac              170

<210> SEQ ID NO 22
<211> LENGTH: 168
<212> TYPE: DNA
<213> ORGANISM: C. textile Linnaeus

<400> SEQUENCE: 22
gtggttctgg gtccagcatt tgatggcagg aatgctgcag gcaacgacaa aatgtccgcc    60
ctgatggctc tgaccaccag gggatgctgt tcccatcctg tctgtagcgc gatgagtcca   120
atctgtggct gaagacgctg atgctccagg accctctgaa ccacgaca               168

<210> SEQ ID NO 23
<211> LENGTH: 168
<212> TYPE: DNA
<213> ORGANISM: C. textile Linnaeus

<400> SEQUENCE: 23
gtggttctgg gtccagcatt tgatggcagg aatgctgcag gcaacgacaa aatgtccgcc    60
ctgatggctc tgaccatcag gggatgctgt tcccatcctg tctgtagcgc gatgagtcca   120
atctgtggct gaagacgctg atgctccagg accctctgaa ccacgaca               168

<210> SEQ ID NO 24
<211> LENGTH: 114
<212> TYPE: DNA
<213> ORGANISM: artificial sequence
<220> FEATURE:
<223> OTHER INFORMATION: Synthetic oligonucleotide

<400> SEQUENCE: 24
tttgatggca ggaatgctgc aggcaacgac aaaatgtccg ccctgatggc tctgaccacc    60
aggggatgct gttcccatcc tgtctgtagc gcgatgagtc caatctgtgg ctga         114

<210> SEQ ID NO 25
<211> LENGTH: 114
<212> TYPE: DNA
<213> ORGANISM: artificial sequence
<220> FEATURE:
<223> OTHER INFORMATION: Synthetic oligonucleotide

<400> SEQUENCE: 25
tttgatggca ggaatgctgc aggcaacgac aaaatgtccg ccctgatggc tctgaccatc    60
aggggatgct gttcccatcc tgtctgtagc gcgatgagtc caatctgtgg ctga         114

<210> SEQ ID NO 26
<211> LENGTH: 37
<212> TYPE: PRT
<213> ORGANISM: artificial sequence
<220> FEATURE:

<223> OTHER INFORMATION: Synthetic peptide

<400> SEQUENCE: 26

Phe Asp Gly Arg Asn Ala Ala Gly Asn Asp Lys Met Ser Ala Leu Met
1               5                   10                  15

Ala Leu Thr Thr Arg Gly Cys Cys Ser His Pro Val Cys Ser Ala Met
            20                  25                  30

Ser Pro Ile Cys Gly
        35

<210> SEQ ID NO 27
<211> LENGTH: 37
<212> TYPE: PRT
<213> ORGANISM: artificial sequence
<220> FEATURE:
<223> OTHER INFORMATION: Synthetic peptide

<400> SEQUENCE: 27

Phe Asp Gly Arg Asn Ala Ala Gly Asn Asp Lys Met Ser Ala Leu Met
1               5                   10                  15

Ala Leu Thr Ile Arg Gly Cys Cys Ser His Pro Val Cys Ser Ala Met
            20                  25                  30

Ser Pro Ile Cys Gly
        35

<210> SEQ ID NO 28
<211> LENGTH: 15
<212> TYPE: PRT
<213> ORGANISM: artificial sequence
<220> FEATURE:
<223> OTHER INFORMATION: Synthetic peptide

<400> SEQUENCE: 28

Gly Cys Cys Ser His Pro Val Cys Ser Ala Met Ser Pro Ile Cys
1               5                   10                  15

<210> SEQ ID NO 29
<211> LENGTH: 45
<212> TYPE: DNA
<213> ORGANISM: artificial sequence
<220> FEATURE:
<223> OTHER INFORMATION: Synthetic oligonucleotide

<400> SEQUENCE: 29
ggatgctgtt cccatcctgt ctgtagcgcg atgagtccaa tctgt            45

<210> SEQ ID NO 30
<211> LENGTH: 16
<212> TYPE: PRT
<213> ORGANISM: artificial sequence
<220> FEATURE:
<223> OTHER INFORMATION: Synthetic peptide

<400> SEQUENCE: 30

Gly Cys Cys Ser His Pro Val Cys Ser Ala Met Ser Pro Ile Cys Gly
1               5                   10                  15

<210> SEQ ID NO 31
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 31
ggatgctgtt cccatcctgt ctgtagcgcg atgagtccaa tctgtggctg a                51

<210> SEQ ID NO 32
<211> LENGTH: 21
<212> TYPE: PRT
<213> ORGANISM: Conus C. textile

<400> SEQUENCE: 32

Phe Asp Gly Arg Asn Thr Ser Ala Asn Asn Lys Ala Thr Asp Leu Met
1               5                   10                  15

Ala Leu Pro Val Arg
            20

<210> SEQ ID NO 33
<211> LENGTH: 20
<212> TYPE: PRT
<213> ORGANISM: Conus C. textile

<400> SEQUENCE: 33

Gly Cys Cys Ser Asp Pro Pro Cys Arg Asn Lys His Pro Asp Leu Cys
1               5                   10                  15

Gly Gly Arg Arg
            20

<210> SEQ ID NO 34
<211> LENGTH: 39
<212> TYPE: PRT
<213> ORGANISM: Conus C. textile

<400> SEQUENCE: 34

Met Phe Thr Val Phe Leu Leu Val Val Leu Ala Thr Ala Val Val Ser
1               5                   10                  15

Phe Thr Ser Asp Arg Ala Ser Asp Asp Gly Lys Ala Ala Ala Ser Asp
                20                  25                  30

Leu Ile Thr Leu Thr Ile Lys
        35

<210> SEQ ID NO 35
<211> LENGTH: 17
<212> TYPE: PRT
<213> ORGANISM: Conus C. textile

<400> SEQUENCE: 35

Gly Cys Cys Ser Arg Pro Pro Cys Ile Ala Asn Asn Pro Asp Leu Cys
1               5                   10                  15

Gly

<210> SEQ ID NO 36
<211> LENGTH: 48
<212> TYPE: PRT
<213> ORGANISM: Conus C. magus

<400> SEQUENCE: 36

Met Gly Met Arg Met Met Phe Thr Val Phe Leu Leu Val Val Leu Ala
1               5                   10                  15

Thr Thr Val Val Ser Phe Pro Ser Asp Arg Ala Ser Asp Gly Arg Asn
                20                  25                  30

Ala Ala Ala Asn Asp Lys Ala Ser Asp Val Ile Thr Leu Ala Leu Lys
        35                  40                  45

```
<210> SEQ ID NO 37
<211> LENGTH: 20
<212> TYPE: PRT
<213> ORGANISM: Conus C. magus

<400> SEQUENCE: 37

Gly Cys Cys Ser Asn Pro Val Cys His Leu Glu His Ser Asn Leu Cys
1               5                   10                  15

Gly Arg Arg Arg
            20

<210> SEQ ID NO 38
<211> LENGTH: 48
<212> TYPE: PRT
<213> ORGANISM: Conus C. litteratus

<400> SEQUENCE: 38

Met Gly Met Arg Met Met Phe Ile Met Phe Met Leu Val Val Leu Ala
1               5                   10                  15

Thr Thr Val Val Thr Phe Thr Ser Asp Arg Ala Leu Asp Ala Met Asn
            20                  25                  30

Ala Ala Ala Ser Asn Lys Ala Ser Arg Leu Ile Ala Leu Ala Val Arg
        35                  40                  45

<210> SEQ ID NO 39
<211> LENGTH: 20
<212> TYPE: PRT
<213> ORGANISM: Conus C. litteratus

<400> SEQUENCE: 39

Gly Cys Cys Ala Arg Ala Ala Cys Ala Gly Ile His Gln Glu Leu Cys
1               5                   10                  15

Gly Gly Gly Arg
            20

<210> SEQ ID NO 40
<211> LENGTH: 43
<212> TYPE: PRT
<213> ORGANISM: Conus C. purpurascens

<400> SEQUENCE: 40

Met Phe Thr Val Phe Leu Leu Val Val Leu Ala Thr Thr Val Gly Ser
1               5                   10                  15

Phe Thr Leu Asp Arg Ala Ser Asp Gly Arg Asp Ala Ala Ala Asn Asp
            20                  25                  30

Lys Ala Thr Asp Leu Ile Ala Leu Thr Ala Arg
        35                  40

<210> SEQ ID NO 41
<211> LENGTH: 19
<212> TYPE: PRT
<213> ORGANISM: Conus C. purpurascens

<400> SEQUENCE: 41

Arg Asp Pro Cys Cys Ser Asn Pro Val Cys Thr Val His Asn Pro Gln
1               5                   10                  15

Ile Cys Gly

<210> SEQ ID NO 42
<211> LENGTH: 20
<212> TYPE: PRT
<213> ORGANISM: Conus C. geographus
```

```
<400> SEQUENCE: 42

Ser Asp Gly Arg Asn Asp Ala Ala Lys Ala Phe Asp Leu Ile Ser Ser
1               5                   10                  15

Thr Val Lys Lys
            20

<210> SEQ ID NO 43
<211> LENGTH: 20
<212> TYPE: PRT
<213> ORGANISM: Conus C. geographus

<400> SEQUENCE: 43

Gly Cys Cys Ser His Pro Ala Cys Ala Gly Asn Asn Gln His Ile Cys
1               5                   10                  15

Gly Arg Arg Arg
            20

<210> SEQ ID NO 44
<211> LENGTH: 44
<212> TYPE: PRT
<213> ORGANISM: Conus C. pennaceus

<400> SEQUENCE: 44

Met Gly Met Arg Met Met Phe Thr Val Phe Leu Leu Val Val Leu Ala
1               5                   10                  15

Thr Thr Val Val Ser Phe Thr Ser Asp Arg Ala Ser Asp Asp Gly Asn
            20                  25                  30

Ala Ala Ala Ser Asp Leu Ile Ala Leu Thr Ile Lys
        35                  40

<210> SEQ ID NO 45
<211> LENGTH: 17
<212> TYPE: PRT
<213> ORGANISM: Conus C. pennaceus

<400> SEQUENCE: 45

Gly Cys Cys Ser Leu Pro Pro Cys Ala Leu Ser Asn Pro Asp Tyr Cys
1               5                   10                  15

Gly

<210> SEQ ID NO 46
<211> LENGTH: 48
<212> TYPE: PRT
<213> ORGANISM: Conus C. spurius

<400> SEQUENCE: 46

Met Gly Met Arg Met Met Phe Thr Val Phe Leu Leu Val Val Leu Ala
1               5                   10                  15

Thr Thr Val Val Ser Phe Thr Ser Asp Ser Ala Phe Asp Ser Arg Asn
            20                  25                  30

Val Ala Ala Asn Asp Lys Val Ser Asp Met Ile Ala Leu Thr Ala Arg
        35                  40                  45

<210> SEQ ID NO 47
<211> LENGTH: 21
<212> TYPE: PRT
<213> ORGANISM: Conus C. spurius

<400> SEQUENCE: 47

Arg Thr Cys Cys Ser Arg Pro Thr Cys Arg Met Glu Tyr Pro Glu Leu
```

```
1               5                   10                  15
Cys Gly Gly Arg Arg
            20
```

<210> SEQ ID NO 48
<211> LENGTH: 49
<212> TYPE: PRT
<213> ORGANISM: Conus C. victoriae

<400> SEQUENCE: 48

```
Met Gly Met Arg Met Met Phe Thr Val Phe Leu Leu Val Val Leu Ala
1               5                   10                  15

Thr Thr Val Val Ser Ser Thr Ser Gly Arg Arg Glu Phe Arg Gly Arg
            20                  25                  30

Asn Ala Ala Ala Lys Ala Ser Asp Leu Val Ser Leu Thr Asp Lys Lys
        35                  40                  45

Arg
```

<210> SEQ ID NO 49
<211> LENGTH: 17
<212> TYPE: PRT
<213> ORGANISM: Conus C. victoriae

<400> SEQUENCE: 49

```
Gly Cys Cys Ser Asp Pro Arg Cys Asn Tyr Asp His Pro Glu Ile Cys
1               5                   10                  15

Gly
```

<210> SEQ ID NO 50
<211> LENGTH: 39
<212> TYPE: PRT
<213> ORGANISM: Conus C. aulicus

<400> SEQUENCE: 50

```
Met Phe Thr Val Phe Leu Leu Val Val Leu Ala Thr Thr Val Val Ser
1               5                   10                  15

Phe Thr Ser Asp Arg Ala Ser Asp Gly Arg Lys Asp Ala Ala Ser Gly
            20                  25                  30

Leu Ile Ala Leu Thr Met Lys
        35
```

<210> SEQ ID NO 51
<211> LENGTH: 19
<212> TYPE: PRT
<213> ORGANISM: Conus C. aulicus

<400> SEQUENCE: 51

```
Gly Cys Cys Ser Tyr Pro Pro Cys Phe Ala Thr Asn Pro Asp Cys Gly
1               5                   10                  15

Arg Arg Arg
```

<210> SEQ ID NO 52
<211> LENGTH: 43
<212> TYPE: PRT
<213> ORGANISM: Conus C. bullatus

<400> SEQUENCE: 52

```
Met Phe Thr Val Phe Leu Leu Val Val Leu Thr Thr Thr Val Val Ser
1               5                   10                  15

Phe Pro Ser Asp Arg Ala Ser Asp Gly Arg Asn Ala Ala Ala Asn Asp
```

```
                    20                  25                  30

Lys Ala Ser Asp Val Val Thr Leu Val Leu Lys
            35                  40

<210> SEQ ID NO 53
<211> LENGTH: 17
<212> TYPE: PRT
<213> ORGANISM: Conus C. bullatus

<400> SEQUENCE: 53

Gly Cys Cys Ser Thr Pro Pro Cys Ala Val Leu Tyr Cys Gly Arg Arg
1               5                   10                  15

Arg

<210> SEQ ID NO 54
<211> LENGTH: 19
<212> TYPE: PRT
<213> ORGANISM: Conus C. regius

<400> SEQUENCE: 54

Ser Asn Lys Arg Lys Asn Ala Ala Met Leu Asp Met Ile Ala Gln His
1               5                   10                  15

Ala Ile Arg

<210> SEQ ID NO 55
<211> LENGTH: 13
<212> TYPE: PRT
<213> ORGANISM: Conus C. regius

<400> SEQUENCE: 55

Gly Cys Cys Ser Asp Pro Arg Cys Arg Tyr Arg Cys Arg
1               5                   10

<210> SEQ ID NO 56
<211> LENGTH: 47
<212> TYPE: PRT
<213> ORGANISM: Conus C. achatinus

<400> SEQUENCE: 56

Met Gly Met Arg Met Met Phe Thr Leu Phe Leu Leu Val Val Leu Thr
1               5                   10                  15

Thr Thr Val Val Ser Tyr Pro Ser Asp Ser Ala Ser Asp Gly Arg Asp
            20                  25                  30

Asp Glu Ala Lys Asp Glu Arg Ser Asp Met Tyr Glu Leu Lys Arg
        35                  40                  45

<210> SEQ ID NO 57
<211> LENGTH: 17
<212> TYPE: PRT
<213> ORGANISM: Conus C. achatinus

<400> SEQUENCE: 57

Asn Gly Arg Cys Cys His Pro Ala Cys Gly Lys His Phe Asn Cys Gly
1               5                   10                  15

Arg

<210> SEQ ID NO 58
<211> LENGTH: 15
<212> TYPE: PRT
<213> ORGANISM: Conus C. textile
<220> FEATURE:
<221> NAME/KEY: MISC_FEATURE
```

-continued

```
<222> LOCATION: (15)..(15)
<223> OTHER INFORMATION: Cys at position 15 is amidated at its C
      terminus.

<400> SEQUENCE: 58

Gly Cys Cys Ser His Pro Val Cys Ser Ala Met Ser Pro Ile Cys
1               5                   10                  15

<210> SEQ ID NO 59
<211> LENGTH: 15
<212> TYPE: PRT
<213> ORGANISM: Conus C. aulicus
<220> FEATURE:
<221> NAME/KEY: MISC_FEATURE
<222> LOCATION: (15)..(15)
<223> OTHER INFORMATION: Cys at position 15 is amidated at its C
      terminus.

<400> SEQUENCE: 59

Gly Cys Cys Ser Tyr Pro Pro Cys Phe Ala Thr Asn Pro Asp Cys
1               5                   10                  15

<210> SEQ ID NO 60
<211> LENGTH: 13
<212> TYPE: PRT
<213> ORGANISM: Conus C. bullatus
<220> FEATURE:
<221> NAME/KEY: MISC_FEATURE
<222> LOCATION: (13)..(13)
<223> OTHER INFORMATION: Cys at position 13 is amidated at its C
      terminus.

<400> SEQUENCE: 60

Gly Cys Cys Ser Thr Pro Pro Cys Ala Val Leu Tyr Cys
1               5                   10

<210> SEQ ID NO 61
<211> LENGTH: 12
<212> TYPE: PRT
<213> ORGANISM: Conus C. imperialis
<220> FEATURE:
<221> NAME/KEY: MISC_FEATURE
<222> LOCATION: (12)..(12)
<223> OTHER INFORMATION: Cys at position 12 is amidated at its C
      terminus.

<400> SEQUENCE: 61

Gly Cys Cys Ser Asp Pro Arg Cys Ala Trp Arg Cys
1               5                   10

<210> SEQ ID NO 62
<211> LENGTH: 16
<212> TYPE: PRT
<213> ORGANISM: Conus C. regius
<220> FEATURE:
<221> NAME/KEY: MISC_FEATURE
<222> LOCATION: (16)..(16)
<223> OTHER INFORMATION: Cys at position 16 is amidated at its C
      terminus.

<400> SEQUENCE: 62

Gly Cys Cys Ser His Pro Ala Cys Asn Val Asn Asn Pro His Ile Cys
1               5                   10                  15

<210> SEQ ID NO 63
<211> LENGTH: 16
<212> TYPE: PRT
<213> ORGANISM: Conus C. pergrandis
<220> FEATURE:
```

-continued

```
<221> NAME/KEY: MISC_FEATURE
<222> LOCATION: (16)..(16)
<223> OTHER INFORMATION: Cys at position 16 is amidated at its C
      terminus.

<400> SEQUENCE: 63

Gly Cys Cys Ser His Pro Ala Cys Ser Val Asn His Pro Glu Leu Cys
1               5                   10                  15

<210> SEQ ID NO 64
<211> LENGTH: 18
<212> TYPE: PRT
<213> ORGANISM: Conus C. purpurascens
<220> FEATURE:
<221> NAME/KEY: MISC_FEATURE
<222> LOCATION: (16)..(16)
<223> OTHER INFORMATION: Gln at position 15 is amidated at its C
      terminus.

<400> SEQUENCE: 64

Arg Asp Pro Cys Cys Ser Asn Pro Val Cys Thr Val His Asn Pro Gln
1               5                   10                  15

Ile Cys

<210> SEQ ID NO 65
<211> LENGTH: 16
<212> TYPE: PRT
<213> ORGANISM: Conus C. victoriae
<220> FEATURE:
<221> NAME/KEY: MISC_FEATURE
<222> LOCATION: (16)..(16)
<223> OTHER INFORMATION: Cys at position 16 is amidated at its C
      terminus.

<400> SEQUENCE: 65

Gly Cys Cys Ser Asp Pro Arg Cys Asn Tyr Asp His Pro Glu Ile Cys
1               5                   10                  15

<210> SEQ ID NO 66
<211> LENGTH: 16
<212> TYPE: PRT
<213> ORGANISM: Conus C. geographus
<220> FEATURE:
<221> NAME/KEY: MISC_FEATURE
<222> LOCATION: (16)..(16)
<223> OTHER INFORMATION: Cys at position 16 is amidated at its C
      terminus.

<400> SEQUENCE: 66

Gly Cys Cys Ser His Pro Ala Cys Ala Gly Asn Asn Gln His Ile Cys
1               5                   10                  15

<210> SEQ ID NO 67
<211> LENGTH: 168
<212> TYPE: DNA
<213> ORGANISM: Conus C. textile Linnaeus

<400> SEQUENCE: 67
gtggttctgg gtccagcatt cgtggcagg gacgccgcag ccaaagcgtc tggcctggtt      60
ggtctgactg acaggagagg atgctgttct catcctgcct gtaacgtaga tcatccagaa    120
atttgtggct gaagacgctg atgctccagg accctctgaa ccacgaca                 168

<210> SEQ ID NO 68
<211> LENGTH: 17
<212> TYPE: PRT
<213> ORGANISM: Artificial Sequence
```

```
<220> FEATURE:
<223> OTHER INFORMATION: Synthetic polypeptide of Formula I
<220> FEATURE:
<221> NAME/KEY: MISC_FEATURE
<222> LOCATION: (5)..(5)
<223> OTHER INFORMATION: Xaa represents D or H'
<220> FEATURE:
<221> NAME/KEY: MISC_FEATURE
<222> LOCATION: (7)..(7)
<223> OTHER INFORMATION: Xaa represents P, A or V
<220> FEATURE:
<221> NAME/KEY: MISC_FEATURE
<222> LOCATION: (9)..(9)
<223> OTHER INFORMATION: Xaa represents R, N or S
<220> FEATURE:
<221> NAME/KEY: MISC_FEATURE
<222> LOCATION: (10)..(10)
<223> OTHER INFORMATION: Xaa represents N, V or A
<220> FEATURE:
<221> NAME/KEY: MISC_FEATURE
<222> LOCATION: (11)..(11)
<223> OTHER INFORMATION: Xaa represents K, D, M or A
<220> FEATURE:
<221> NAME/KEY: MISC_FEATURE
<222> LOCATION: (12)..(12)
<223> OTHER INFORMATION: Xaa represents H or S
<220> FEATURE:
<221> NAME/KEY: MISC_FEATURE
<222> LOCATION: (14)..(14)
<223> OTHER INFORMATION: Xaa represents D, E or Xaa is absent
<220> FEATURE:
<221> NAME/KEY: MISC_FEATURE
<222> LOCATION: (15)..(15)
<223> OTHER INFORMATION: Xaa represents L or I
<220> FEATURE:
<221> NAME/KEY: MISC_FEATURE
<222> LOCATION: (17)..(17)
<223> OTHER INFORMATION: Xaa represents G or Xaa is absent

<400> SEQUENCE: 68

Gly Cys Cys Ser Xaa Pro Xaa Cys Xaa Xaa Xaa Xaa Pro Xaa Xaa Cys
1               5                   10                  15

Xaa
```